(12) United States Patent
Hughett et al.

(10) Patent No.: US 10,905,848 B2
(45) Date of Patent: Feb. 2, 2021

(54) CATHETER INSERTION TRAY WITH INTEGRATED INSTRUCTIONS

(71) Applicant: C. R. Bard, Inc., Murray Hill, NJ (US)

(72) Inventors: David Hughett, Monroe, GA (US); Russell Riescher, Loganville, GA (US); John Gohde, Decatur, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 217 days.

(21) Appl. No.: 15/487,297

(22) Filed: Apr. 13, 2017

(65) Prior Publication Data

US 2017/0216558 A1    Aug. 3, 2017

Related U.S. Application Data

(63) Continuation-in-part of application No. 15/029,613, filed as application No. PCT/US2014/060963 on Oct. 16, 2014, now Pat. No. 10,758,705.
(Continued)

(51) Int. Cl.
*A61F 13/38* (2006.01)
*A61B 50/00* (2016.01)
(Continued)

(52) U.S. Cl.
CPC .......... *A61M 25/002* (2013.01); *A61B 50/00* (2016.02); *A61B 50/20* (2016.02); *A61B 50/30* (2016.02);
(Continued)

(58) Field of Classification Search
CPC ..... A61B 19/02; A61B 19/0271; A61B 50/30; A61B 50/33; A61B 2050/3008;
(Continued)

(56) References Cited

U.S. PATENT DOCUMENTS

| 935,419 A | 9/1909 | Smith |
|---|---|---|
| 2,346,636 A | 4/1944 | Porter |

(Continued)

FOREIGN PATENT DOCUMENTS

| CN | 1511014 A | 7/2004 |
|---|---|---|
| CN | 201823147 U | 5/2011 |

(Continued)

OTHER PUBLICATIONS

CN 201480057141.5 filed Apr. 18, 2016 Office Action dated Dec. 4, 2018.
(Continued)

*Primary Examiner* — Anthony D Stashick
*Assistant Examiner* — Lauren Kmet
(74) *Attorney, Agent, or Firm* — Rutan & Tucker LLP

(57) ABSTRACT

An improved medical procedure or catheterization tray included in an improved medical procedure or catheterization package. The improved medical procedure or catheterization tray is intuitively arranged and includes instructions printed thereon to improve the medical procedure or catheterization implementation and results. In one example, a catheterization package and catheterization tray has a layout and/or arrangement of components that may help reduce CAUTI rates by facilitating ease of use and aiding in proper aseptic technique during insertion. The medical procedure or catheterization package and/or medical procedure or catheterization tray may include various implements, compartments, and components necessary and/or helpful to the medical procedure or catheterization, including, for example, improved swabs and an improved compartment for holding the swabs.

27 Claims, 64 Drawing Sheets

Related U.S. Application Data

(60) Provisional application No. 62/015,206, filed on Jun. 20, 2014, provisional application No. 61/891,496, filed on Oct. 16, 2013.

(51) Int. Cl.
| | |
|---|---|
| *A61B 50/30* | (2016.01) |
| *A61B 50/20* | (2016.01) |
| *A61B 50/33* | (2016.01) |
| *A61M 5/00* | (2006.01) |
| *A61M 25/00* | (2006.01) |

(52) U.S. Cl.
CPC .............. *A61B 50/33* (2016.02); *A61F 13/38* (2013.01); *A61B 2050/006* (2016.02); *A61B 2050/0056* (2016.02); *A61B 2050/3008* (2016.02); *A61M 5/002* (2013.01); *A61M 25/0017* (2013.01)

(58) Field of Classification Search
CPC ... A61F 13/38; A61M 25/00; A61M 25/0113; A61M 25/0017; A61M 25/002
USPC .................. 206/216, 570, 223, 364–366, 571
See application file for complete search history.

(56) References Cited

U.S. PATENT DOCUMENTS

| | | | |
|---|---|---|---|
| 2,659,485 A | 11/1953 | Duley et al. |
| 2,874,707 A | 2/1959 | Koppel |
| 2,947,415 A | 8/1960 | Garth |
| 3,107,786 A | 10/1963 | Adelman |
| 3,137,387 A | 6/1964 | Overment |
| 3,138,253 A | 6/1964 | Harautuneian |
| 3,166,189 A | 1/1965 | Disston |
| 3,324,855 A | 6/1967 | Heimlich |
| 3,329,261 A | 7/1967 | Serany, Jr. et al. |
| 3,345,988 A | 10/1967 | Vitello |
| 3,379,339 A | 4/1968 | Asenbauer |
| 3,485,352 A | 12/1969 | Pilger |
| D218,077 S | 7/1970 | Gabriel |
| 3,542,019 A | 11/1970 | Gittins |
| D222,312 S | 10/1971 | Kurtz et al. |
| 3,642,123 A | 2/1972 | Knox |
| 3,650,393 A | 3/1972 | Reiss et al. |
| 3,726,281 A | 4/1973 | Norton et al. |
| 3,762,399 A | 10/1973 | Riedell |
| 3,770,119 A | 11/1973 | Hultberg et al. |
| 3,802,555 A | 4/1974 | Grasty et al. |
| 3,851,649 A | 12/1974 | Villari |
| D234,404 S | 2/1975 | Merrill |
| 3,901,235 A | 8/1975 | Patel et al. |
| D237,315 S | 10/1975 | Nowakowski |
| D237,317 S | 10/1975 | Nowakowski |
| 3,965,900 A | 6/1976 | Boedecker |
| 3,967,728 A | 7/1976 | Gordon et al. |
| 3,976,195 A | 8/1976 | Cohen |
| 3,978,983 A | 9/1976 | Brezette |
| 3,981,398 A | 9/1976 | Boshoff |
| D242,654 S | 12/1976 | Rawls |
| 3,998,221 A | 12/1976 | Collins |
| D243,798 S | 3/1977 | Swartz |
| 4,011,944 A | 3/1977 | Cooley et al. |
| 4,053,280 A | 10/1977 | Salisbury |
| 4,085,845 A | 4/1978 | Perfect |
| D248,871 S | 8/1978 | Forsman et al. |
| D249,362 S | 9/1978 | Forsman et al. |
| 4,140,127 A | 2/1979 | Cianci et al. |
| 4,149,635 A | 4/1979 | Stevens |
| 4,153,160 A | 5/1979 | Leigh |
| 4,160,505 A | 7/1979 | Rauschenberger |
| 4,170,300 A | 10/1979 | Pick |
| 4,226,328 A | 10/1980 | Beddow |
| 4,256,225 A | 3/1981 | Jackson |
| 4,262,800 A * | 4/1981 | Nethercutt ......... A61B 1/00144 206/364 |
| 4,266,669 A | 5/1981 | Watson |
| D262,995 S | 2/1982 | Gaba et al. |
| 4,332,322 A | 6/1982 | Jaeschke et al. |
| 4,334,537 A | 6/1982 | Peterson |
| 4,366,901 A | 1/1983 | Short |
| D268,130 S | 3/1983 | Easton |
| 4,458,705 A | 7/1984 | Cawood |
| D275,886 S | 10/1984 | Sheward et al. |
| D276,462 S | 11/1984 | Villarreal |
| D277,508 S | 2/1985 | Clair |
| 4,501,363 A | 2/1985 | Isbey, Jr. |
| 4,522,302 A | 6/1985 | Paikoff |
| 4,523,679 A | 6/1985 | Paikoff et al. |
| 4,530,349 A | 7/1985 | Metzger |
| D280,663 S | 9/1985 | Albon et al. |
| D280,933 S | 10/1985 | McLaughlin |
| D283,051 S | 3/1986 | Fichera |
| 4,595,102 A | 6/1986 | Cianci et al. |
| D287,760 S | 1/1987 | Discko, Jr. |
| 4,767,008 A | 8/1988 | Warnecke et al. |
| 4,795,441 A | 1/1989 | Bhatt |
| 4,811,847 A | 3/1989 | Reif et al. |
| 4,828,113 A | 5/1989 | Friedland et al. |
| 4,844,259 A | 7/1989 | Glowczewskie, Jr. et al. |
| 4,858,821 A | 8/1989 | Bickelhaupt |
| 4,925,448 A | 5/1990 | Bazaral |
| 4,928,830 A | 5/1990 | Brewer |
| 4,944,427 A | 7/1990 | Yamada et al. |
| D310,896 S | 9/1990 | Winjum |
| 4,989,733 A | 2/1991 | Patry |
| 5,007,535 A | 4/1991 | Meseke et al. |
| 5,024,326 A | 6/1991 | Sandel et al. |
| 5,031,768 A | 7/1991 | Fischer |
| 5,098,391 A | 3/1992 | Pantages et al. |
| 5,163,557 A | 11/1992 | Sokolowski |
| 5,170,804 A | 12/1992 | Glassman |
| D334,973 S | 4/1993 | Valentine et al. |
| D337,830 S | 7/1993 | Coyne et al. |
| 5,242,398 A | 9/1993 | Knoll et al. |
| D343,687 S | 1/1994 | Houghton et al. |
| 5,306,239 A | 4/1994 | Gurmarnik et al. |
| 5,318,543 A | 6/1994 | Ross et al. |
| 5,322,163 A | 6/1994 | Foos |
| 5,339,955 A | 8/1994 | Horan et al. |
| D351,661 S | 10/1994 | Fischer |
| D353,078 S | 12/1994 | Davis et al. |
| 5,392,918 A | 2/1995 | Harrison |
| 5,394,983 A | 3/1995 | Latulippe et al. |
| 5,449,071 A | 9/1995 | Levy |
| 5,525,314 A | 6/1996 | Hurson |
| 5,586,163 A | 12/1996 | Goldstein |
| 5,590,778 A | 1/1997 | Dutchik |
| D380,272 S | 6/1997 | Partika et al. |
| D387,177 S | 12/1997 | Davis |
| D387,559 S | 12/1997 | Williamson |
| 5,704,914 A | 1/1998 | Stocking et al. |
| 5,752,234 A | 5/1998 | Withers |
| 5,779,053 A | 7/1998 | Partika et al. |
| 5,810,738 A | 9/1998 | Thomas, II |
| 5,931,303 A | 8/1999 | Salvadori |
| 5,941,241 A | 8/1999 | Weinstein et al. |
| 5,947,284 A | 9/1999 | Foster |
| 5,947,890 A | 9/1999 | Spencer et al. |
| 5,975,295 A | 11/1999 | Diamond |
| 6,012,586 A | 1/2000 | Misra |
| 6,068,121 A | 5/2000 | McGlinch |
| 6,142,152 A | 11/2000 | Gawarecki |
| 6,158,437 A | 12/2000 | Vagley |
| D437,941 S | 2/2001 | Frattini |
| D442,697 S | 5/2001 | Hajianpour |
| D445,198 S | 7/2001 | Frattini |
| D450,130 S | 11/2001 | Goldstein |
| D450,391 S | 11/2001 | Hunt et al. |
| 6,382,212 B1 | 5/2002 | Borchard |
| 6,405,863 B1 | 6/2002 | Dhindsa |
| 6,412,639 B1 | 7/2002 | Hickey |
| 6,454,097 B1 | 9/2002 | Blanco |

(56) References Cited

U.S. PATENT DOCUMENTS

| | | |
|---|---|---|
| 6,502,699 B1 | 1/2003 | Watson |
| D471,640 S | 3/2003 | McMichael et al. |
| D471,641 S | 3/2003 | McMichael et al. |
| 6,579,271 B1 | 6/2003 | Aruffo et al. |
| D480,816 S | 10/2003 | McMichael et al. |
| 6,640,976 B1 | 11/2003 | Franks-Farah et al. |
| 6,681,933 B1 | 1/2004 | Demsien et al. |
| 6,769,546 B2 | 8/2004 | Busch |
| D495,491 S | 9/2004 | Ramirez et al. |
| D495,807 S | 9/2004 | Agbodoe et al. |
| 6,793,078 B2 | 9/2004 | Roshdy |
| 6,840,379 B2 | 1/2005 | Franks-Farah et al. |
| 6,896,141 B2 | 5/2005 | McMichael et al. |
| 6,907,992 B2 | 6/2005 | McMichael et al. |
| 6,910,581 B2 | 6/2005 | McMichael et al. |
| 6,915,901 B2 | 7/2005 | Feinberg et al. |
| 6,926,708 B1 | 8/2005 | Franks-Farah et al. |
| 6,948,742 B2 | 9/2005 | Buck |
| 6,959,808 B2 * | 11/2005 | Discko, Jr. .......... A61M 35/003 206/209 |
| 6,991,096 B2 | 1/2006 | Gottlieb et al. |
| 7,048,120 B2 | 5/2006 | Pond |
| 7,066,328 B2 | 6/2006 | Pulsifer |
| D530,920 S | 10/2006 | Snell |
| D547,064 S | 7/2007 | Snell |
| D549,454 S | 8/2007 | Ahman |
| 7,264,869 B2 | 9/2007 | Tobita et al. |
| 7,278,987 B2 | 10/2007 | Solazzo |
| D557,047 S | 12/2007 | Dretzka |
| D561,473 S | 2/2008 | Phillips et al. |
| D563,673 S | 3/2008 | Dretzka |
| 7,401,703 B2 | 7/2008 | McMichael et al. |
| 7,410,053 B2 | 8/2008 | Bowen et al. |
| 7,434,687 B2 | 10/2008 | Itou et al. |
| D579,662 S | 11/2008 | Dretzka |
| 7,491,176 B2 | 2/2009 | Mann |
| 7,494,487 B2 | 2/2009 | Timm |
| D590,596 S | 4/2009 | Dretzka |
| D596,311 S | 7/2009 | Antons |
| 7,624,869 B2 | 12/2009 | Primer |
| 7,634,893 B2 | 12/2009 | Gottlieb et al. |
| D609,819 S | 2/2010 | Tomes et al. |
| 7,662,146 B2 | 2/2010 | House |
| D612,153 S | 3/2010 | Liao |
| 7,671,014 B2 | 3/2010 | Beals et al. |
| D613,418 S | 4/2010 | Ryan et al. |
| D618,821 S | 6/2010 | Larsen |
| 7,743,918 B2 | 6/2010 | Itou et al. |
| 7,785,312 B2 | 8/2010 | Thorne, Jr. et al. |
| D623,765 S | 9/2010 | Tomes et al. |
| D631,558 S | 1/2011 | Harmston et al. |
| D636,894 S | 4/2011 | Tomes et al. |
| D638,137 S | 5/2011 | Gross et al. |
| 7,993,326 B2 | 8/2011 | Massengale et al. |
| D646,796 S | 10/2011 | Walter |
| D650,912 S | 12/2011 | Tomes et al. |
| 8,128,595 B2 | 3/2012 | Walker et al. |
| 8,177,064 B2 | 5/2012 | McCormick et al. |
| D662,218 S | 6/2012 | Pittman |
| 8,240,468 B2 | 8/2012 | Wilkinson et al. |
| 8,448,786 B2 | 5/2013 | Tomes et al. |
| D688,461 S | 8/2013 | Ambrefe, Jr. et al. |
| 8,584,849 B2 | 11/2013 | McCaffrey |
| 8,628,549 B2 | 1/2014 | To et al. |
| 8,631,935 B2 | 1/2014 | Tomes et al. |
| 8,656,929 B2 | 2/2014 | Miller et al. |
| 8,662,306 B2 | 3/2014 | Agrawal |
| 8,678,190 B2 | 3/2014 | Tomes et al. |
| 8,708,999 B2 | 4/2014 | Hong et al. |
| D704,856 S | 5/2014 | Tomes et al. |
| D707,848 S | 6/2014 | Shigeno et al. |
| 8,746,452 B2 | 6/2014 | Tomes et al. |
| D708,347 S | 7/2014 | Lober |
| D708,759 S | 7/2014 | Heyman et al. |
| 8,875,940 B2 | 11/2014 | Danchisin et al. |
| D720,470 S | 12/2014 | Lober |
| D720,471 S | 12/2014 | Angel et al. |
| 9,084,593 B2 | 7/2015 | Yakel et al. |
| D738,491 S | 9/2015 | Foley et al. |
| 9,162,781 B2 | 10/2015 | Lien |
| 9,186,217 B2 | 11/2015 | Goyal |
| D751,726 S | 3/2016 | Nishioka et al. |
| 9,283,352 B2 | 3/2016 | Tomes et al. |
| 9,486,604 B2 | 11/2016 | Murray et al. |
| 9,522,001 B2 | 12/2016 | Bui et al. |
| 9,522,753 B2 | 12/2016 | Tomes et al. |
| 9,693,756 B2 | 7/2017 | Tomes et al. |
| 9,744,333 B2 | 8/2017 | Terzibashian |
| 9,745,088 B2 | 8/2017 | Tomes et al. |
| 9,795,761 B2 | 10/2017 | Lockwood et al. |
| 9,808,400 B2 | 11/2017 | Tomes et al. |
| 9,808,596 B2 | 11/2017 | Tomes et al. |
| 9,872,969 B2 | 1/2018 | Conway et al. |
| 10,022,464 B2 | 7/2018 | Sarphati et al. |
| 10,039,897 B2 | 8/2018 | Norris et al. |
| 10,106,295 B2 | 10/2018 | Lockwood |
| 10,251,812 B2 | 4/2019 | Tomes et al. |
| 10,512,752 B2 | 12/2019 | Tomes et al. |
| 10,639,120 B2 | 5/2020 | Turturro et al. |
| 2002/0185406 A1 | 12/2002 | Massengale et al. |
| 2003/0038475 A1 | 2/2003 | Stancil |
| 2003/0060761 A1 | 3/2003 | Evans et al. |
| 2003/0075474 A1 | 4/2003 | Moyer et al. |
| 2003/0159966 A1 | 8/2003 | McMichael et al. |
| 2003/0159967 A1 | 8/2003 | McMichael et al. |
| 2003/0159968 A1 | 8/2003 | McMichael et al. |
| 2003/0159969 A1 | 8/2003 | McMichael et al. |
| 2003/0211627 A1 | 11/2003 | Koesterman et al. |
| 2004/0004019 A1 | 1/2004 | Busch |
| 2004/0055919 A1 | 3/2004 | Rowe et al. |
| 2004/0060260 A1 | 4/2004 | Gottlieb et al. |
| 2004/0111072 A1 | 6/2004 | McKissick |
| 2004/0195145 A1 | 10/2004 | Roshdy |
| 2004/0200754 A1 | 10/2004 | Hagemeier |
| 2004/0238391 A1 | 12/2004 | Pond |
| 2005/0022822 A1 | 2/2005 | Santilli et al. |
| 2005/0098470 A1 | 5/2005 | Davis et al. |
| 2005/0101905 A1 | 5/2005 | Merry |
| 2005/0236940 A1 | 10/2005 | Rockoff |
| 2005/0256453 A1 | 11/2005 | Nagamatsu |
| 2005/0285385 A1 | 12/2005 | Bova et al. |
| 2006/0009742 A1 | 1/2006 | Solazzo |
| 2006/0086634 A1 | 4/2006 | Steppe |
| 2006/0104857 A1 | 5/2006 | Pigott et al. |
| 2006/0186010 A1 | 8/2006 | Warnack et al. |
| 2006/0264822 A1 | 11/2006 | Nagamatsu |
| 2006/0271019 A1 | 11/2006 | Stoller et al. |
| 2006/0282045 A1 | 12/2006 | Wilkinson et al. |
| 2007/0026472 A1 | 2/2007 | Prokash et al. |
| 2007/0060908 A1 | 3/2007 | Webster et al. |
| 2007/0084742 A1 | 4/2007 | Miller et al. |
| 2007/0088330 A1 | 4/2007 | House |
| 2007/0095699 A1 | 5/2007 | Frieze et al. |
| 2007/0142786 A1 | 6/2007 | Lampropoulos et al. |
| 2007/0156099 A1 | 7/2007 | Fowler |
| 2007/0161971 A1 | 7/2007 | House |
| 2007/0197998 A1 | 8/2007 | Itou et al. |
| 2007/0225687 A1 | 9/2007 | House |
| 2007/0273258 A1 | 11/2007 | Ernst |
| 2007/0299431 A1 | 12/2007 | Jakubowski et al. |
| 2008/0045861 A1 | 2/2008 | Miller et al. |
| 2008/0058725 A1 | 3/2008 | Scribner et al. |
| 2008/0116106 A1 | 5/2008 | Lampropoulos et al. |
| 2008/0121553 A1 | 5/2008 | Gobel |
| 2008/0125722 A1 | 5/2008 | Hess et al. |
| 2008/0172042 A1 | 7/2008 | House |
| 2008/0221515 A1 | 9/2008 | Nagamatsu |
| 2008/0249482 A1 | 10/2008 | Erez |
| 2008/0272023 A1 | 11/2008 | McCormick et al. |
| 2008/0283426 A1 | 11/2008 | Primer et al. |
| 2008/0283433 A1 | 11/2008 | Primer |
| 2009/0184026 A1 | 7/2009 | Massengale et al. |
| 2009/0194453 A1 | 8/2009 | Thorne, Jr. et al. |
| 2009/0208368 A1 | 8/2009 | Waldrep et al. |

(56) References Cited

U.S. PATENT DOCUMENTS

| | | |
|---|---|---|
| 2009/0234346 A1 | 9/2009 | McBride, Jr. et al. |
| 2009/0236259 A1 | 9/2009 | Hicks |
| 2010/0274205 A1 | 10/2010 | Morelli et al. |
| 2010/0307941 A1 | 12/2010 | Tomes et al. |
| 2010/0307942 A1 | 12/2010 | Tomes et al. |
| 2010/0311026 A1 | 12/2010 | Tomes et al. |
| 2011/0107494 A1 | 5/2011 | Haines |
| 2011/0120906 A1 | 5/2011 | Umholtz et al. |
| 2011/0155599 A1 | 6/2011 | Yakel et al. |
| 2011/0203957 A1* | 8/2011 | Zoland .................. A61B 50/10 206/363 |
| 2011/0232234 A1 | 9/2011 | Lockwood et al. |
| 2011/0233079 A1 | 9/2011 | Macinnes et al. |
| 2011/0284410 A1 | 11/2011 | Lockwood |
| 2011/0290260 A1 | 12/2011 | Tomes et al. |
| 2011/0290262 A1 | 12/2011 | Tomes et al. |
| 2011/0297147 A1 | 12/2011 | Lick et al. |
| 2012/0145589 A1 | 6/2012 | Macinnes et al. |
| 2012/0150123 A1 | 6/2012 | Lawrence et al. |
| 2012/0222686 A1 | 9/2012 | Lockwood et al. |
| 2013/0037440 A1 | 2/2013 | Danchisin et al. |
| 2013/0042576 A1 | 2/2013 | Sweeney |
| 2013/0269713 A1 | 10/2013 | Bui et al. |
| 2013/0277248 A1 | 10/2013 | Tomes et al. |
| 2013/0277262 A1* | 10/2013 | Nemard .................. A61J 1/03 206/438 |
| 2014/0021087 A1 | 1/2014 | Adler et al. |
| 2014/0039349 A1 | 2/2014 | Moghe et al. |
| 2014/0100551 A1 | 4/2014 | Holmstrom |
| 2014/0142465 A1 | 5/2014 | Tomes et al. |
| 2014/0231287 A1 | 8/2014 | Tomes et al. |
| 2014/0231288 A1 | 8/2014 | Tomes et al. |
| 2014/0262851 A1 | 9/2014 | Adler et al. |
| 2015/0048103 A1 | 2/2015 | Danchisin et al. |
| 2015/0083627 A1 | 3/2015 | Gorman |
| 2015/0151017 A1* | 6/2015 | Tipton .................. A61L 2/26 422/310 |
| 2015/0258304 A1 | 9/2015 | Tomes et al. |
| 2015/0283354 A1 | 10/2015 | Olson et al. |
| 2015/0335855 A1 | 11/2015 | Tomes et al. |
| 2016/0166800 A1 | 6/2016 | Tomes et al. |
| 2016/0193444 A1 | 7/2016 | Tomes et al. |
| 2016/0228676 A1 | 8/2016 | Glithero et al. |
| 2016/0243332 A1 | 8/2016 | Portela et al. |
| 2017/0056122 A1 | 3/2017 | Ramsey |
| 2017/0056125 A1 | 3/2017 | Garza et al. |
| 2017/0106165 A1 | 4/2017 | Holmes |
| 2017/0202699 A1 | 7/2017 | Zani et al. |
| 2017/0216557 A1 | 8/2017 | Kearns et al. |
| 2017/0231804 A1 | 8/2017 | Miller et al. |
| 2017/0232226 A1 | 8/2017 | Loui et al. |
| 2017/0296282 A1 | 10/2017 | Turturro et al. |
| 2017/0296283 A1 | 10/2017 | Turturro et al. |
| 2017/0296284 A1 | 10/2017 | Turturro et al. |
| 2017/0319183 A1 | 11/2017 | Tomes et al. |
| 2017/0349305 A1 | 12/2017 | Tomes et al. |
| 2017/0368302 A1 | 12/2017 | Brooks et al. |
| 2018/0001052 A1 | 1/2018 | Lockwood et al. |
| 2018/0056030 A1 | 3/2018 | Tomes et al. |
| 2018/0057196 A1 | 3/2018 | Tomes et al. |
| 2018/0206933 A1 | 7/2018 | Healey et al. |
| 2018/0221564 A1 | 8/2018 | Patel et al. |
| 2019/0151195 A1 | 5/2019 | Tomes et al. |

FOREIGN PATENT DOCUMENTS

| | | |
|---|---|---|
| DE | 102007003223 B4 | 12/2009 |
| EP | 1301782 A1 | 4/2003 |
| EP | 1595561 A2 | 11/2005 |
| EP | 1731189 A1 | 12/2006 |
| FR | 2780274 A1 | 12/1999 |
| FR | 2873929 A1 | 2/2006 |
| GB | 2365342 A | 2/2002 |
| JP | S50-149175 A | 11/1975 |
| JP | 2002-136597 A | 5/2002 |
| JP | 2005-506110 A | 3/2005 |
| JP | 2007-229520 A | 9/2007 |
| JP | 2007-319535 A | 12/2007 |
| JP | 2010-200809 A | 9/2010 |
| JP | 2011-520578 A | 7/2011 |
| WO | 9106255 A1 | 5/1991 |
| WO | 9607364 A1 | 3/1996 |
| WO | 02/004942 A1 | 1/2002 |
| WO | 02064078 A1 | 8/2002 |
| WO | 2002083021 A1 | 10/2002 |
| WO | 2004005157 A1 | 1/2004 |
| WO | 2005/027767 A1 | 3/2005 |
| WO | 2006114466 A1 | 11/2006 |
| WO | 2007/045943 A1 | 4/2007 |
| WO | 08033873 A2 | 3/2008 |
| WO | 2008139852 A1 | 11/2008 |
| WO | 2015/057999 A1 | 4/2015 |
| WO | 2015057999 | 4/2015 |
| WO | 2017147067 A1 | 8/2017 |
| WO | 2018044772 A1 | 3/2018 |
| WO | 2018057835 A1 | 3/2018 |
| WO | 2018/183752 A1 | 10/2018 |
| WO | 2018/190865 A1 | 10/2018 |
| WO | 2019/209867 A1 | 10/2019 |

OTHER PUBLICATIONS

U.S. Appl. No. 15/029,613, filed Apr. 14, 2016 Non-Final Office Action dated Nov. 29, 2018.

AU 2014337176 filed Mar. 15, 2016 Examination Report dated Aug. 1, 2018.

JP 2016-523921 filed Apr. 15, 2016 Office Action dated Jul. 11, 2018.

Bardex I.C. Complete Care StateLock Device 350 ml Urine Meter Foley Tray with Bacteriostatic Collection System, Directions for Use; Dated 2006.

Bardex I.C. Infection Control 350 ml Urine Meter Foley Tray, Directions for Use; Dated 2006.

Bardex I.C. Infection Control Foley Tray, Directions for Use; Dated 2006.

C.R. Bard, Inc; "A few important words about Catheter Care"; Dated 2001.

EP 14853869.7 filed Mar. 31, 2016 Extended European Search Report dated Aug. 4, 2017.

Ortega, R. et. al. "Female Urethral Catheterization", N Engl J Med 2008; 358: e15. Apr. 3, 2008.

PCT/US2017/027628 filed Apr. 14, 2017 International Search Report and Written Opinion dated Jul. 17, 2017.

Thomson et. al. "Male Urethral Catheterization", N Engl J Med 2006; 354: e22. May 25, 2006.

"Arrow International, Inc. Introduces Maximal Barrier Precautions Tray", Press release. Jan. 11, 2006.

Arrow, "Arrow Trauma Products" brochure, 2000.

PCT/US14/60963 filed Oct. 16, 2014 International Search Report and Written Opinion dated Jan. 14, 2015.

Request for Inter partes Review of U.S. Pat. No. 8,631,935, filed Dec. 30, 2014.

U.S. Appl. No. 15/029,613, filed Apr. 14, 2016 Final Office Action dated Apr. 10, 2019.

Addison, R. et al., "Catheter Care," Royal College of Nursing, London (2008).

C. R. Bard Urological Drainage, https://www.crbard.com/medical/Professionals/Product-Concentrations/Urological-Drainage, last accessed 2019.

California Department of Public Health, "Catheter-Associated Urinary Tract Infection (CAUTI) Prevention" (2015).

Dept. of Health and Human Services, "Action Plan to Prevent Healthcare-Associated Infections." (2009).

Ellen Elpem, et al., "Prevention of Catheter-Associated Urinary Tract Infections in Adults," 36 Critical Care Nurse, 9 (2016).

EP 14853869.7 filed Mar. 31, 2016 Office Action dated Mar. 13, 2019.

(56) References Cited

OTHER PUBLICATIONS

Foxman, B. "Epidemiology of Urinary Tract Infections: Incidence, Morbidity, and Economic Costs." The American Journal of Medicine, 113 Suppl 1A (2002).
Gould et al., "Catheter-associated Urinary Tract Infection (CAUTI) Toolkit," Centers for Disease Control and Prevention Devision of Healthcare Quality Promotion. (2009).
Gould et al., "Guideline for Prevention of Catheter Associated Urinary Tract Infections," Centers for Disease Control Healthcare Infection Control Practices Advisory Committee, (2009).
Greene, L. et al. "Guide to the Elimination of Catheter-Associated Urinary TractInfections (CAUTIs): Developing and Applying Facility-Based Prevention Interventions in Acute and Long-Term Care Settings," Association for Professionals in Infection Control and Epidemiology, (2008).
Jacobsen, S. M. et al., "Complicated Catheter-Associated UrinaryTract Infections Due to *Escherichia coli* and Proteus mirabilis", 21 Clinical Microbiology Reviews 1, 26-59 (Jan. 2008).
Jennifer A Meddings, "Implementing Strategies to Reduce Hospital-Acquired Catheter-Associated Urinary Tract Infection," Wound, Ostomy and Continence Nurses Society, www.catheterout.org, (Jun. 2010).
Linda Kohn et al., eds., "To Err is Human: Building a Safer Health System," Institute of Medicine (US), (2000).
Lo, E. et al., "Strategies to Prevent Catheter-Associated Urinary Tract Infections in Acute Care Hospitals," Infection Control and Hospital Epidemiology. 29, S41-S50 (2008).
Madeo M. et al., "Reducing the risks associated with urinary catheters." Nursing Standard, vol. 23, No. 29, 47-55 (2009).
PCT/US2018/025260 filed Mar. 29, 2018 International Search Report and Written Opinion dated Jun. 7, 2018.
Saint et al., "Catheter-Associated Urinary Tract Infection and the Medicare Rule Changes," Annals of Internal Medicine, Jun. 16, 2009.
Steultjens, M.P.M. et al., "Range of joint motion and disability in patients with osteoarthritis of the knee or hip," Rheumatology, Bristish Society for Rheumatology. (2000).
The Joint Commision on National Patient Safety, "2012 National Patient Safety Goals: Hospital accreditation Program." (2012).
Urological Drainage website, http://m.bardmedical.com/products/urological-drainage/, last accessed 2019.

\* cited by examiner

Directions for Use and Patient Education Information

Proper Techniques for Urinary Catheter Insertion

- Perform hand hygiene immediately before and after insertion
- Insert urinary catheters using aseptic technique and sterile equipment
- Use the smallest Foley catheter possible, consistent with good drainage
- Document the indications for catheter insertion, date and time of catheter insertion, individual who inserted catheter, and date and time of catheter removal in patient record

Proper Techniques for Urinary Catheter Maintenance

- Secure the Foley Catheter, use the STATLOCK® Foley Stabilization Device if provided
- Maintain a closed drainage system by utilizing pre-connected, sealed catheter-tubing junctions
- Maintain unobstructed urine flow and keep the catheter and collection tube free from kinking
- Keep the collection bag below the level of the bladder or hips at all times
- Empty the collection bag regularly (e.g., prior to transport) using a separate, clean collection container for each patient
- Routine hygiene (e.g., cleansing of the meatal surface during daily bathing or showering) is appropriate
- Leave Foley catheter in place only as long as needed

MEDICAL

*FIG. 14A*

PATIENT/FAMILY EDUCATION

Your Foley Catheter

A urinary catheter is a thin tube placed in the bladder to drain urine. The urine drains through a tube into the collection bag. If you have a urinary catheter, it is possible for germs to travel along the catheter and cause an infection in your bladder or your kidney; in that case it is called a catheter-associated urinary tract infection (or CA-UTI).

*How can I take every precaution to prevent catheter-associated urinary tract infections?*

- Ask your healthcare provider each day if you still need your catheter

- Make sure your catheter tubing is secured to your leg or abdomen if possible

- Make sure all hospital staff wash or sanitize their hands before & after touching your catheter

- Do not tug, pull or twist the catheter tubing

- Always keep your urine drain bag below the level of your bladder or hips and off the floor

- Avoid disconnecting the catheter from the drain tube

*FIG. 15A*

EDUCACIÓN DEL PACIENTE/FAMILIAR

Su sonda Foley

Una sonda o catéter urinario consiste en un tubo delgado que se coloca en la vejiga para drenar la orina. La orina se drena por medio de un tubo y se recoge en una bolsa. Si lleva una sonda urinaria, los gérmenes pueden desplazarse por el catéter y causar una infección en la vejiga o el riñón; en tal caso, se produciría una infección del tracto urinario asociada a catéter urinario (o ITU-CU).

*¿Cómo puede prevenir las infecciones del tracto urinario asociadas a catéter urinario?*

Pregunte todos los días a su médico si debe seguir llevando la sonda.

Asegúrese de que el tubo de la sonda esté fijado a la pierna o al abdomen si es posible.

Asegúrese de que todo el personal del hospital se limpie o esterilice las manos antes y después de tocar la sonda.

No doble, tire ni estire del tubo d la sonda.

Mantenga siempre la bolsa de drenaje urinario por debajo del nivel de la vejiga o la cadera y por encima del suelo.

Evite desconectar la sonda del tubo de drenaje.

*FIG. 15B*

CATHETER INSERTION TRAY WITH INTEGRATED INSTRUCTIONS

PRIORITY

This application is a continuation-in-part of U.S. patent application Ser. No. 15/029,613, filed Apr. 14, 2016, now U.S. Pat. No. 10,758,705, which is a U.S. national stage of International Patent Application No. PCT/US2014/060963, filed Oct. 16, 2014, which claims the benefit of U.S. Provisional Patent Application No. 61/891,496, filed Oct. 16, 2013, and U.S. Provisional Patent Application No. 62/015,206, filed Jun. 20, 2014, each of which is hereby incorporated herein by reference in its entirety.

BACKGROUND

Urinary drainage systems are conventionally used in hospitals and health care facilities when it is necessary to facilitate, control, monitor urination of patients, and when it is necessary to collect urine from a patient. These urinary drainage systems permit the patient to remain in bed, without having to use a bedpan or be moved to use a bathroom. Urinary drainage systems may include a catheter (e.g., a urinary catheter, such as an intermittent catheter or a Foley catheter), a collection container/bag (e.g., a bag made of a polymeric material or PVC film), a urine meter, tubing connecting the Foley catheter to the collection container/bag or urine meter, and/or other equipment. In operation, the patient is first catheterized, and the catheter is connected to the drainage container/bag and/or urine meter through a length of tubing (e.g., drainage tubing). The urine drains through the catheter, the tubing, and then finally into the collection container/bag and/or urine meter. The urine may be moved from the catheter into the collection bag solely due to gravitational forces. On average, a patient produces about 80-90 mL of urine in 1 hour.

Accurate monitoring of urine helps the clinician detect irregularities in urine flow rate or volume that can signal to the clinician that the patient is suffering certain problems. However, urine output cannot be accurately measured if the drainage system attached to the Foley catheter is not reliable, or if the Foley catheter and drainage system are not properly used. Further, hospitals are using increasingly lower-profile beds in order to reduce the number of injuries sustained from falls. With the adoption of lower profile beds, the amount of height available to allow the tubing to drain is decreased. Drainage tubing used in hospitals and associated venting systems have also undergone changes/revisions. Changes in venting combined with increasingly lower profile hospital beds have created suboptimal drainage performance. For example, urine has been observed pooling in the tubing. This prevents accurate urine output and flow rate measurements, which are critical for many patients.

Currently, the second-most common form of Hospital Acquired Infection (HAI) is catheter-associated urinary tract infection (CAUTI). Hospitals are interested in ways to cut their CAUTI rates by conforming to a strict aseptic technique as a standard of care. However, there are many factors that influence a hospital's ability to meet the standard of care. These factors include: health care practitioner/nurse experience and training, patient factors (e.g., general health, weight, and anatomy), environmental factors, and tray layout as well as contents and instructions/indicators. A catheterization package and/or catheterization tray with components optimized to the procedure and an intuitive layout can increase compliance to aseptic technique, potentially reducing CAUTI rates.

There is a need in the healthcare field for a more reliable, safe, and easy method for inserting a catheter, such as a urinary catheter, for example an indwelling or intermittent catheter, into a patient. More particularly, there is a need to provide a catheterization package and/or a catheterization tray (e.g., a Foley catheter tray) that improves and standardizes the process for inserting a urinary catheter, such as an indwelling Foley catheter, into a patient.

The present disclosure provides a catheterization package, catheter tray, and drainage system configured to better meet patients' needs, improve reliability and ease of use, reduce incidents of CAUTI, improve safety, and address other issues described above and elsewhere herein.

SUMMARY

Embodiments of, and enhancements for, packages, systems, trays, assemblies, devices, methods, etc. used for medical treatment generally and catheterization, in particular, are described herein.

The objectives described herein can be met by providing an improved medical procedure package and/or tray (e.g., an improved catheterization package and/or an improved catheterization tray). The improved medical procedure package may include the improved medical procedure tray therein, and the medical procedure tray may be intuitively arranged and may include instructions or procedural indicators to improve the medical procedure implementation and results. The medical procedure package and/or medical procedure tray may include various implements and components necessary and/or helpful to the medical procedure. For example, an improved catheterization package may include an improved catheterization tray, povidone iodine swabs or swabsticks that allow for greater coverage and saturation, hand sanitizer with improved efficacy and that enables single-handed usage, tubing that breaks up the surface tension of the fluid in order to improve drainage, and/or other components described herein.

According to various embodiments, the present disclosure provides a catheterization package and catheterization tray having a layout and/or arrangement of components that may help reduce CAUTI rates by facilitating ease of use and aiding in proper aseptic technique during insertion. The present disclosure also provides methods of catheterization and use of a catheterization package and/or catheterization tray that may facilitate easier and more sterile catheterization to help reduce CAUTI rates. Further, the present disclosure provides a system that may improve drainage performance, which in turn: (1) helps to eliminate fluid in the drain tubing, and (2) increases the accuracy of urine measurements (e.g., measurements of output and flow).

In some embodiments, a catheterization package is provided including a catheterization tray and a sterile wrap around the catheterization tray. The catheterization tray can include catheterization instructions imprinted directly on the catheterization tray. The catheterization tray can also include a first section, a second section, and a third section, wherein in one or more partitions can separate at least the third section from the first and second sections. The first section can hold a drainage system, the second section can hold a container containing lubricant, and the third section can hold a swab in an inclined position. The absorbent head of the swab can angle downwardly into a well of the third section and an elongate member of the swab can angle upwardly for gripping and removal of the swab.

In such embodiments, the catheterization package can further include a peri-care kit, a belly band, and a packaging label. The peri-care kit can be packaged with the catheterization tray but outside the sterile wrap. One example of a suitable peri-care kit is disclosed in PCT Application Publication No. WO 2016/126555, the disclosure of which is incorporated herein by reference in its entirety. The belly band can be outside the sterile wrap holding the sterile wrap in a folded configuration around the catheterization tray. The packaging label can be outside the sterile wrap for identifying the catheterization package.

In such embodiments, the third section of the catheterization package can include a swab compartment, an overflow compartment, and a corner storage compartment holding a specimen container. The swab compartment can include the well and a channel configured to hold the swab. The channel can include at least two snap-in tabs to hold the swab in the channel under the snap-in tabs, wherein each longitudinal side of the channel includes at least one of the at least two snap-in tabs. The channel can be further configured to convey a fluid to the well when the swab is absent from the channel and the fluid is poured in the channel. The overflow compartment can be fluidly connected to the well through the channel.

In such embodiments, the one or more partitions of the catheterization package separating the third section from the first and second sections can further separate the second section from the first section. Second section-separating partitions of the one or more partitions can have a maximum height equal to a height of the catheterization tray, wherein a bottom of the second section can be elevated above a bottom of the catheterization tray. Alternatively, the second section-separating partitions of the one or more partitions can have a maximum height less than the height of the catheterization tray, wherein the bottom of the second section and the bottom of the catheterization tray are substantially co-planar.

In some embodiments, a medical-procedure package is provided including a tray with medical-procedure instructions imprinted directly on the tray, at least some of which instructions are revealed in step with steps of the medical procedure. The tray can include a first section, a second section, and a third section, wherein one or more partitions separate at least the third section from the first and second sections. The tray can further include a drainage system, a container containing a lubricant, and one or more swabs. The first section can include at least the drainage system, the second section can include at least the container containing the lubricant, and the third section includes at least the one or more swabs.

In such embodiments, the medical-procedure package can further include a specimen container. The third section can include a swab compartment, an overflow compartment, and a corner storage compartment including the specimen container. The swab compartment can include a well and one or more channels configured to respectively hold the one or more swabs with snap-in tabs in the one or more channels. The one or more channels can also be angled with respect to a bottom of the tray such that a handle end of each swab of the one or more swabs held under the snap-in tabs is elevated with respect to an absorbent-head end when the absorbent-head end is in the well. The overflow compartment can be fluidly connected to the well through the one or more channels, wherein the one or more channels can be further configured to convey a fluid poured therein to the well when the one or more swabs are removed from the one or more channels.

In such embodiments, the medical-procedure package can further include a third section-separating partition of the one or more partitions at a well-end of the swab compartment directly separating the well from the second section. Alternatively, a well-end of the swab compartment can share with the tray an inner wall of the tray.

In such embodiments, the one or more partitions of the medical-procedure package separating the third section from the first and second sections can further separate the second section from the first section. Second section-separating partitions of the one or more partitions can have a maximum height equal to a height of the tray, wherein a bottom of the second section can be elevated above a bottom of the tray. Alternatively, the second section-separating partitions of the one or more partitions can have a maximum height less than the height of the tray, wherein the bottom of the second section and the bottom of the tray are substantially co-planar.

In some embodiments, a catheterization package is provided including a tray with instructions for a catheterization procedure imprinted directly on the tray, at least some of which instructions are revealed in step with steps of the catheterization procedure. The tray can include a first section, a second section, and a third section, wherein one or more partitions separate at least the third section from the first and second sections. The tray can further include a drainage system, a container containing a lubricant, a syringe of sterile liquid, such as water or, in some instances, saline, and a skin-preparation kit. The first section can include at least the drainage system, which drainage system can include a Foley catheter, drainage tubing, and a drainage bag. The second section can include at least the container containing the lubricant. The first section can include the syringe of the sterile liquid, such as sterile water, which syringe can be configured for inflating a balloon of the Foley catheter with the sterile water. According to certain embodiments, the water syringe can be connected to the inflation port of the Foley catheter during manufacture of the assembly. Providing a pre-connected syringe to the Foley catheter can help minimize the number of steps required to catheterize a patient. The third section can include at least the skin-preparation kit, which kit can include a package of an antiseptic and one or more swabs.

In such embodiments, the catheterization package can further include a specimen container and a label for the specimen container. The third section can include a swab compartment, an overflow compartment, and a corner storage compartment including the specimen container. The swab compartment can include a well and one or more channels configured to respectively hold the one or more swabs with snap-in tabs in the one or more channels. The overflow compartment can be fluidly connected to the well through the one or more channels, wherein the one or more channels can be further configured to convey the antiseptic poured therein to the well when the one or more swabs are removed from the one or more channels. The package of the antiseptic can be placed over the swab compartment, the overflow compartment, the corner storage compartment, or a combination thereof.

In such embodiments, the catheterization package can further include a third section-separating partition of the one or more partitions at a well-end of the swab compartment directly separating the well from the second section. Alternatively, a well-end of the swab compartment can share with the tray an inner wall of the tray.

In such embodiments, the one or more partitions of the catheterization package separating the third section from the first and second sections can further separate the second section from the first section. Second section-separating partitions of the one or more partitions can have a maximum height equal to a height of the tray, wherein a bottom of the second section can be elevated above a bottom of the tray. Alternatively, the second section-separating partitions of the one or more partitions can have a maximum height less than the height of the tray, wherein the bottom of the second section and the bottom of the tray are substantially co-planar.

In such embodiments, the catheterization package can further include a sterile wrap, a peri-care kit, a belly band, and a packaging label. The sterile wrap can be in a folded configuration around the tray. The peri-care kit can be packaged with the catheterization tray but outside the sterile wrap. The belly band can be outside the sterile wrap holding the sterile wrap in the folded configuration around the catheterization tray. The belly band can also include instructions regarding how to orient the tray prior to opening the sterile wrap. The packaging label can be outside the sterile wrap for identifying the catheterization package. In addition, the packaging label can include information emphasizing key features of the catheterization package in a way that is easy to read quickly.

In some embodiments, a catheterization package comprises a catheterization tray including a first compartment holding a drainage system; a second compartment holding a syringe; a third compartment holding a swab in an inclined position such that an absorbent head of the swab is biased downwardly into a well of the third compartment and an elongate member of the swab angles upwardly for easier gripping and removal; and catheterization instructions or procedural indicators imprinted directly on the catheterization tray. The catheterization package may also include a sterile wrap (e.g., a CSR wrap) wrapped around the catheterization tray. The absorbent head of the swab may be formed of absorbent foam, and the elongate member of the swab may have a generally rectangular cross section with rounded edges. The catheterization package may also include a peri-care kit packaged with the catheterization tray at a location outside the sterile wrap. The catheterization package may also include a belly band outside the sterile wrap, the belly band including an instruction or procedural indicator regarding how to orient the catheterization tray prior to opening the sterile wrap. Additionally, the catheterization package may include a packaging label outside the sterile wrap, wherein the packaging label includes at least three sides folded into a different plane from the top portion of the label that are visible when viewing the catheterization package from one or more sides of the catheterization package, and/or wherein the packaging label includes information features (e.g., information squares) that each emphasize a key feature of the catheterization package in a way that is easy to read quickly. The catheterization package may include an outer sealed container or bag (e.g., a plastic, transparent bag) around the other components to maintain sterility during shipping and storage.

In some embodiments, a medical procedure package comprises three or more compartments holding implements useful for performance of the medical procedure and instructions/procedural indicators imprinted or included directly on the medical procedure tray directing a user how to carry out steps of the medical procedure, wherein the three or more compartments of the medical procedure tray, the instructions/procedural indicators, and implements are arranged in an arrangement such that the medical procedure proceeds intuitively from step to step based on the arrangement. The arrangement may include stacking various components or implements (e.g., 2 to 20 implements/components or 4 to 10 implements/components) on top of each other in the order that they are to be used (e.g., with components or implements to be used before other components or implements being positioned on top of the other components or implements to be used later).

In some embodiments, a method of treating a patient comprises providing a medical procedure tray including three or more compartments including implements useful for performance of the medical procedure and instructions/procedural indicators imprinted directly on the medical procedure tray directing a user how to carry out steps of the medical procedure. The method may also include performing the medical procedure on a patient while following the instructions/procedural indicators imprinted on the medical procedure tray. Three or more compartments of the medical procedure tray, the instructions/procedural indicators, and/or implements are arranged such that the medical procedure proceeds intuitively from step to step based on how they are arranged on/in the medical procedure tray.

In some embodiments, a method of catheterizing a patient comprises providing a catheterization package having a catheterization tray including a first compartment holding a drainage system including a catheter; a second compartment holding a swab in an inclined position such that and absorbent head of the swab is biased downwardly into a well of the second compartment and an elongate member of the swab angles upwardly; pouring an antiseptic solution into the well such that the absorbent head is in contact with the antiseptic solution, using the swab to cleanse the patient in a region to be catheterized, and inserting a portion of a catheter into a urethra of the patient. A sealed container or bag may be disposed around the catheterization tray, and the method may include unsealing the sealed container or bag. A sterile wrap may be wrapped around the catheterization tray, and the method may include unwrapping the sterile wrap prior to pouring an antiseptic solution into the well. The catheterization package may also include a peri-care kit located outside of the sterile wrap, and the method may include using the peri-care kit to cleanse a portion of the patient's perineum prior to unwrapping the sterile wrap. A belly band may be positioned outside the sterile wrap, the belly band may include an instruction/procedural indicator or instructions/procedural indicators regarding how to properly orient the catheterization tray prior to opening the sterile wrap, and the method may include orienting the tray according to the instruction(s)/procedural indicator(s) prior to unwrapping the sterile wrap.

In some embodiments, a method of manufacturing a catheterization package comprises providing a catheterization tray including a first compartment, a second compartment, a third compartment having an inclined portion of the bottom of the compartment with channels for holding a swab, and catheterization instructions/procedural indicators imprinted directly on the catheterization tray; wherein the first compartment, the second compartment, and the third compartment are each at least partially separated from each other by partitions. The method may also include positioning a drainage system in the first compartment, a syringe in the second compartment, and a swab in the third compartment such that an absorbent head of the swab is biased downwardly into a well of the third compartment and an elongate member of the swab angles upwardly for easier gripping and removal. The method may further include wrapping the catheterization tray in a sterile wrap and positioning a belly band around a portion of the sterile wrap, the belly band including an instruction/procedural indicator or instructions/procedural indicators regarding how to properly orient the catheterization tray prior to opening the sterile wrap. In addition, the method may include adding a peri-care kit to the catheterization tray outside the belly band and sterile wrap, the peri-care kit including a baggy with a zipper holding cleansing towelettes, hand sanitizer, and instructions/procedural indicators for cleansing the patient. The method may include adding a document of detailed catheterization instructions and/or procedural indicators to the catheterization package. Also, the method may include placing a packaging label on top of the catheterization package, the packaging label including at least three side portions folded from the top portion, and/or placing a packaging label on top of the catheterization package, the packaging label including an information feature or information features that each emphasize one or more key features of the catheterization package in a way that is easy to read quickly. The information feature or information features may be an information square or multiple information squares. The method may also include sealing (e.g., by heat sealing) a transparent plastic bag around the catheterization package.

In some embodiments, a catheterization system includes a container for securing components for a catheterization procedure. The container has an outer shell defining a general shape of the container and a plurality of compartments within the outer shell. Each of the plurality of compartments is separated from one or more adjacent compartments of the plurality of compartments by one or more partitions. The plurality of compartments include a first compartment sized and configured to contain a catheter assembly and one or more secondary compartments separated from the first compartment by the one or more partitions. At least one of the one or more secondary compartments includes at least one partial partition (e.g., a partition that includes a reduced height portion) of the one or more partitions.

In some embodiments, a catheterization system for performing a catheterization procedure is provided. The catheterization system includes a catheterization tray that has an outer shell defining a general shape of the container and a plurality of compartments within the outer shell. Each of the plurality of compartments is separated from one or more adjacent compartments of the plurality of compartments by one or more partitions. The plurality of compartments may include a first compartment containing a catheter assembly and one or more secondary compartments separated from the first compartment by the one or more partitions. At least one of the one or more secondary compartments may include at least one partial partition (e.g., a partition that includes a reduced height portion) of the one or more partitions. Additionally, the catheterization system includes one or more swabs located in a second compartment of the one or more secondary compartments.

DRAWINGS

The disclosed embodiments of, and enhancements for, packages, trays, devices, systems and methods can be better understood with reference to the following drawings. Portions of the material in this patent document are subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever.

FIG. 14A shows a page of a document of detailed catheterization instructions/procedural indicators or directions for use (DFU) document that may be included in a catheterization package.

FIG. 15A shows a front side of a patient education information sheet/pamphlet that may be included in a catheterization package.

FIG. 15B shows a back side of the patient education information sheet/pamphlet of FIG. 15A.

Figure 1:
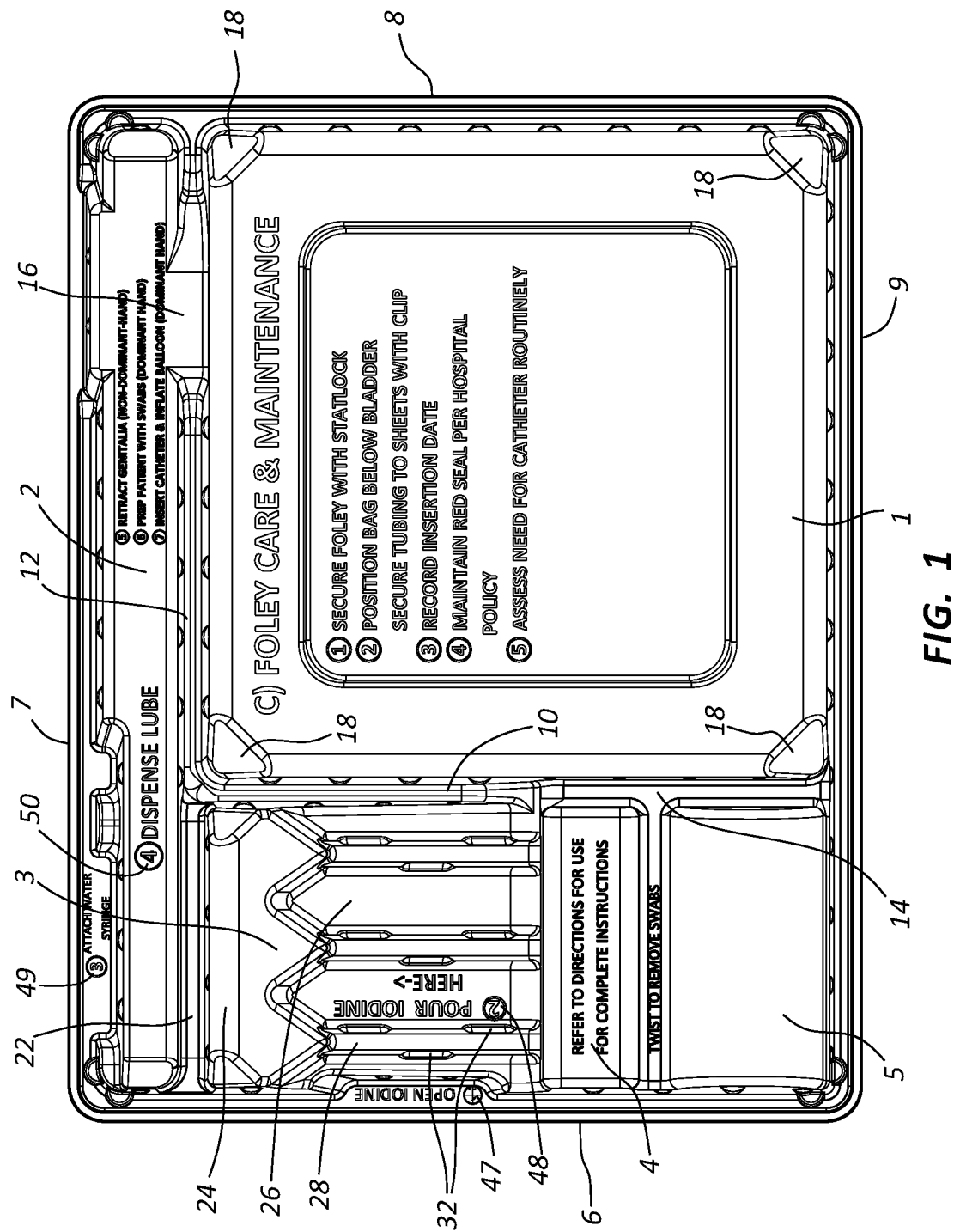
FIG. 1 shows a top view of a medical procedure tray including integrated instructions/procedural indicators in the form of a catheterization tray.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but rather the intention is to cover all modifications, equivalents, and alternatives falling within the spirit and scope of the invention as defined by the appended claims.

DESCRIPTION

The following description and accompanying figures, which describe and show certain embodiments, are made to demonstrate, in a non-limiting manner, several possible configurations of medical procedure packages, medical procedure trays, catheterization packages, catheterization trays, and associated components, assemblies, and systems, etc. and various methods of manufacturing and methods of using these according to various aspects and features of the present disclosure.

Various packages, kits, trays, systems, assemblies, devices, and methods are described herein, including those used in various medical procedures (including, for example, catheterization procedures). While specific embodiments are described herein by way of example, the embodiments and examples described are not intended to be limiting. Accordingly, while aspects of the invention may be described, for example, in terms of catheterization packages, catheterization trays, catheterization procedures, etc. disclosure is not limited to catheterization-related packages, trays, systems/assemblies, procedures, etc. Rather, the inventive principles associated with the embodiments described herein, may be applied to other embodiments and other types of packages, trays, systems/assemblies, devices, methods, etc.

According to various embodiments, the objectives described above and elsewhere herein may be accomplished by providing an improved medical procedure package or kit including a medical procedure tray, for example, with a more intuitive or better organized layout, instructions/procedural indicators included on the tray, etc. For example, an improved catheterization package or kit may be provided to improve ease of use, improve adherence to proper techniques, reduce the likelihood of infection, etc.

In accordance with various embodiments, the medical procedure package may include a medical procedure tray therein. The medical procedure package may also include any other components necessary or helpful to the medical procedure. The medical procedure tray(s) contemplated herein may be a single level tray or have multiple levels. The medical procedure tray(s) may have a variety of shapes and sizes. For example, a medical procedure tray may have a generally or approximately rectangular, square, circular, oval, triangle, hexagonal, polygon, or other shape. As a non-limiting example, a generally rectangular medical procedure tray may have a length in the range from 7 inches to 20 inches, a width in the range from 4 inches to 12 inches, and a height in the range from 1 inch to 4 inches. In one embodiment, a generally rectangular medical procedure tray (e.g., a catheterization tray similar to that shown in FIGS. 1-4) may have a length of approximately 11 inches, a width of approximately 8.5 inches, and a height of approximately 2 inches. In one embodiment, a generally rectangular medical procedure tray (e.g., similar to the tray shown in FIGS. 5, 31A-31C, & 32) may have a length of approximately 14 inches, a width of approximately 8.5 inches, and a height of approximately 2.5 inches.

The medical procedure tray(s) may also include multiple sections having a variety of shapes and sizes, any of which sections can optionally form a compartment. A section of the medical procedure tray can be designated for one or more particular uses (e.g., well for iodine, section for storage, etc.), whereas a compartment can be a section at least partially and up to wholly separated from one or more other sections, compartments, or a combination thereof by a physical feature such as one or more partitions. The partitions can be formed from the medical procedure tray itself (e.g., formed during an injection molding process), and opposing faces of the partitions can be unequal in height if separating compartments from other sections or compartments having bottoms of higher or lower elevations. Partitions can be separately formed from a same material as the medical procedure tray or a different material than the medical procedure tray. The partitions can also be transiently formed from any one or more of the other components necessary or helpful to the medical procedure—until the any one or more of the other components are removed from the medical procedure tray. For example, with respect to components necessary or helpful to catheterization, the one or more partitions can be transiently formed from a specimen or sample container, instructions/procedural indicators, or other components necessary or helpful to catheterization described herein. Like the sections, the compartments can have a variety of shapes and sizes (e.g., the compartments may be of any of the shapes described for the medical procedure tray itself or of other shapes).

In accordance with various embodiments, the medical procedure package may be a catheterization package that includes one or more catheterization trays therein. For example, a catheterization package may include an improved catheterization tray with a more intuitive or better organized layout and/or instructions/procedural indicators included on the tray. While various features are described below in terms of a catheterization package and/or catheterization tray, the features described may also be included in or applied to medical procedure packages and/or trays used for procedures other than catheterization.

The catheterization package may include any components necessary or helpful to catheterization. Some components helpful to catheterization that may be included in the catheterization package include a drainage system, a drainage/collection bag, drainage tubing, a catheter (e.g., a Foley catheter), a drainage outlet, a stabilization device (e.g., C. R. Bard, Inc.'s StatLock® Foley stabilization device), a urine meter, swabs or swabsticks, prepping balls (e.g., absorbent cotton balls), forceps, a specimen or sample container, a label that can be filled out with details regarding the sample and adhered to the specimen or sample container, a packet or container of an antiseptic skin cleanser (e.g., a packet or container of povidone-iodine solution), a packet or container of lubricant (e.g., a syringe of lubricating jelly), a syringe of sterile liquid (e.g., a 10 cc syringe of sterile water for inflating the retention balloon of the Foley catheter), a fenestrated drape to place on patient, an underpad to place under the buttocks of a patient (e.g., a waterproof absorbent underpad), gloves (e.g., a package of rubber gloves, latex gloves, latex-free gloves), a sterile wrap (e.g., a CSR wrap), a belly band (e.g., to hold the sterile wrap in a folded configuration), a perineal care packet, hand sanitizer (e.g., antiseptic gel hand rinse), moist towelettes (e.g., a package of castile soap towelettes), instructions/procedural indicators (e.g., instruction sheet for health care provider and/or instruction pamphlet for patient), a checklist of safety considerations/steps, a patient information chart, an insert sheet, a packaging label, an outer container (e.g., a sealed bag), and/or other components. The components included in the catheterization package may be included in one or more compartments of the catheterization tray, in a separate package or bag (e.g., a package outside the tray), or in a second catheterization tray.

The catheterization tray(s) may be labeled with step-wise instructions/procedural indicators arranged in logical locations on the tray(s). The catheterization tray(s) may have a layout and design that makes the catheterization procedure more intuitive. A single-level catheterization tray having a generally rectangular shape, including multiple compartments of varying shapes, including step-wise instructions/procedural indicators, and having an improved layout is shown, for example, in FIGS. 1-4 and described below. Other similar single-level catheterization trays are shown in FIGS. 5, 31A-31C, & 32 as well.

According to various embodiments and as shown, for example, in FIGS. 1-5, the catheterization tray may include: a main compartment 1; a syringe or catheter compartment 2; a swab compartment 3; a small storage or overflow compartment 4; and a corner storage compartment 5. The tray also includes stiffening ribs (e.g., stiffening ribs 20 shown in FIG. 2; see also stiffening ribs 205 in FIGS. 31A-31C), which help to strengthen the tray and keep the tray from bending when held, e.g., when held by one hand.

Figure 2:
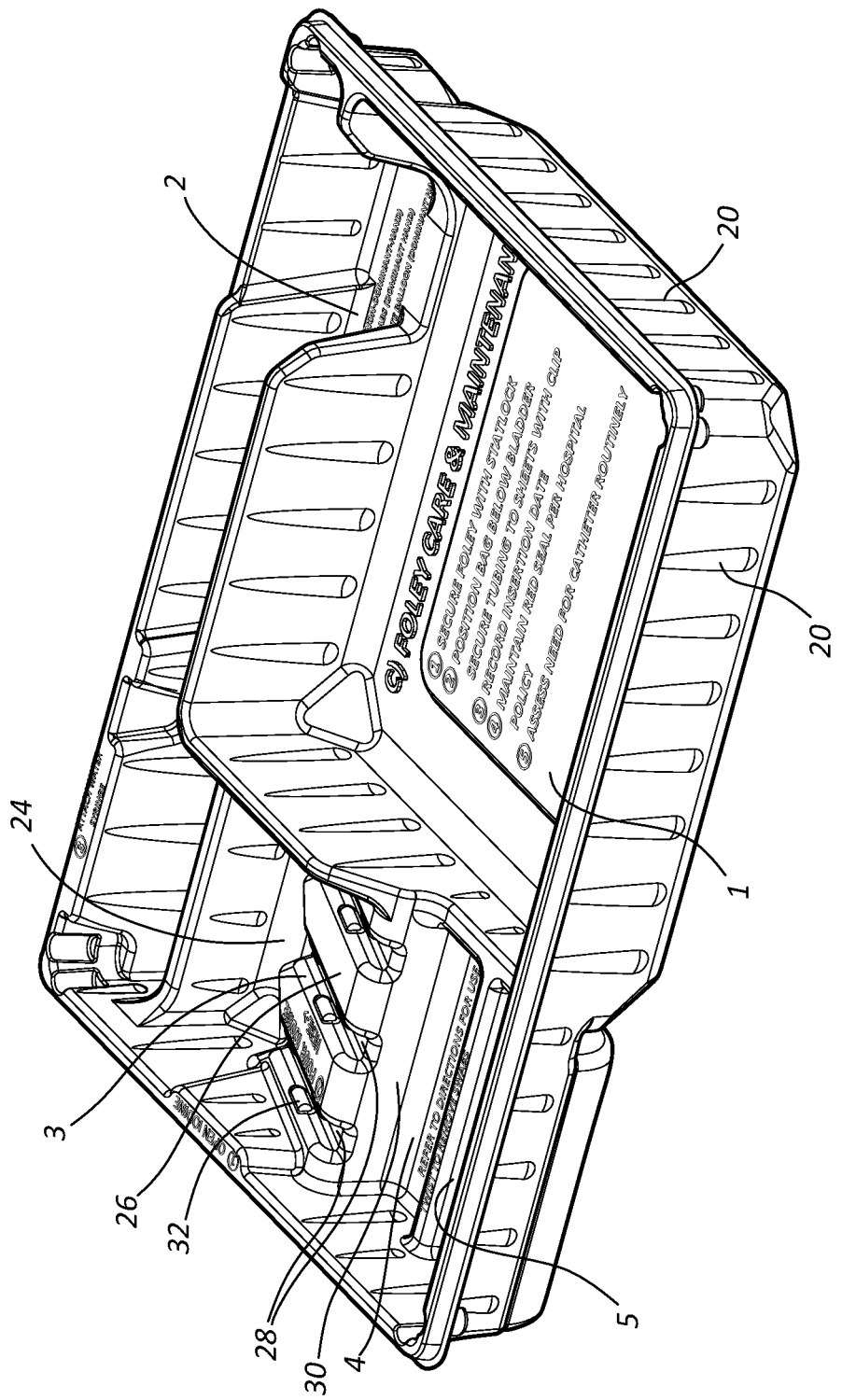
FIG. 2 shows a top, front (or proximal), right perspective view of the medical procedure tray of FIG. 1.
Figure 5:
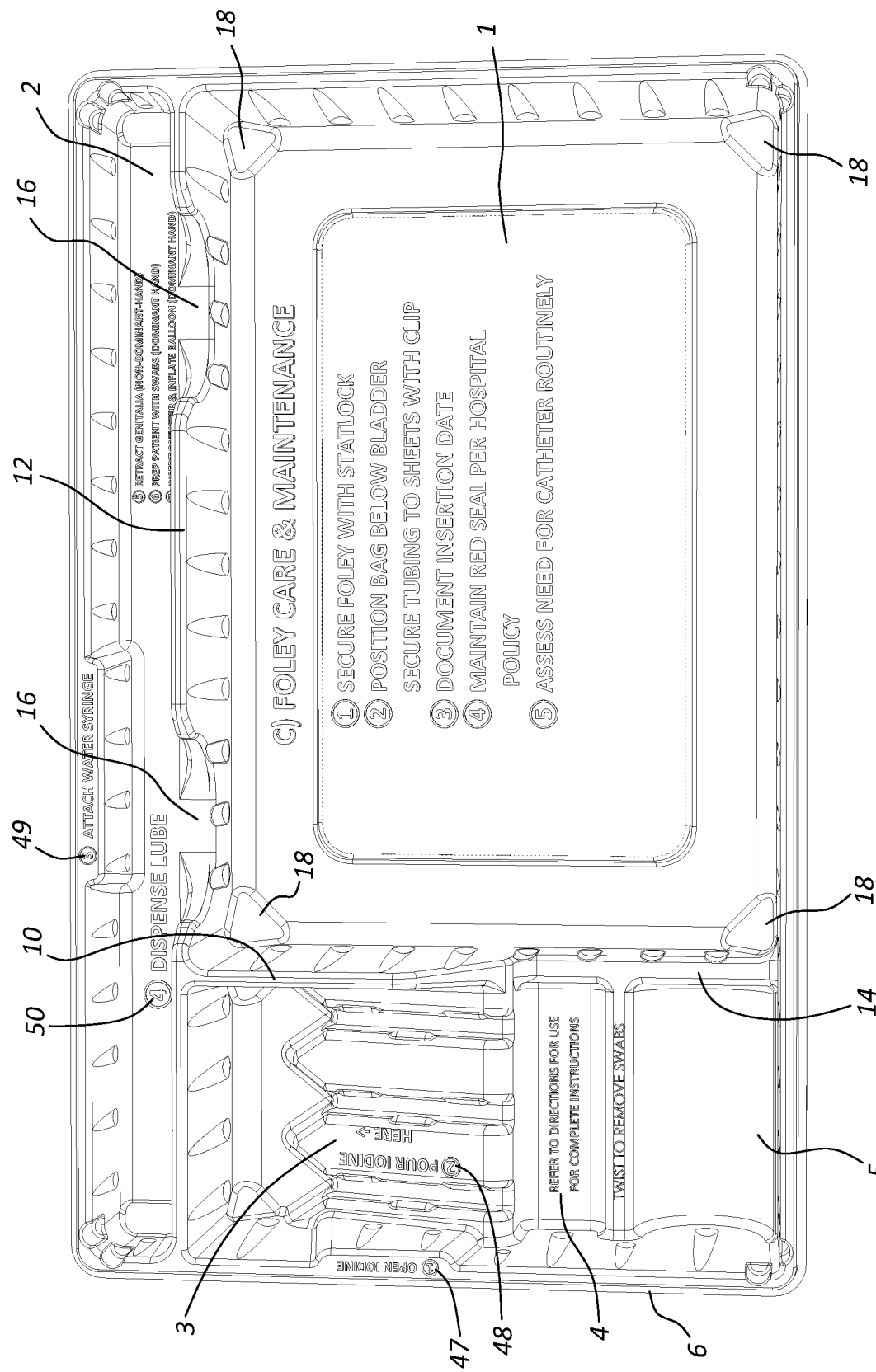
FIG. 5 shows a top view of another medical procedure tray including integrated instructions/procedural indicators in the form of a catheterization tray that is larger than the tray in FIG. 1.

With reference to FIGS. 1, 2, and 5, the main compartment 1 is the largest compartment in the tray and may contain any number of items for the catheterization procedure, for example, a drainage system, a collection bag, a drape, an underpad, an inflation syringe, and/or gloves. A drainage system that may be included in the catheterization package and/or in the main compartment 1 may include, for example, a drainage/collection bag, drainage tubing, a catheter (e.g., a Foley catheter), a drainage outlet, a urine meter, and/or other drainage system components. The drainage system components may be pre-connected and stored in the catheterization package in a pre-connected state, or the drainage system components may be stored as separate components to be assembled/connected later.

The drainage system and tubing included in the catheterization package may be configured and arranged in a way that helps improve drainage of urine through the system and tubing. For example, the tubing or other components of the drainage system may be designed to break up the surface tension of the fluid in order to improve drainage. The drainage tubing may be short to accommodate lower bed profiles or may have an adjustable length for various size beds. The tubing or other drainage system components may have a coating (e.g., a lubricious coating) thereon to facilitate drainage therethrough. Optionally, the tubing or other drainage system components may include a superhydrophobic pattern thereon to facilitate drainage.

Additionally, there are a range of suitable durometers of the tubing or other drainage system components. However, for components that may be coiled in the tray (e.g., drainage tubing and/or the catheter), it is desirable to have a tubing durometer that does not tend to hold a set shape at room temperature. For example, one can experiment with different durometers to ensure that the durometer ultimately used for coiled components does not tend to leave the component in a coiled shape when removed from the tray and put to use. It is desirable, for example, to give the drainage tubing a durometer such that, despite being packaged in the main compartment in a coiled state, when connected to a patient, the drainage tubing does not remain coiled, but tends to straighten out to facilitate drainage. The drainage tubing can be made of polyvinyl chloride (PVC), silicone, latex, Teflon, or another polymer material.

As shown in FIG. 1, sides 8 and 9 of the tray form two orthogonal inner walls of the main compartment 1 and form a corner of the main compartment 1 where the sides 8 and 9 intersect each other. Two additional, interior partitions 10 and 12 separate the main compartment 1 from other compartments. The two interior partitions 10 and 12 include reduced height portions 14 and 16 (with reduced heights compared with the tray's full-height partitions, inner walls, or sides).

Also, the main compartment 1 includes interior fillets 18 at the corners formed between the floor of the main compartment 1 and its inner walls. Such fillets 18 may reinforce the corners of the main compartment 1.

As shown, for example, in FIGS. 1, 2, and 5, the main compartment of the tray may include instructions/procedural indicators and/or other information integrated thereon. For example, the main compartment may include a logo or trademark name written thereon, e.g., "SureStep™ Foley Tray System" and "BARD." The main compartment may also, or alternatively, include instructions/procedural indicators related to the catheterization printed or otherwise included thereon. For example, the main compartment may include instructions/procedural indicators for how to catheterize a patient or instructions/procedural indicators for steps to take after catheterization. Optionally, the main compartment may include instructions/procedural indicators for proper Foley care and maintenance. As shown, for example, in FIGS. 1 and 5, the instructions/procedural indicators integrated on the main compartment may include instructions/procedural indicators stating, "(1) Secure Foley with StatLock®", "(2) position bag below bladder", "secure tubing to sheets with clip", "(3) document insertion date", "(4) maintain red seal per hospital policy", "(5) assess need for catheter routinely." The instructions/procedural indicators or other information may be in upper case letters, in bold, or otherwise called out for greater visibility to ensure the clinician reads the instructions/procedural indicators or other information. Optionally, instructions/procedural indicators may be printed or otherwise included on the main compartment to remind the health care provider/clinician to instruct the patient regarding how to properly care for and maintain the catheter after catheterization. The instructions/procedural indicators may be written to help the health care provider/clinician remember to cover important instructions that should be given to the patient.

The syringe or catheter compartment 2 has an elongated shape and spans approximately an entire length of the tray. Partitions and the inner walls of the tray contribute to form the syringe or catheter compartment 2. Partition 12 spans between opposing inner walls of the tray and separates the syringe or catheter compartment 2 from other compartments—namely, from the main compartment 1 and from the swab compartment 3. The syringe or catheter compartment 2 is sized and shaped to contain one or more syringes (e.g., a syringe of lubricating jelly and a syringe of sterile liquid to inflate the retention balloon) and/or a catheter, such as a Foley catheter. For example, a syringe of lubricating jelly and a syringe of 10 cc sterile water may be packaged in the syringe or catheter compartment 2, but the end user (e.g., a clinician) may remove the syringes at the time of catheterization and place the catheter in the syringe or catheter compartment 2 prior to insertion into a patient (e.g., to facilitate lubrication of the catheter).

A portion of the partition 12 separates the catheter compartment 2 from the main compartment 1. Some of the partition 12 has a full height (e.g., extends as high as the sides of the tray), but the partition 12 also includes reduced height portions 16 and 22 (which have a reduced height relative to the full height of the partition 12, inner walls, or sides of the tray). Reduced height portion 16 of the partition 12 may act as a break or opening in the partition, which may place the syringe or catheter compartment 2 in fluid communication with the main compartment 1 and vice versa. Along reduced height portion 16, the partition 12 may form a small step between the syringe or catheter compartment 2 and the main compartment 1, e.g., as shown in FIGS. 2 and 6 (see also FIGS. 31A-31C). The step may also be formed by the main compartment 1 having a lower/deeper floor than the floor of the syringe or catheter compartment 2, e.g., as shown in FIGS. 2 and 6 (see also FIGS. 31A-31C).

In FIGS. 1 and 2, another reduced height portion of the partition, i.e., reduced height portion 22, separates the syringe or catheter compartment 2 from the swab compartment 3. Reduced height portion 22 of the partition 12 has a partial or reduced height relative to the full height of the inner walls or the sides of the tray. FIG. 5 shows an alternate arrangement of reduced height portions 16, wherein both reduced height portions 16 are located along the partition between the syringe or catheter compartment and the main compartment (i.e., there is no reduced height portion 22 between the syringe or catheter compartment and the swab compartment). Other arrangements and configurations are also possible. If syringes are packaged or included in syringe or catheter compartment 2, the reduced height portions (e.g., reduced height portions 16 and 22) help facilitate easy removal of the syringes from the syringe or catheter compartment 2 by providing more open space for the end user to reach into the tray and grasp onto the syringes. This makes removal of the syringes easier than if the partition 12 did not have any reduced height portions and the clinician had to try to grasp the syringes within a narrower region.

As shown, for example, in FIGS. 1 and 5, the syringe or catheter compartment of the tray may also include instructions/procedural indicators and/or other information integrated thereon. For example, the syringe or catheter compartment may optionally include instructions/procedural indicators related to the catheterization written thereon. As shown in FIGS. 1 and 5, the instructions/procedural indicators integrated on the syringe or catheter compartment may include instructions/procedural indicators stating "Dispense & Lube Foley here" (alternatively, this instruction may simply say "Lube Foley," "Dispense Lube," or something similar), "retract genitalia (non-dominant hand)", "prep patient with swabs (dominant hand)", "insert catheter & inflate balloon (dominant hand)." As shown in FIGS. 1 and 5 and as stated above, the instructions/procedural indicators may inform the health care provider which hand to use for a given step, e.g., dominant or non-dominant hand. The instructions/procedural indicators or other information may be in upper case letters, in bold, or otherwise called out for greater visibility to ensure the clinician reads the instructions/procedural indicators or other information.

Note that the sides of the catheterization tray may also include instructions/procedural indicators or other information thereon. For example, as shown in FIGS. 1, 2, and 5, side 6 may include a reduced height portion with an instruction/procedural indicator 47 to "open iodine," while side 7 may include an instruction/procedural indicator 49 to "attach water syringe." The instructions/procedural indicators or other information may be in upper case letters, in bold, or otherwise called out for greater visibility to ensure the clinician reads the instructions/procedural indicators or other information.

Figure 4:
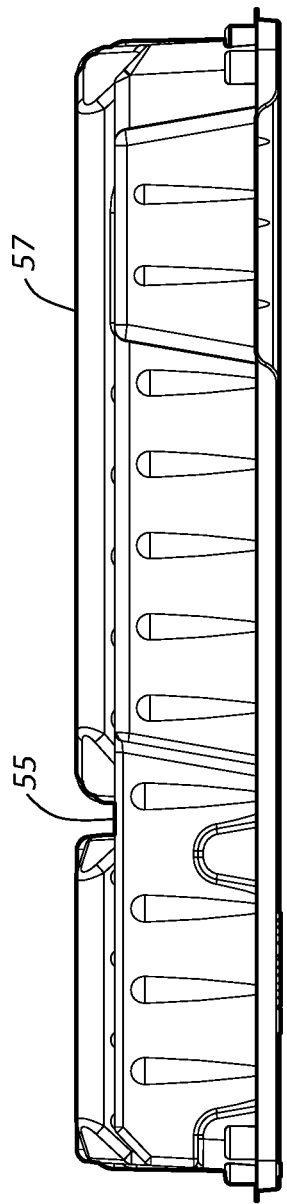
FIG. 4 shows a back (or distal) side elevation view of the medical procedure tray of FIG. 1.
Figure 3:
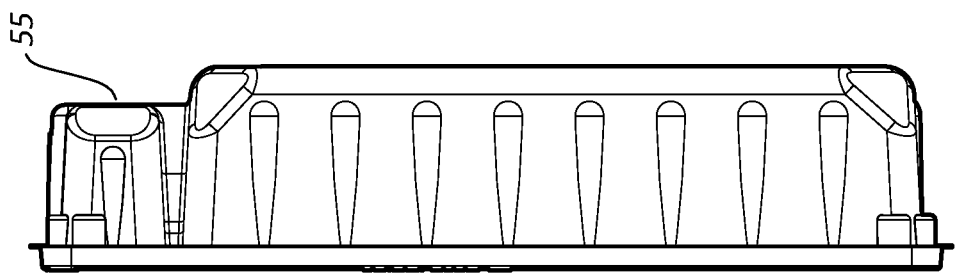
FIG. 3 shows a right side elevation view of the medical procedure tray of FIG. 1.

As shown in FIGS. 3 and 4, the base 55 of the syringe or catheter compartment 2 may be offset from the bases of all other compartments. In other words, the base 55 of the syringe or catheter compartment 2 may be not as deep or separated from the top of the tray as, for example, the base 57 of the main compartment 1. As the base 55 is offset from the bases of the other compartments, the bottom/floor of the syringe or catheter compartment is offset from bottoms/floors of the other compartments, including being offset from the bottom/floor of the main compartment 1.

The swab compartment 3 spans along a portion of the tray's inner wall along side 6 of the tray; that portion of the inner wall forms a side of the swab compartment 3. The swab compartment 3 may contain various items, for example, swabs or swabsticks and one or more antiseptics such as iodine (e.g., an iodophor such as povidone-iodine, tincture of iodine, aqueous iodine, etc.). Portions of partition 10 and partition 12 extend along two other sides of the swab compartment 3 forming two other sides of the swab compartment 3, and separate the swab compartment 3 from the main compartment 1 and the syringe or catheter compartment 2, respectively. Also, the small storage or overflow compartment 4 extends along a fourth side of the swab compartment 3. In one embodiment as shown, for example, in FIGS. 1 and 2, the partition 10 has a full height where it separates the swab compartment 3 from the main compartment 1, while the partition 12 has a reduced height (i.e., at reduced height portion 22) that separates the swab compartment 3 from the syringe or catheter compartment 2. In one embodiment as shown, for example, in FIG. 5, the partition 10 and the partition 12 both have a full height whether they separate the swab compartment 3 from the main compartment 1 and the syringe or catheter compartment 2.

The swab compartment 3 has an angled bottom/floor that spans between the small storage or overflow compartment 4 and the syringe or catheter compartment 2 and has a downward slope therebetween (i.e., the bottom/floor of the swab compartment 3 near the catheter compartment 2 is lower than near the storage compartment 4). As such, fluid poured into the swab compartment may flow in a direction toward the catheter compartment 2 and pool in the lowest/deepest portion or well 24 of the swab compartment near the partition 12 (e.g., adjacent reduced height portion 22 in FIGS. 1 and 2) where it separates the swab compartment 3 from the catheter compartment 2. Fillets may be included in the corners of the swab compartment 3 similar to fillets 18 in the main compartment 1, e.g., as shown in FIGS. 1 and 2.

Figure 8:
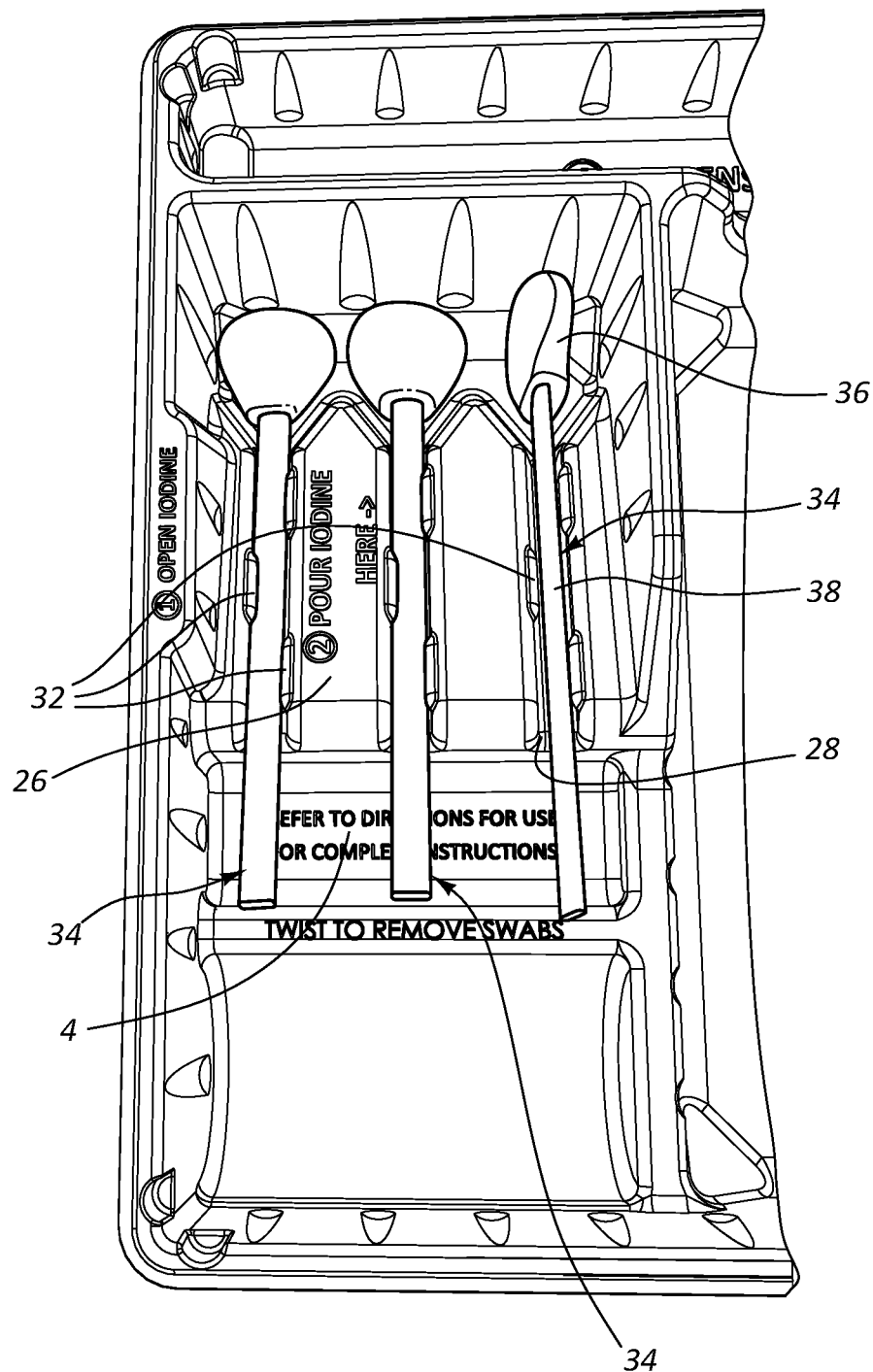
FIG. 8 shows a top view of a swab compartment and small storage or overflow compartment of a catheterization tray including swabs or swabsticks similar to the swab or swabstick shown in FIGS. 7A-7C, wherein one swab or swabstick is rotated approximately 90° to release it from the securement features of the swab compartment.

FIG. 8 shows a larger view of the swab compartment 3 and the adjacent small storage or overflow compartment 4 with swabs or swabsticks contained in the swab compartment 3. Near the small storage or overflow compartment 4, the bottom/floor of the swab compartment 3 may be supported by another partition 30 (shown on FIG. 2) that separates the small storage or overflow compartment 4 from the swab compartment 3. Also, the partition 30 may extend upward (from the bottom/floor of the small storage or overflow compartment 4) only to the bottom/floor of the swab compartment 3, leaving the bottom/floor of the swab compartment 3 unobstructed near the small storage or overflow compartment 4 (as such, swabs or swab sticks with a longer stick/stem may extend over a portion of the small storage or overflow compartment 4 from the bottom/floor of swab compartment 3 as shown, for example, in FIG. 8). This design or arrangement also allows small storage or overflow compartment 4 to act as an overflow well in case too much fluid/iodine is poured into swab compartment 3.

The swab compartment 3 includes one or more channels 28 extending at least partially along the region between the small storage or overflow compartment 4 and well 24 located at a bottom/floor of the swab compartment 3. On a side of the swab compartment 3 near the catheter compartment 2, the channels 28 extend to and are in fluid communication with the lowest/deepest portion of the well 24 adjacent the partition 12, such that liquid poured into the channel(s) 28 can flow downward through the channel(s) 28 along the downward slope and pool in the lowest/deepest portion of the well 24. The channel(s) 28 may be designed to hold an elongated device (e.g., swabs or swabsticks) and each channel 28 may be separated by one or more barriers 26 to help space the elongate devices (e.g., swabs or swabsticks) apart. Channel(s) 28 may also include undercutting or snap-in features 32 (e.g., snap-in tabs) that may help secure elongated devices, such as swabs, swabbing sticks, or swabsticks in the channel(s) 28.

As shown, for example, in FIGS. 1, 5, and 8, the swab compartment of the tray may also include instructions/procedural indicators and/or other information integrated thereon. For example, the swab compartment (e.g., on one of barriers 26) may optionally include instructions/procedural indicators related to the catheterization printed or otherwise included thereon. As shown in FIGS. 1, 5, and 8, the instructions/procedural indicators integrated on the swab compartment may include an instruction/procedural indicator stating "pour iodine here." The instructions/procedural indicators or other information may be in upper case letters, in bold, or otherwise called out for greater visibility to ensure the clinician reads the instructions/procedural indicators or other information.

One or more swabs or swabsticks (e.g., swab or swabstick 34 shown in FIGS. 6A-8) may be packaged in the swab compartment 3 and held in channels 28 (e.g., as shown in FIG. 8). The swabs or swabsticks may be specially designed to fit in swab compartment 3 and to be held in channels 28. Swab compartment 3 may also include iodine or povidone-iodine solution. The iodine or povidone-iodine solution may be packaged in its own container, packet, or syringe in the swab compartment 3, e.g., povidone-iodine packet 52 shown in FIG. 26. Alternatively, the iodine or povidone-iodine solution may be stored and/or sealed in swab compartment 3 in direct contact with the swab(s) or swabstick(s) 34 (e.g., packaged/sealed such that it is in contact with a portion of the bottom/floor of swab compartment 3).

Figure 6A:
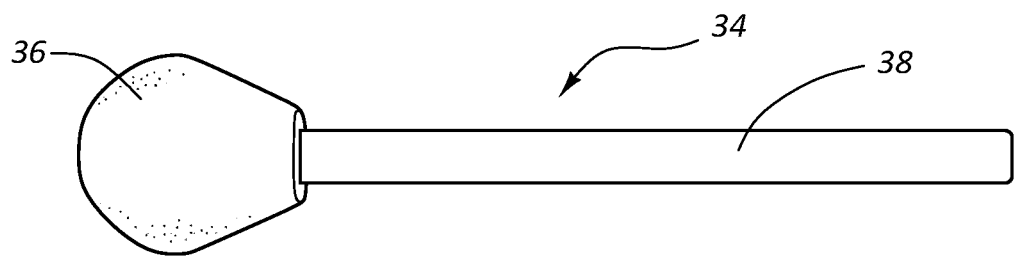
FIG. 6A shows a top view of a swab or swabstick that may be included in a catheterization package and/or tray.
Figure 6B:
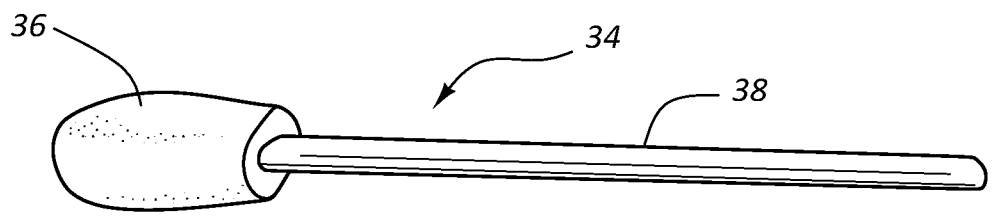
FIG. 6B shows a side perspective view of the swab or swabstick in FIG. 6A.
Figure 6C:
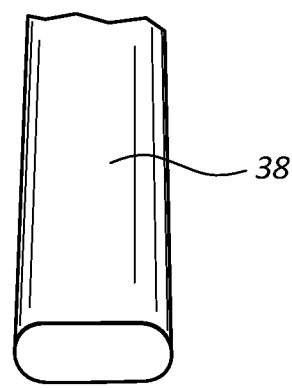
FIG. 6C shows an end view of the swab or swab stick in FIG. 6A to show the cross-sectional shape of the elongate member or stick.
Figure 7A:
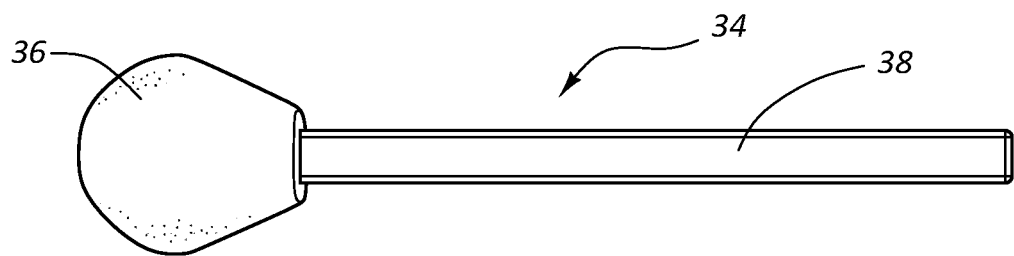
FIG. 7A shows a top view of a swab or swabstick that may be included in a catheterization package and/or tray.
Figure 7B:
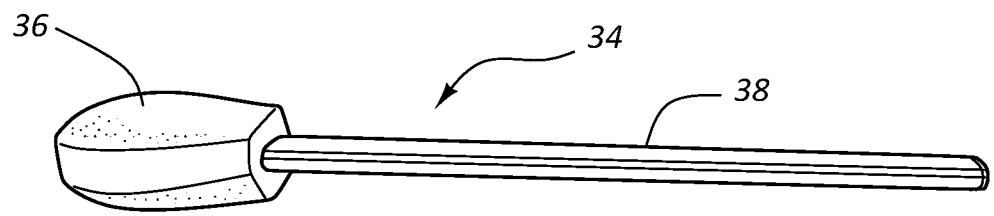
FIG. 7B shows a side perspective view of the swab or swabstick in FIG. 7A.
Figure 7C:
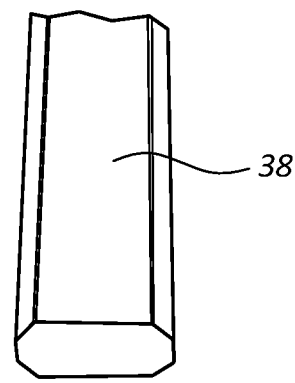
FIG. 7C shows an end view of the swab or swabstick in FIG. 7A to show the cross-sectional shape of the elongate member or stick, the cross-sectional shape being different from that shown in FIG. 6C.

FIGS. 6A-6C show one embodiment of swab or swabstick 34 with an elongate member or stick/stem 38 having more rounded sides (e.g., in cross-section) than the swab or swabstick 34 shown in FIGS. 7A-7C. FIGS. 7A-7C show one embodiment of swab or swabstick 34 with an elongate member or stick/stem 38 having less rounded or more angular sides than the swab or swabstick 34 shown in FIGS. 6A-6C. Swab or swabstick 34, as shown in FIGS. 6A-7C, is representative of other possible swabs or swabsticks that may be included. Swab or swabstick 34 includes an absorbent head 36 and an elongate member or stick/stem 38. Absorbent head 36 is designed to allow for greater saturation in cleansing solution (e.g., in iodine or povidone-iodine solution) and for greater contact with the surface area of the region to be cleansed. Absorbent head 36 may be formed from various materials, including foam, rayon (e.g., puffs of rayon or a spiral of rayon), cotton, other materials, and/or a combination of one or more of these materials. To improve saturation of the absorbent head, the absorbent head 36 is desirably made of a material that readily absorbs and distributes the cleansing solution. Any material that absorbs a significant percentage of its weight in cleansing solution is desirable for use in the absorbent head, especially if it also releases a large percentage of absorbed cleansing solution, i.e., it is desirable to use a material that absorbs a large amount of cleaning solution and also releases a large amount of cleaning solution when used on the patient for cleaning. It has been found that forming the absorbent head 36 of foam (as opposed to rayon or other materials) provides the absorbent head 36 with improved absorption of and saturation with cleansing solution. Further, a foam absorbent head readily releases a large amount of the cleansing solution when put in contact with the region of the patient to be cleansed and when compressed slightly against the region being cleansed. This ready release of cleansing solution makes cleansing the region of the patient easier and allows the end user to be more gentle when cleansing the patient. If absorbent head 36 is made entirely or partially of foam, the foam may be open-cell foam, closed-cell foam, polyurethane foam, high density foam, latex foam, honey gold foam, or other types of foam. The absorbent head may be heated such that it bonds to the elongate member or stick (e.g., the foam may be heated to bond to the stick), or other means of attachment may be used, e.g., using an adhesive.

Preferably the foam or other material(s) selected for the absorbent head do not degrade or at least resist degrading when in contact with the cleansing solution. In one embodiment, the swabs or swabsticks may be stored in contact with iodine or a povidone-iodine solution, so they are already saturated when they are first accessed in the catheterization package. For example, a seal may be placed in or over swab compartment 3 that holds a cleansing solution in contact with the absorbent head(s) of the swab(s) or swabstick(s) while preventing leaks until the seal is removed. When packaged and stored in contact with the cleansing solution, it is vital that the absorbent head not degrade over time. Honey gold foam, for example, is sufficiently resistant to degradation when in contact with an iodine or povidone-iodine solution.

Absorbent head 36 may be of a variety of sizes and shapes. Preferably, the foam is shaped in such a way as to provide for greater contact with the surface area of the region to be cleansed. For example, the absorbent head 36 may be shaped such that the distal end or distal region (e.g., regions that come into contact with the patient), are substantially larger than regions that are less likely to come into contact with the patient (e.g., the proximal end or where the absorbent head 36 attaches to the elongate member or stick 38). This provides more surface area in the patient-contacting end of the absorbent head and makes cleansing the patient quicker and easier. Further, with the distal region of the absorbent head being larger, the majority of the iodine is absorbed into the area that contacts the patient (in contrast, when the largest region of the absorbent head is not at or near the distal end, much of the iodine is wastefully absorbed into a location that does not contact or cleanse the patient). The absorbent head 36 may be shaped as shown in FIGS. 6A-7B and may be wider than it is thick. The absorbent head 36 could also be shaped to be generally or approximately circular, rectangular, or trapezoidal. Optionally, the shape of absorbent head 36 may be generally or approximately conical, pyramidal, tear drop, ovoid, or triangular in shape (with the larger base end positioned at the distal tip of the swab or swabstick), or may be another shape. If generally pyramidal in shape, the base of the pyramidal shape may be generally triangular, square, pentagonal, hexagonal, etc. Even if otherwise generally conical, pyramidal, or another shape, the edges of the absorbent head at the distal end may be curved or tapered (e.g., as the distal edges are curved in FIGS. 6A-7B). Further, the distal end of the elongate member or stick 38 may also be curved (e.g., the distal end may be semi-circular rather than flat across the top or distal-most edge), as curves are less likely to harm patient when cleansing with a swab or swabstick.

In one embodiment, the length of the absorbent head may be between 0.5 and 2 inches (in one embodiment, the length may be approximately 1 inch), the width of the absorbent head at its widest may be between 0.5 and 2 inches (in one embodiment, the width at its widest may be approximately 1 inch) and the width of the absorbent head at its narrowest may be between 0.1 and 1 inches (in one embodiment, the width at its narrowest may be approximately ½ of an inch). Further, if the absorbent head is not generally conical or pyramidal in shape (i.e., such that its width and thickness are the same all around), it may have a thickness less than its width, e.g., a thickness between 0.1 and 1 inches (in one embodiment, the thickness may be approximately ⅜ of an inch).

In one embodiment, the elongate member or stick 38 may have a length between 2 and 7 inches (e.g., the elongate member or stick 38 may have a length between 3.5 and 4.5 inches, or a length of approximately 4.25 inches). The length of penetration of the stick 38 into the absorbent head 36 (i.e., the length the stick 38 that extends distally beyond the proximal end of the absorbent head) may be between 0.25 inches and 1 inch (e.g., the length of penetration may be approximately 0.5 inches). It is preferable to ensure that the length of penetration is within a good range relative to the overall length of the absorbent head. If the stick 38 extends too far into the absorbent head 36, the patient's skin may be too easily damaged by the stick 38 (e.g., it may be more likely to scrape against the patient during cleansing, and may not be padded by enough foam). Whereas, if the stick 38 does not extend far enough into the absorbent head 36, the absorbent head 36 will lack structure and flop around (especially if saturated with liquid), which makes it harder for the end user to guide the absorbent head of the swab or swabstick and effectively cleanse the patient. Ideally, the length of penetration of the stick 38 will extend between 35 and 70% of the length of the absorbent head 36 (e.g., the length of penetration may be about 50% of the length of the absorbent head). The elongate member or stick 38 may be formed from various materials, including a plastic or polymer material.

The elongate member or stick 38 may have a variety of different cross-sectional sizes and shapes. For example, the swab or swab stick may be biased to be relatively flat or have a generally rectangular cross-section (or a rectangular-like cross-section but with rounded edges as shown, for example in FIG. 6C, or with cut off edges as shown, for example, in FIG. 7C), so it is easier to hold. The elongate member or stick 38 shown in FIGS. 6A-6C has rounded edges, but has a roughly rectangular shape otherwise. This is a shape that is easier to hold and manipulate while cleaning a patient than a stick with a circular cross-section. Further, this and similar cross-sectional shapes for the elongate member or stick 38 make it possible for the swabs or swabsticks to snap into the tray or be held under features 32 to prevent movement of the swabs or swabsticks during shipping or before use. To remove a swab or swabstick of this cross-section, one can simply twist the elongate member or stick 38 in a clockwise or counter clockwise direction and the features 32 easily release the swab or swabstick for use. For example, FIG. 8 shows two swabs or swabsticks that are snapped or held in place under the features 32, and also shows one swab or swabstick that has been twisted such that the features 32 no longer hold the swabstick or prevent its removal. This makes the swabs or swabsticks very secure in the swab compartment 3 during shipping and before use, but also makes removal of the swabs or swabsticks at the time of catheterization very simple and easy.

In one embodiment, if the elongate member or stick is of a generally flattened (e.g., generally rectangular) shape, the width or diameter of the elongate member or stick 38 may be between approximately ⅛ of an inch and ¾ of an inch (e.g., the width may be about ¼ of an inch), whereas the thickness may be between 1/16 of an inch and ½ of an inch (e.g., the thickness may be approximately ⅛ of an inch). If the elongate member or stick is of a generally circular cross-section or is generally cylindrical in shape, the diameter of the elongate member or stick 38 may be between ⅛ of an inch and ½ of an inch (e.g., the diameter may be about ¼ of an inch).

The swabs or swabsticks are loaded into the tray and held in such a way that the absorbent head 36 is in the lowest/deepest portion or well 24 of the bottom of the swab compartment 3 such that they are exposed to the iodine that pools in the lowest/deepest portion or well 24 of the bottom of the swab compartment 3 and easily saturate with the iodine or povidone-iodine solution. However, the elongate member or stick 38 may be loaded into the tray and held in such a way that the elongate member or stick 38 is not itself exposed to the iodine or povidone-iodine solution.

The small storage or overflow compartment 4 spans along a portion of the tray's side 6, which forms an inner wall of the tray and a side of the small storage or overflow compartment 4. Three other sides of the small storage or overflow compartment 4 are formed by partial-height partitions that separate the small storage or overflow compartment 4 from the main compartment 1, swab compartment 3, and corner compartment 5. These compartments may surround the small storage or overflow compartment 4 on three sides thereof. The small storage or overflow compartment 4 may act as an overflow well to collect any fluid that might overflow from the swab compartment. Optionally, the small storage or overflow compartment 4 may store or hold one or more items useful for catheterization.

As shown, for example, in FIGS. 1 and 5, the small storage or overflow compartment of the tray may also include instructions/procedural indicators and/or other information integrated thereon. For example, the small storage or overflow compartment may optionally include instructions/ procedural indicators related to the catheterization printed or otherwise included thereon. As shown in FIGS. 1 and 5, the information integrated on the small storage or overflow compartment may include a reminder that the health care provider/clinician should "refer to directions for use for complete instructions." The instructions/procedural indicators or other information may be in upper case letters, in bold, or otherwise called out for greater visibility to ensure the clinician reads the instructions/procedural indicators or other information.

The corner storage compartment 5 spans along portions of the tray's side 6 and side 9, which form sides and a corner of the corner storage compartment 5. Two other sides of the corner storage compartment 5 may be formed by partial-height partitions that separate the corner storage compartment 5 from the main compartment 1 (e.g., reduced height portion 14) and small storage or overflow compartment 4. These compartments surround the corner storage compartment 5 on two sides thereof.

The bottom/floor of the corner storage compartment 5 may be non-planar; namely, the bottom/floor may have a non-planar, rounded, or partially cylindrical shape. This shape may be particularly useful for holding a specimen or sample container. Corner storage compartment may store or hold various implements useful for catheterization. For example, corner storage compartment may hold a label that can be filled out by a clinician on a first side and adhered to a specimen or sample container on a second side. The second side may already include an adhesive thereon; the adhesive may be covered by a removable cover sheet that may be removed at the time of adhering. The corner storage compartment may also include a specimen or sample container 54.

In one embodiment, at least some of the compartments may be sealed in a manner that prevents contamination thereof. In one embodiment, at least one of the compartments may be unsealed independently of at least one other compartment. For example, a user may first unseal the main compartment, leaving other compartments sealed. After using items contained in the main compartment, the user may unseal another compartment and use items contained in that compartment.

In one embodiment, a user may unseal the swab compartment 3 prior to unsealing the syringe or catheter compartment 2 or the main compartment 1. The user may pour iodine or another antiseptic solution into the swab compartment and may use the swab compartment for applying the antiseptic solution onto swabs, and then use the iodine soaked swabs to cleanse the patient. A user may then unseal the syringe or catheter compartment 2 and dispense lubricant therein prior to unsealing the main compartment 1. A user may then unseal the main compartment 1 to access the catheter. The shape and size of the catheter compartment facilitate lubrication of the catheter (e.g., a tip of the catheter can rotate within the elongated shape of the catheter compartment and collect lubricant on its surface during the rotation). The catheter may be lubricated in the syringe or catheter compartment 2 and then inserted into the patient's urethra.

According to various embodiments, and as shown in FIGS. 1, 2 and 5, and as discussed above, the tray may have ordered, stepwise instructions/procedural indicators thereon for a suitable or preferred catheter insertion technique.

Other aspects or features of the catheterization package(s) and catheterization tray(s) are also described below in the context of non-limiting procedures or methods of using the catheterization package and catheterization tray, and in the context of methods of manufacturing or packaging a catheterization package. The aspects or features described below may be incorporated into the various embodiments already discussed above. The arrangement of components and how they are accessed is part of the overall intuitive design of the catheterization package, i.e., components and features are arranged in a logical manner that flows from step to step to make the catheterization procedure more intuitive and make completing the procedure easier and/or quicker. Step-by-step ordering of the components in the catheterization package helps a user/clinician to logically know what step comes next. For example, a first item may be revealed in the package, then once the first item is used, a second item that was underneath the first item is revealed, the second item being next logical item for use in the catheterization procedure. Once the second item is used, a third item that was underneath the second item may be revealed, the third item being the next logical item for use in the catheterization procedure, and so on.

The catheterization package(s) and catheterization tray(s) described herein may be used in many different ways. A non-limiting method of use is described below. However, clinicians may vary the steps or procedures described herein, may reorder the steps, may perform additional steps beyond those described, and/or may omit certain steps as circumstances and a patient's unique needs may require. Further, the description below can be considered a description of an overall procedure with many steps or can be considered a series of individual methods or procedures each including only a subset of the steps described.

Figure 9:
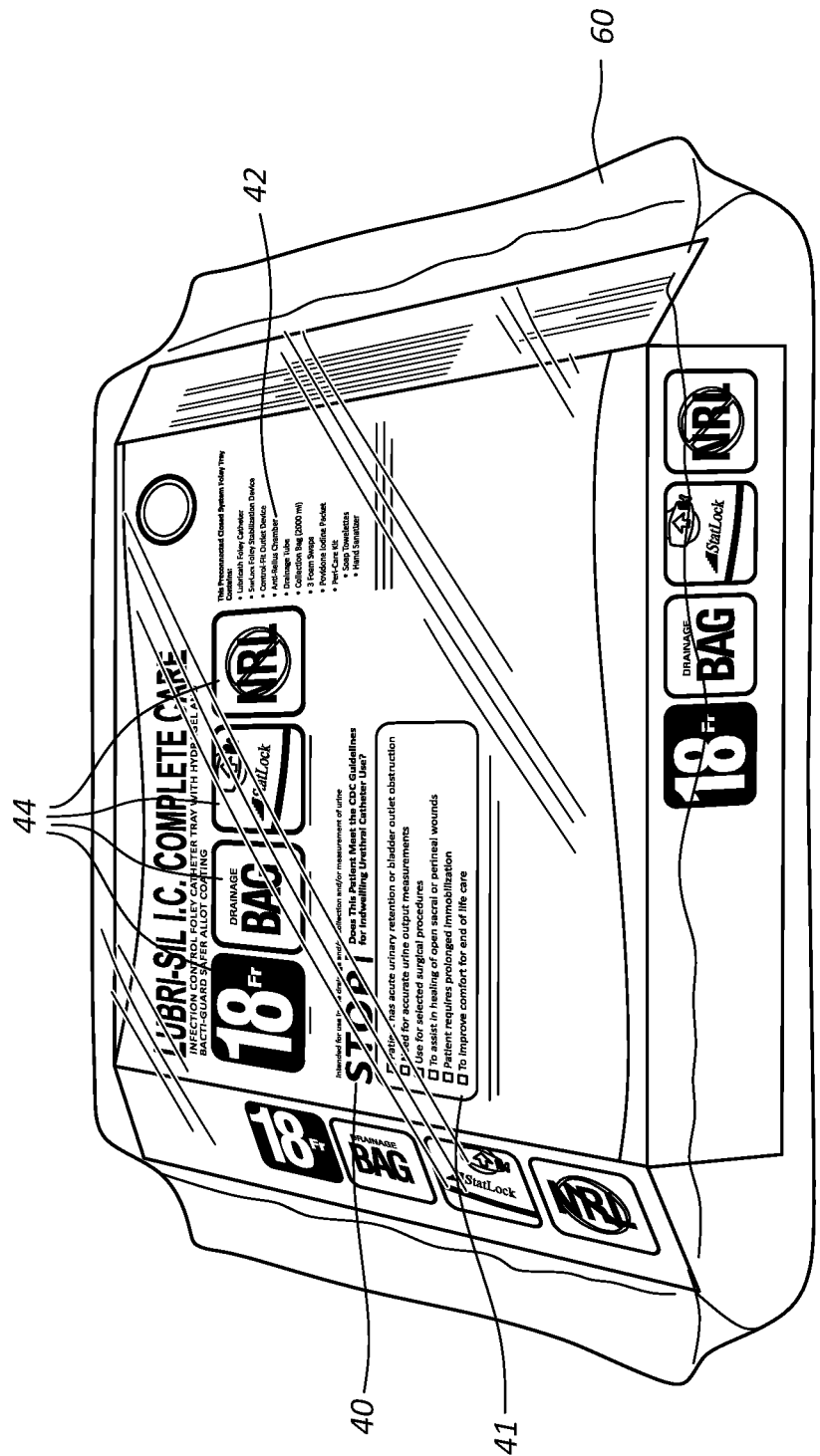
FIG. 9 shows a top view of a catheterization package sealed in a sealed bag and having a packaging label with information squares on a top and two sides thereof, the sides providing for easy viewing even if the catheterization package were in a stack of other catheterization packages.
Figure 10:
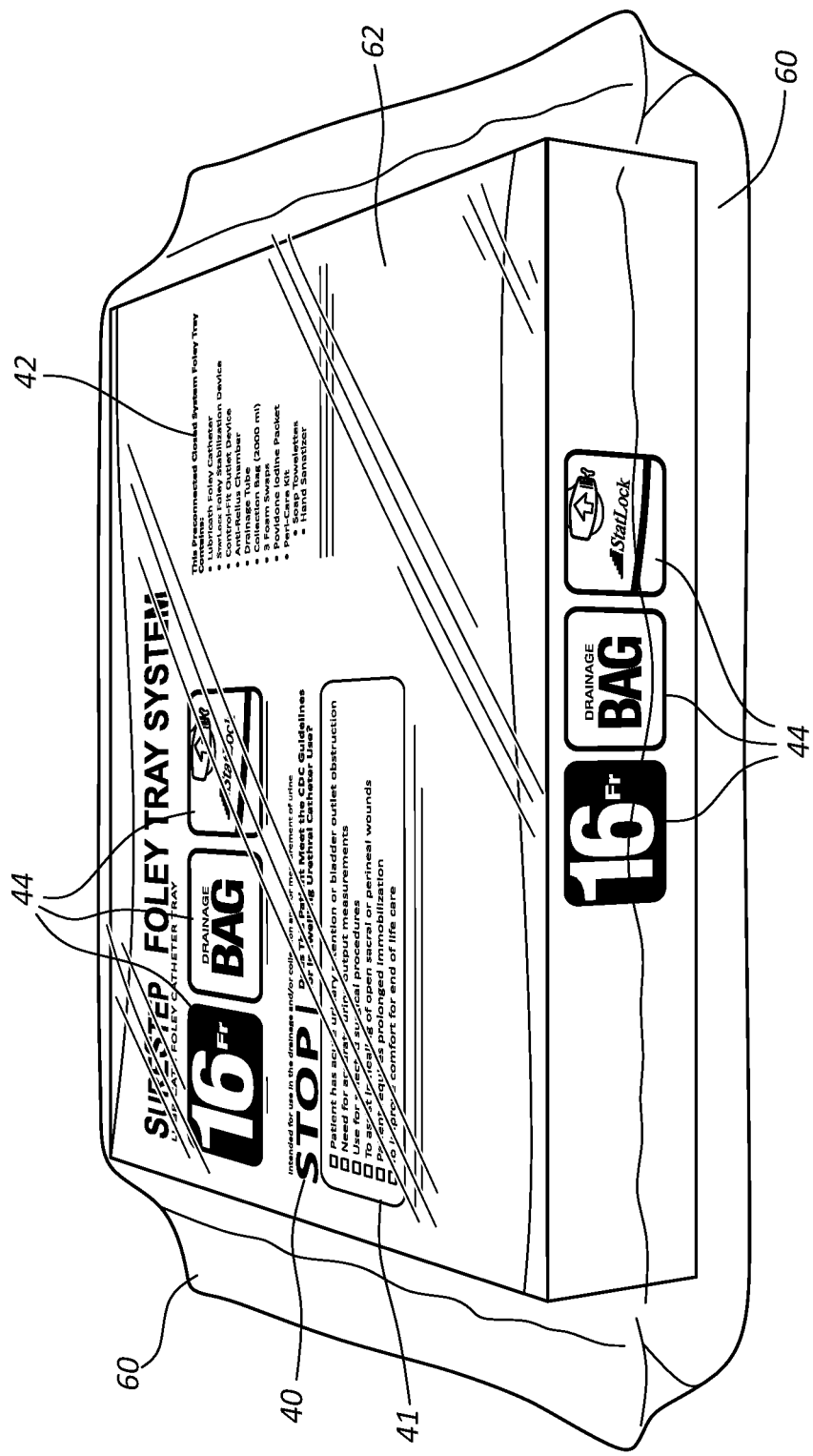
FIG. 10 shows a top, front perspective view of another catheterization package (different from that shown in FIG. 9) sealed in a sealed bag and having a packaging label with information squares on a top and two sides thereof (one side of which is visible), the sides providing for easy viewing even if the catheterization package were in a stack of other catheterization packages.
Figure 11:
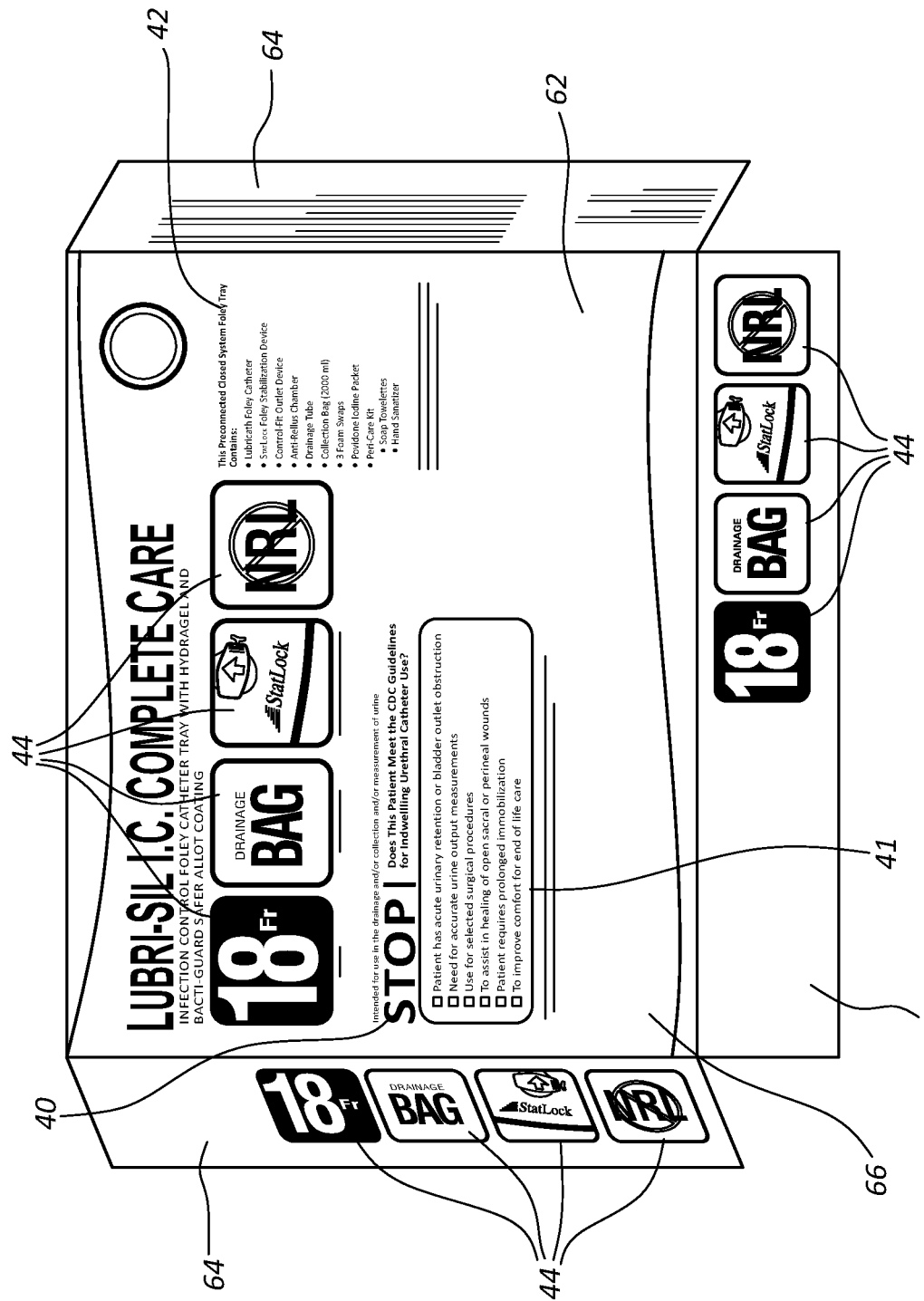
FIG. 11 shows a top view of the catheterization package of FIG. 9 outside of the sealed bag, but still having the same packaging label thereon.
Figure 12:
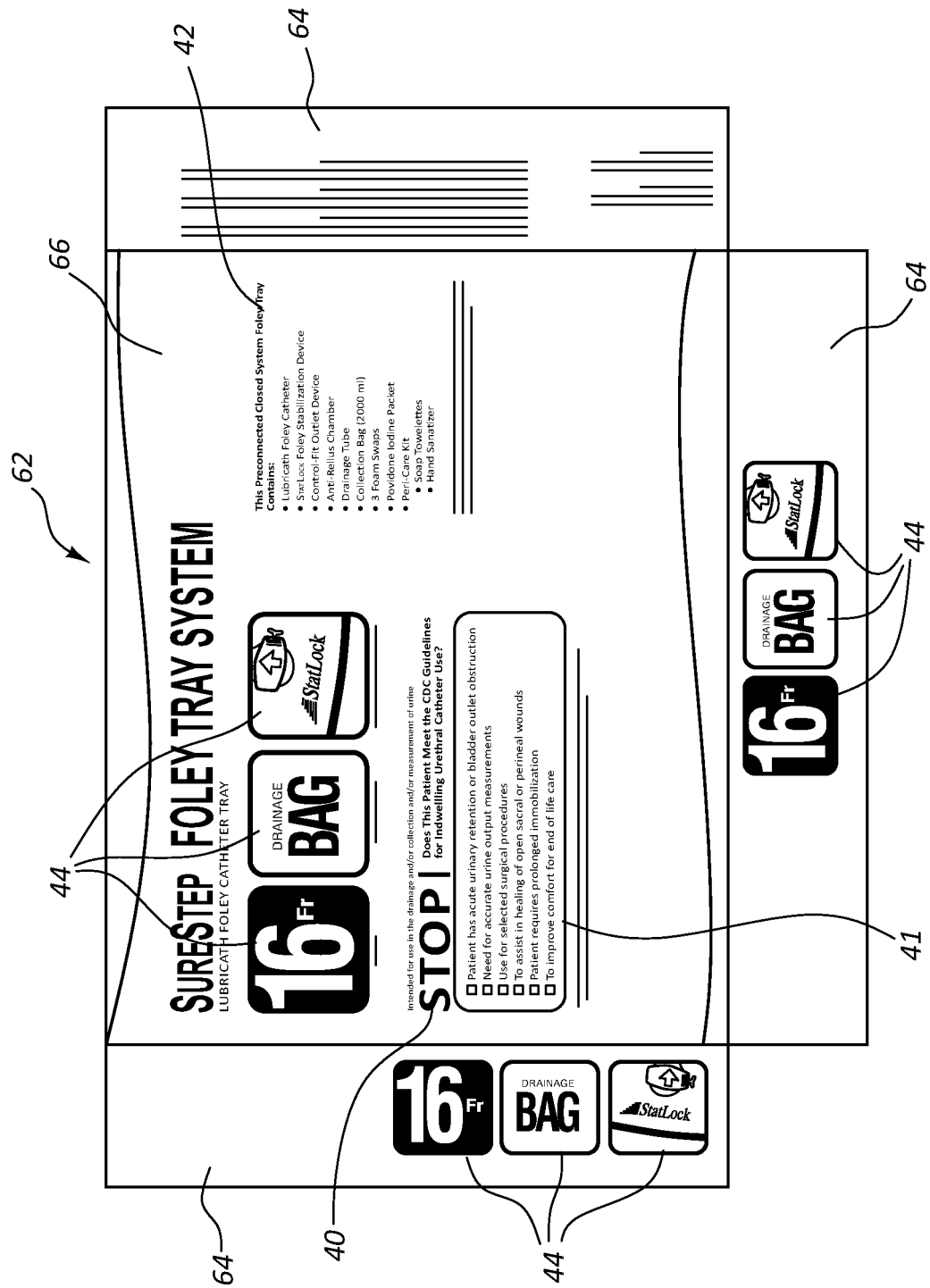
FIG. 12 shows a top, flattened view of the packaging label of the catheterization package of FIG. 10 including lines added to show where the sides may be folded when placed over other components of a catheterization package prior to sealing the catheterization package in a sealed bag.

First, a catheterization package as shown, for example, in FIGS. 9 and 10 may be provided (e.g., a health care provider/clinician may obtain or select the catheterization package from shelf or through a purchase, or may place the catheterization package in the hospital room where the patient is waiting for catheterization.) As can be seen in FIGS. 9 and 10, the catheterization package may be sealed, e.g., by an outer container 60 (e.g., a sealed bag) surrounding the other contents of the catheterization package, such that the contents remain sterile and properly contained. Just inside the sealed bag (or other external container), a paper or cardboard packaging label 62 may be included in the catheterization package. The external container 60 (or sealed bag) may be transparent, or at least partially transparent, such that a clinician may see the label 62 or portions of the label. The label 62 may include sides 64 that are foldable such that they extend down the sides of the catheterization package. The label may include one, two, three, or four sides. For example, FIGS. 11 and 12 each show a label 62 that a large top portion 66, and 3 smaller sides or side portions 64 foldable to a different plane from the plane in which the large top portion 66 resides. Lines on FIG. 12 show where the folds may be made to form the sides or side portions. In one embodiment, the label has four sides or side portions 64 instead of three.

The packaging label 62 may include instructions and or other information thereon. For example, the label 62 may include initial instructions for catheterization. The label 62 may include a logo, trademark, or product name printed or otherwise included thereon, e.g., "SureStep™ Foley Tray System", Lubrisil® I.C. Complete Care®, and/or "BARD." The label 62 may also, or alternatively, include instructions related to the catheterization written thereon. For example, the label may include instruction(s) 40 to verify whether the patient meets the CDC guidelines for indwelling urethral catheter use, as shown in the bottom left quadrant of the top portion 66 of the labels 62 in FIGS. 9-12. The label may include a checklist 41 to verify the different factors that qualify a patient for indwelling urethral catheter use under the CDC guidelines, e.g., as also shown in the bottom left quadrant of the top portion 66 of the labels 62 shown in FIGS. 9-12. The label 62 may also include a list of components 42 of the catheterization package as shown on the right side the top portion 66 of the labels 62 in FIGS. 9-12. The instructions or other information may be in upper case letters, in bold, or otherwise called out for greater visibility to ensure the clinician reads the instructions or other information.

The packaging label 62 may also include key information or variables called out in a simplified and easy-to-read manner. For example, visual identifiers, squares, other shapes, and/or other features may be included that each have an indicator of one key piece of information or variable called out and easy to read. In FIGS. 9-12, the labels 62 are shown as including information squares 44 that each includes an indicator of one key piece of information about the catheterization package. Information squares 44 essentially isolate and feature particular information about the catheterization tray from a range of possibilities or variables. Various features or variables may be called out, including: (1) whether the tray includes a drainage bag or a urine meter, (2) the French size of the catheter, (3) the type of catheter included, (4) the substrate type of materials used in the catheter or other components, e.g., latex or latex-free, (5) special components or features, e.g., inclusion of a Stat-Lock® securement device, inclusion of special infection control coating, or other features. This calling out of particular variables, separated from everything else, allows the health care provider to see what is in the catheterization package or tray at a glance. Accordingly, the health care provider can quickly determine what the key distinguishing elements of the catheterization package or tray are. For example, if the catheterization package shown in FIG. 9 and the catheterization package in FIG. 10 were both stored on the same shelf, a health care provider could quickly tell the major differences between the catheterization packages just by looking at the information squares 44. One can readily tell from the information squares 44 in FIG. 9 that the catheterization package in FIG. 9 includes an 18 French sized catheter, a drainage bag, Bard's StatLock®, and is a non-latex catheter. One can readily tell from the information squares 44 in FIG. 10 that the catheterization package in FIG. 10 includes a 16 French sized catheter, a drainage bag, and Bard's StatLock®.

Further, the packaging label 62 may be designed to be visible in multiple planes. The label may be designed to fold at the edges of the catheterization package such that the label (or a portion of the label) forms sides or side portions that are visible when the catheterization package is viewed from the sides, in addition to being visible from the top. In FIGS. 9-12, the labels 62 are designed such that information squares 44 are visible from the top of the catheterization package, and at least two sides of the tray. Optionally, the label may also be designed such that information squares 44 appear on all the sides of the catheterization package (e.g., on three sides or four sides). Accordingly, anyway you stock the catheterization package, you can see the label. Further, multiple catheterization packages may be stacked on top of each other, but because of the information squares on one or more sides of the catheterization package, a clinician can still quickly tell from the sides of the packages in the stack which catheterization package from the stack is the one desired for a particular patient.

The catheterization package may be selected based on the information squares 44, e.g., after reviewing the information squares 44. After providing/obtaining/selecting the catheterization package, the user may open the container (e.g., the sealed bag) and remove it from around the remainder of the catheterization package. After the container (or sealed bag) has been removed the remainder of the catheterization package looks, for example, as shown in FIG. 11.

The user may then remove the label 62 and set it aside to reveal other components that were underneath the label 62. For example, when the label is removed from the catheterization packages shown in FIGS. 9-11, detailed instructions for catheterization or the directions for use document 68 of the catheterization package or tray may be revealed as shown, for example, in FIG. 13. Detailed instructions and/or information on safety considerations are thereby one of the first items accessed in the catheterization package. Providing detailed instructions up front allows the user/clinician/health care provider to review the entire procedure in advance of any other steps and before breaking the sterile field formed by the CSR wrap around the catheterization tray. This helps the procedure to run more efficiently and safely. Pages of detailed instructions may be seen on various pages of document 68 in FIGS. 14A-14D. Any one or more of the steps contained in FIGS. 14A-14D may be performed as a catheterization method or procedure.

Additionally, there may also be associated patient education information whether attached to the detailed instructions or separately placed in the catheterization package. The patient education information may be used by a health care provider to instruct the patient on care of the indwelling catheter and may, ultimately, be given to the patient for reference. FIGS. 15A and 15B show an example of patient education information that may be included on a patient sheet/pamphlet 70 in the catheterization tray. FIG. 15A shows a first side of the patient education information sheet 70 in English, whereas FIG. 15B shows a second side of the patient education information sheet 70 in Spanish.

Figure 16:
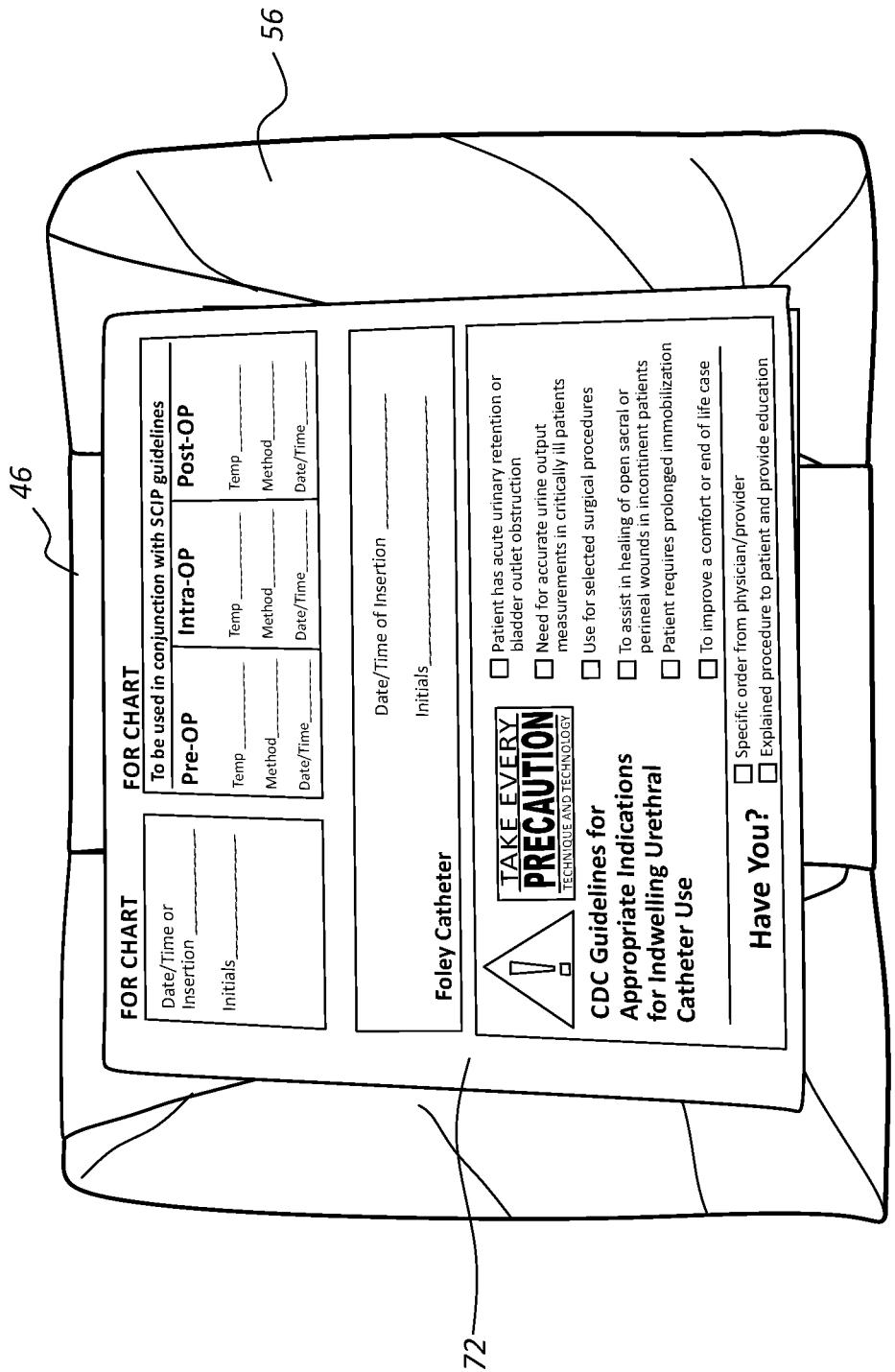
FIG. 16 shows a top view of the catheterization package of FIG. 13 without the detailed instructions/procedural indicators document or directions for use (DFU) document, and showing a label or insert sheet thereon.

Underneath the detailed instructions or directions for use document, the catheterization package may include a checklist of safety considerations/steps, a patient information chart, or an insert sheet including safety consideration/steps and a patient information chart combined on the same insert sheet. FIG. 16 shows an insert sheet 72 on which patient information can be recorded or charted and including safety information. This insert sheet 72 may be accessed after the detailed instructions are removed from the package. It may be beneficial to have an insert sheet 72 in this location to do one last safety check prior to treating the patient and to have important patient information at hand. The insert sheet 72 may be configured as a sticker label, e.g., the insert sheet 72 may include a backing that protects a sticker adhesive, and when the backing is removed, the insert sheet 72 may be stuck to a file or chart associated with the patient.

Figure 17:
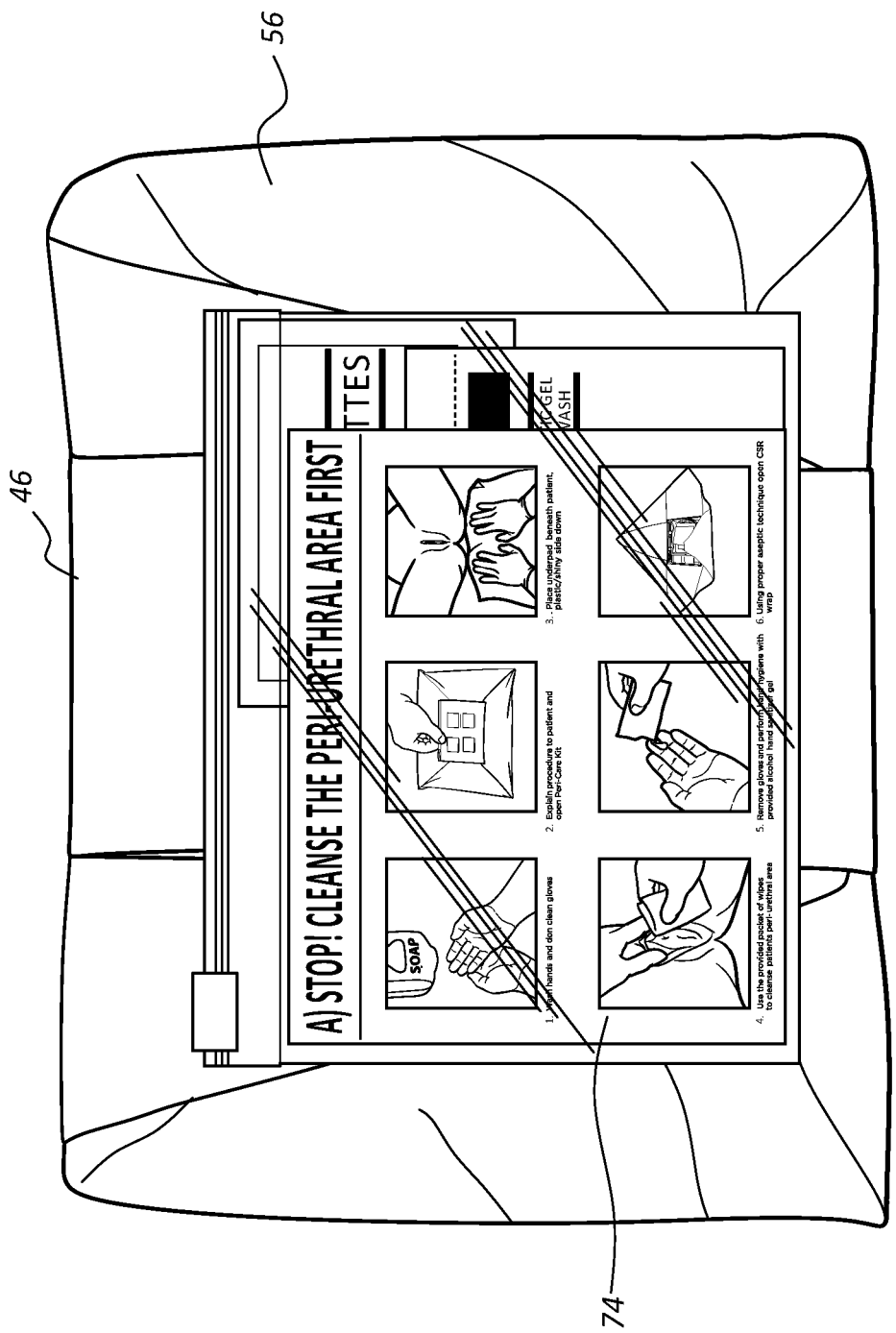
FIG. 17 shows a top view of a catheterization package (e.g., similar to the catheterization package of FIG. 16) without the label or insert sheet, and showing a perineal care or peri-care kit/packet thereon.
Figure 18:
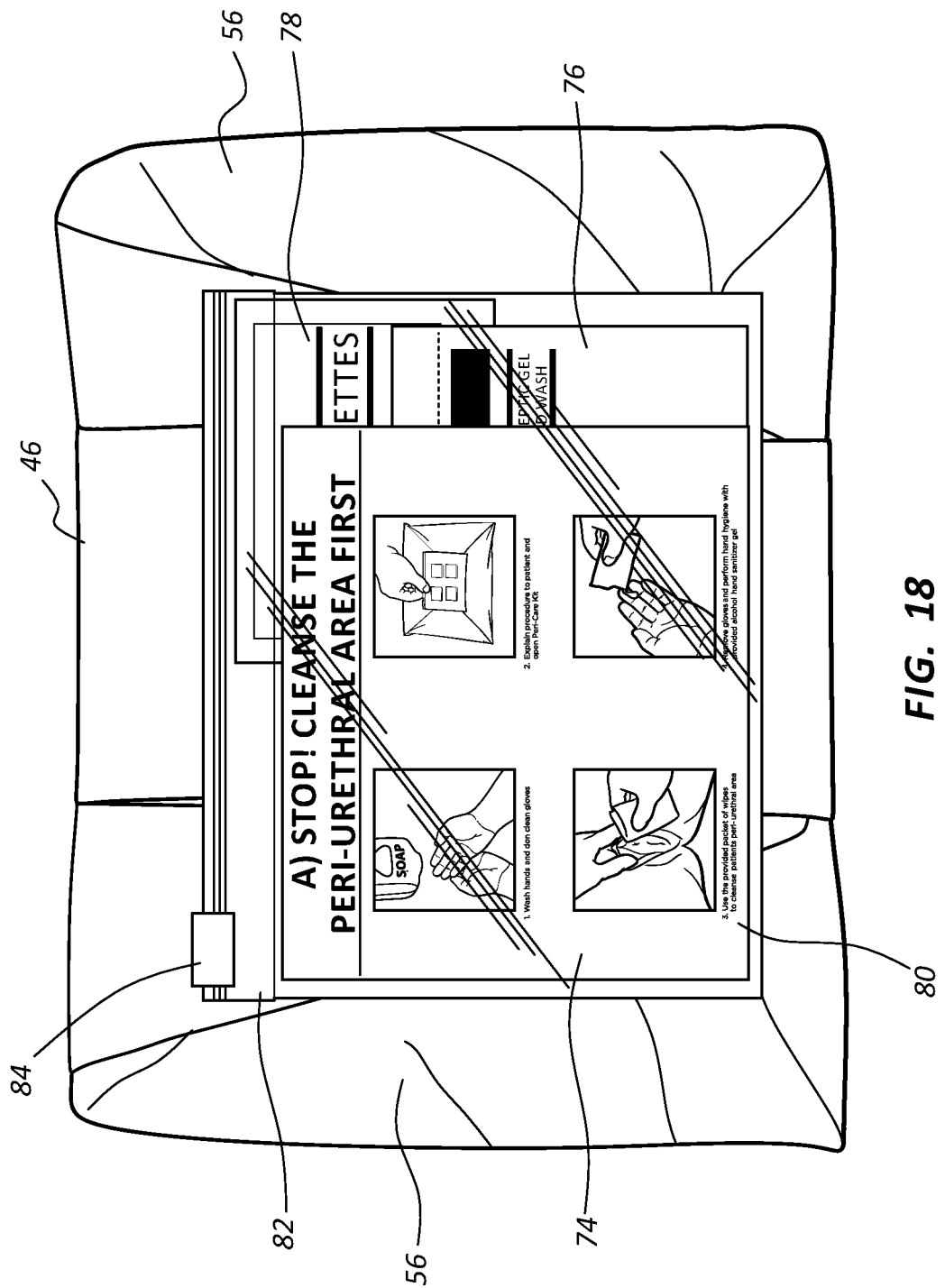
FIG. 18 shows a top view of a catheterization package (e.g., similar to the catheterization package of FIG. 16) without the label or insert sheet, and showing another, different perineal care or peri-care kit/packet thereon.
Figure 19:
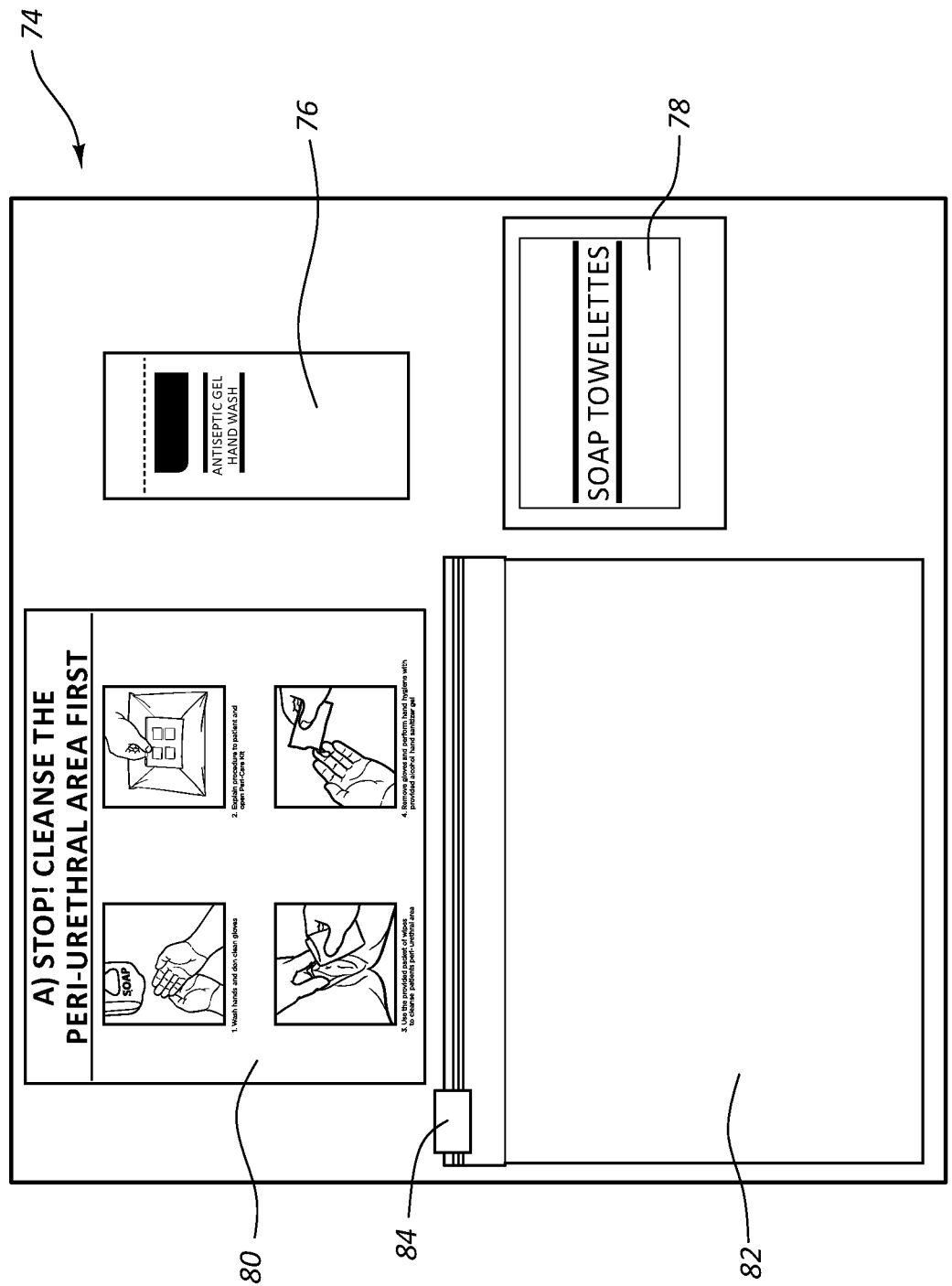
FIG. 19 shows a separated view of the components of the perineal care (or peri-care) kit or packet of FIG. 18.

After removing the detailed instructions 68 and the insert sheet 72 from the catheterization package, a perineal care (or peri-care) packet or kit 74 is revealed, as shown in FIGS. 17 and 18, and may be accessed. A peri-care kit is helpful to provide an initial cleaning of the area where the catheterization takes place prior to using an iodine solution to further cleanse and sanitize the area. This is especially true for patients who are very dirty and must have an initial cleaning before the iodine solution will be most effective. The peri-care kit may include any items helpful for an initial cleaning of the patient's perineum or for perineum care in general. For example, as shown in FIGS. 18 and 19, the peri-care kit may include hand sanitizer 76 (e.g., antiseptic gel hand rinse) for the health care provider to sanitize his/her hands, moist towelettes 78 (e.g., a package of castile soap towelettes), instructions/procedural indicators 80 (e.g., instructions/procedural indicators for health care provider and/or instructions for patient). The hand sanitizer may be designed to have improved efficacy and/or to enable single-handed usage.

As shown in FIGS. 17-19, the items of the peri-care kit may be included in a bag 82 (e.g., a zip lock baggy) or other package to keep the items/components together. In one embodiment, the bag type used is a baggy including a zipper 84. It has been found such a bag type is easier to open with gloves on rather than, for example, a bag without a zipper or a bag that must be opened by tearing. However, a bag with perforations on the bag instead of a zipper or zip-lock feature is also contemplated, as such may be cheaper to manufacture.

Peri-care instructions/procedural indicators 80 are shown in FIGS. 17-19. The instructions 80 may inform a health care provider to: "1. Wash hands and don gloves," "2. Explain procedure to patient and open Peri-Care kit," "3. Use the provided packet of towelettes to cleanse the patient's peri-urethral area," and "Remove gloves and perform hand hygiene with provided alcohol hand sanitizer gel." Other instructions/procedural indicators are also possible. The method may include performing some or all of the four steps recited above as steps on the instructions.

The method may proceed in three main stages, i.e., (A) the initial peri-care stage, (B) the catheterization stage, and (C) the catheter care and maintenance stage. Each of these stages is denoted on the instructions/procedural indicators and/or other materials with a large "A" "B" or "C" to signify the different main stages. As can be seen on the peri-care instructions 80, there is a large "A" at the top of the instructions/procedural indicators to indicate the first stage. As discussed elsewhere herein, the belly band 46 includes a large "B" to indicate the second stage, and the main compartment 1 of the catheterization tray includes a large "C" to indicate the third stage.

Figure 20:
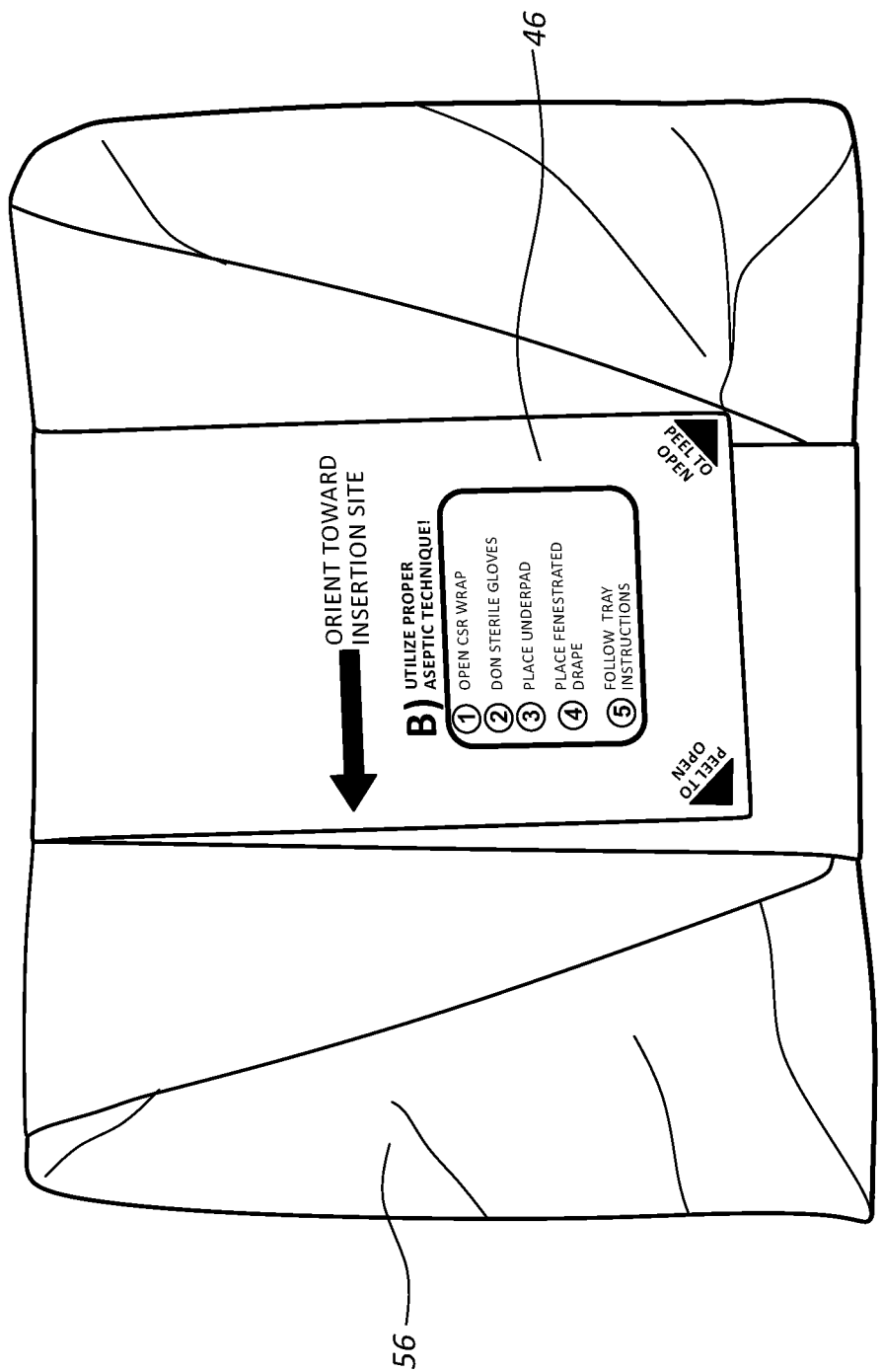
FIG. 20 shows a top view of a catheterization package (e.g., similar to the catheterization package of FIG. 17 or FIG. 18) without the perineal care (or peri-care) kit or packet, and showing a belly band including instructions/procedural indicators thereon.
Figure 30A:
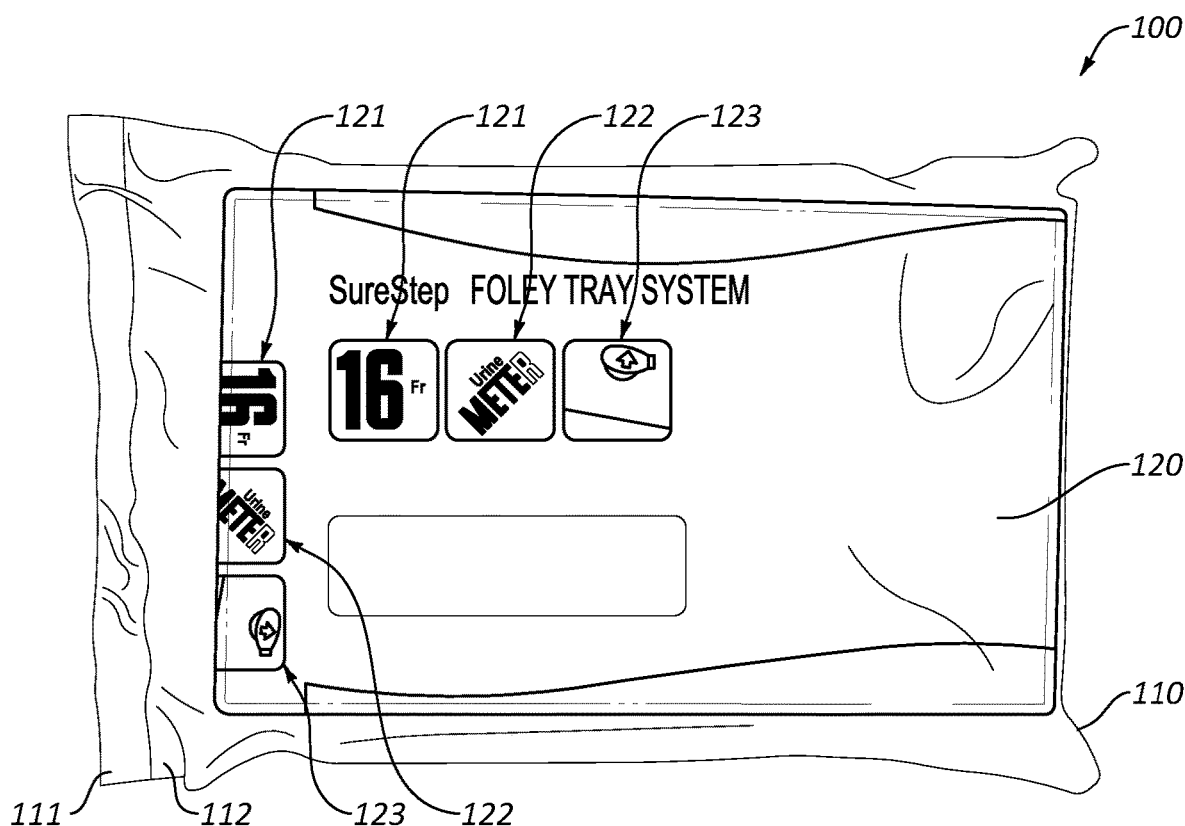
FIG. 30A is a top view of a catheterization system.
Figure 30B:
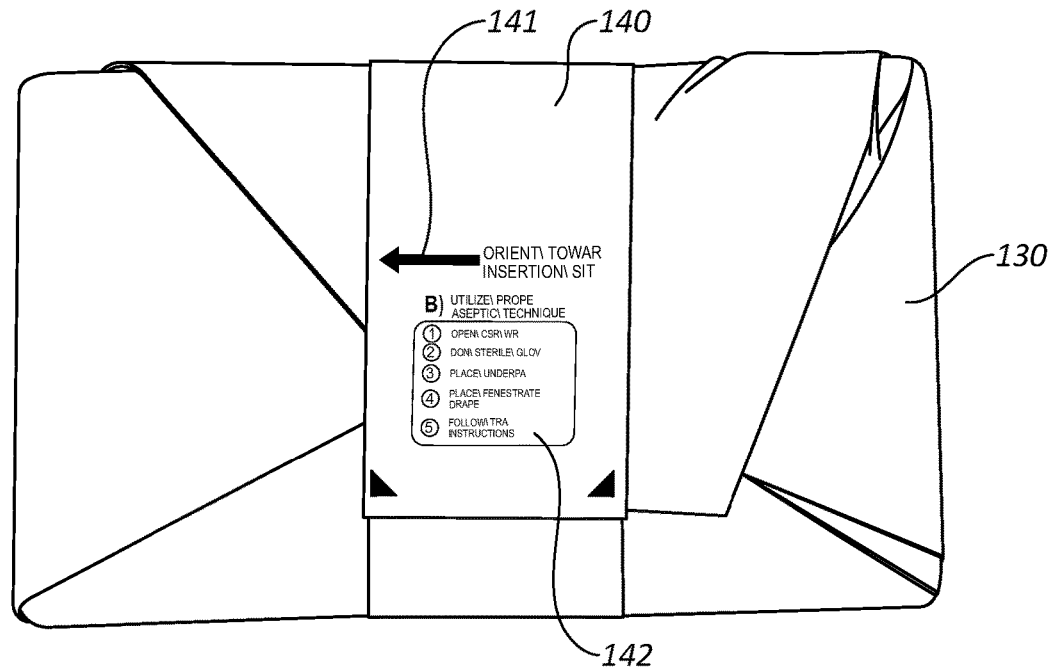
FIG. 30B is a top view of a catheterization tray of the catheterization system of FIG. 30A, which is wrapped in a wrap.

After removing and using the peri-care kit, a belly band/indicator wrapper 46 may be revealed as shown in FIG. 20 (see also indicator wrapper 140 in FIG. 30B). The belly band 46 may circumvent the tray in at least one direction. The belly band 46 may help to keep the CSR wrap intact and maintain the sterile barrier. The belly band 46 may also help to keep all the contents inside the tray, so the items do not move around.

The belly band/indicator wrapper 46 may include instructions/procedural indicators and/or other information thereon. For example, as shown in FIG. 20 (see also FIG. 30B), the belly band may include an instruction/procedural indicator telling the health care provider how to orient the tray relative to the patient. For example, the belly band may say, "orient toward insertion site" and have an arrow pointing to the end of the catheterization tray that should be positioned closest to the patient's perineum and urinary tract. This ensures that the tray is properly positioned for most logical and intuitive use when the CSR wrap is opened.

Further, as shown in FIG. 20 (see also indicator wrapper 140 in FIG. 30B), the belly band 46 may include instructions/procedural indicators to "utilize proper aseptic technique," "(1) Open CSR Wrap," "(2) Don Sterile Gloves," "(3) Place Underpad," "(4) Place Fenestrated Drape," and (5) "Follow Tray Instructions. These instructions/procedural indicators include a large "B" at the top to signify that these instructions/procedural indicators are part of the second stage or catheterization stage. The instructions/procedural indicators inform the health care provider to open the CSR wrap and perform other steps once the CSR wrap is opened. Providing this information before breaking the sterile barrier gives the health care provider a preview of the procedure, and ensures he/she is prepared when the sterile barrier is broken by opening the CSR wrap. Optionally, a label or sticker may be used instead of a belly-band, which may provide the same information as the belly band described herein.

Figure 21:
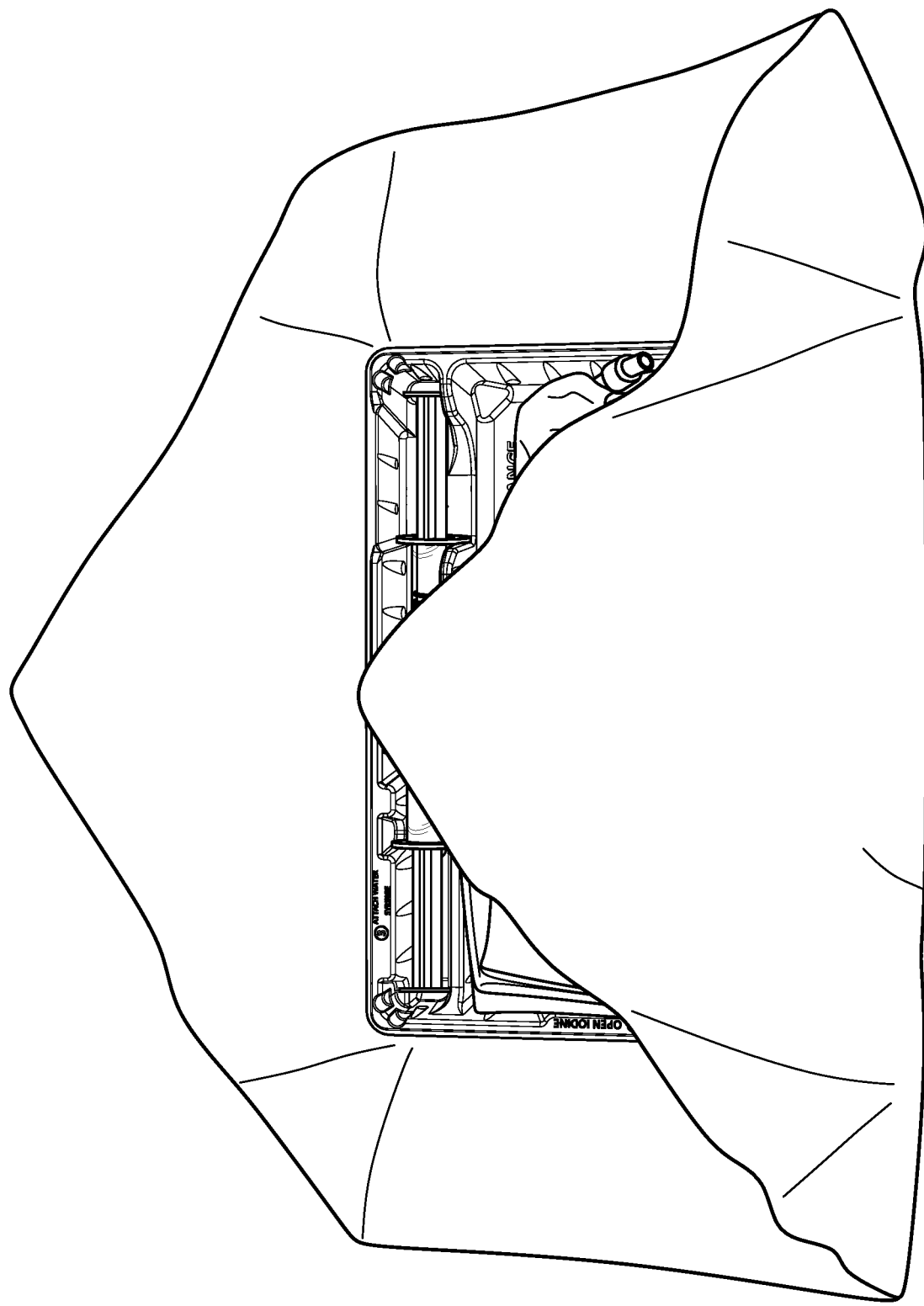
FIG. 21 shows a top view of a catheterization package (e.g., similar to the catheterization package of FIG. 20 or FIG. 21) without the belly band, and showing the sterile wrap only partially folded/wrapped around a catheterization tray.

Once the tray is oriented and the health care provider has read the belly band instructions/procedural indicators, the next step is to open and/or remove the belly band. After removing the belly band, the sterile wrap 56 (e.g., CSR wrap) may be opened. FIG. 21 shows the catheterization tray with three corners of the sterile wrap 56 unfolded to represent unfolding the sterile wrap 56. Note that until the belly band and sterile wrap are opened, the sterile barrier of the catheterization tray and its components is not broken. This maintains the sterile barrier while the initial peri-care stage is completed and while the tray is properly positioned and oriented for catheterization. By leaving the sterile barrier intact during the initial steps of the method, there are fewer opportunities for contamination and the resulting patient infection.

Figure 22:
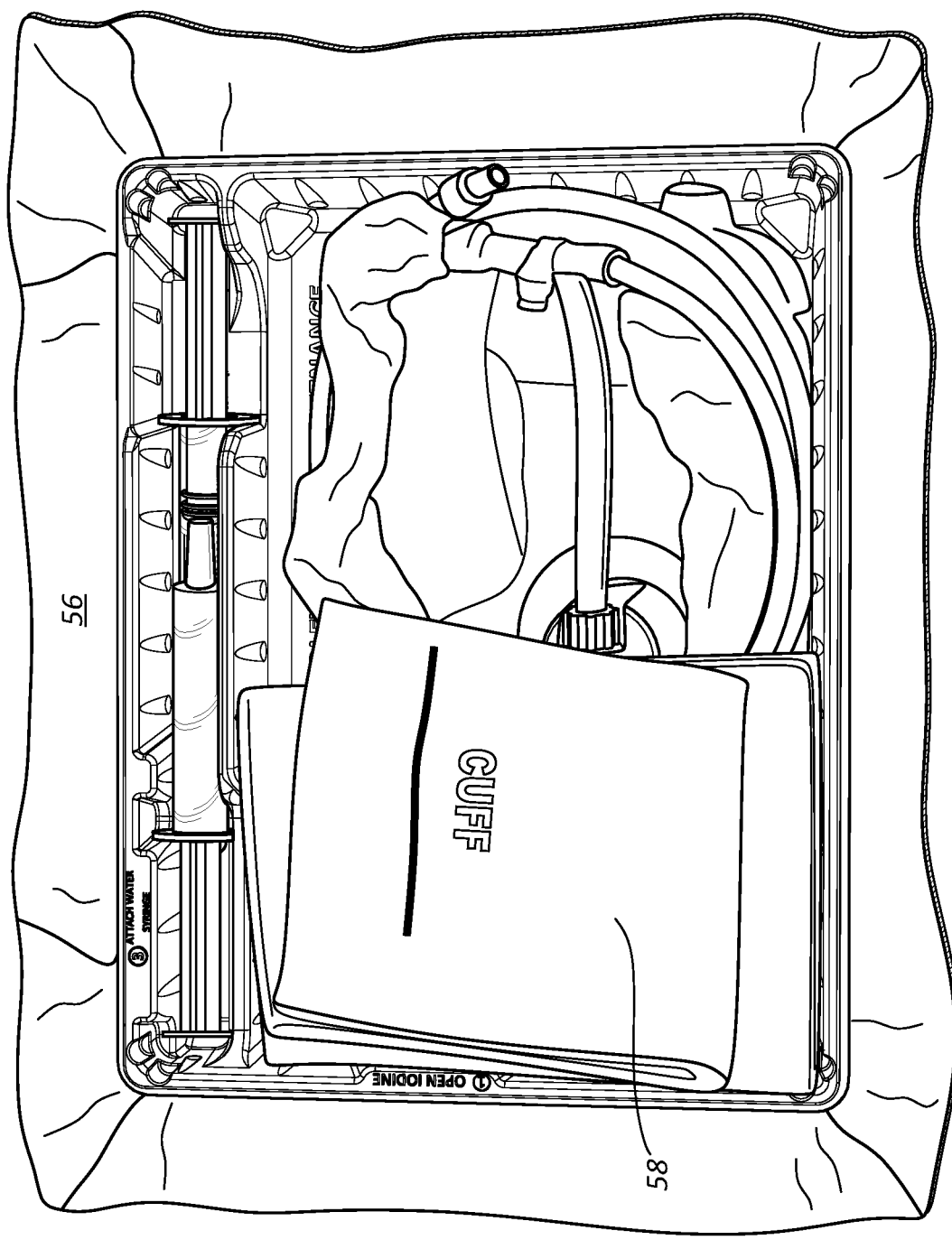
FIG. 22 shows a top view of the catheterization package of FIG. 22 with the sterile wrap completely unfolded but remaining underneath the catheterization tray, and showing the contents of the catheterization tray before any components have been removed or, during manufacture/packaging, after all the components to be within the sterile wrap have been placed therein.

If the catheterization tray is oriented as directed by the belly band 46, when the sterile wrap 56 (e.g., CSR wrap) is opened, the tray is properly oriented for logical and convenient use of the catheterization tray and its components. The tray is arranged and ordered for logical step-by-step use as described herein. The initial view of the tray after opening the sterile wrap 56 entirely is shown in FIG. 22. (A breakaway line is used to indicate that the actual edges of the sterile wrap 56 extend beyond the breakaway edges shown in FIGS. 22-29.) Note that the sterile wrap 56 may remain underneath the catheterization tray to form a sterile field for catheterization. The tray shown in FIG. 22 and the other figures are right-hand biased to make use easier for a right-handed health care provider when standing near the lower edge of the catheterization tray with the syringe or catheter compartment positioned furthest from the health care provider (i.e., if the band points toward the genitalia between the legs, the right-handed user stands on the side closest to the patient's right leg). Alternatively, a catheterization tray may be left-hand biased (e.g., essentially a mirror image of the tray shown in FIGS. 22-29 with the mirror placed along the tray's side 7 or along the syringe or catheter compartment).

Figure 23:
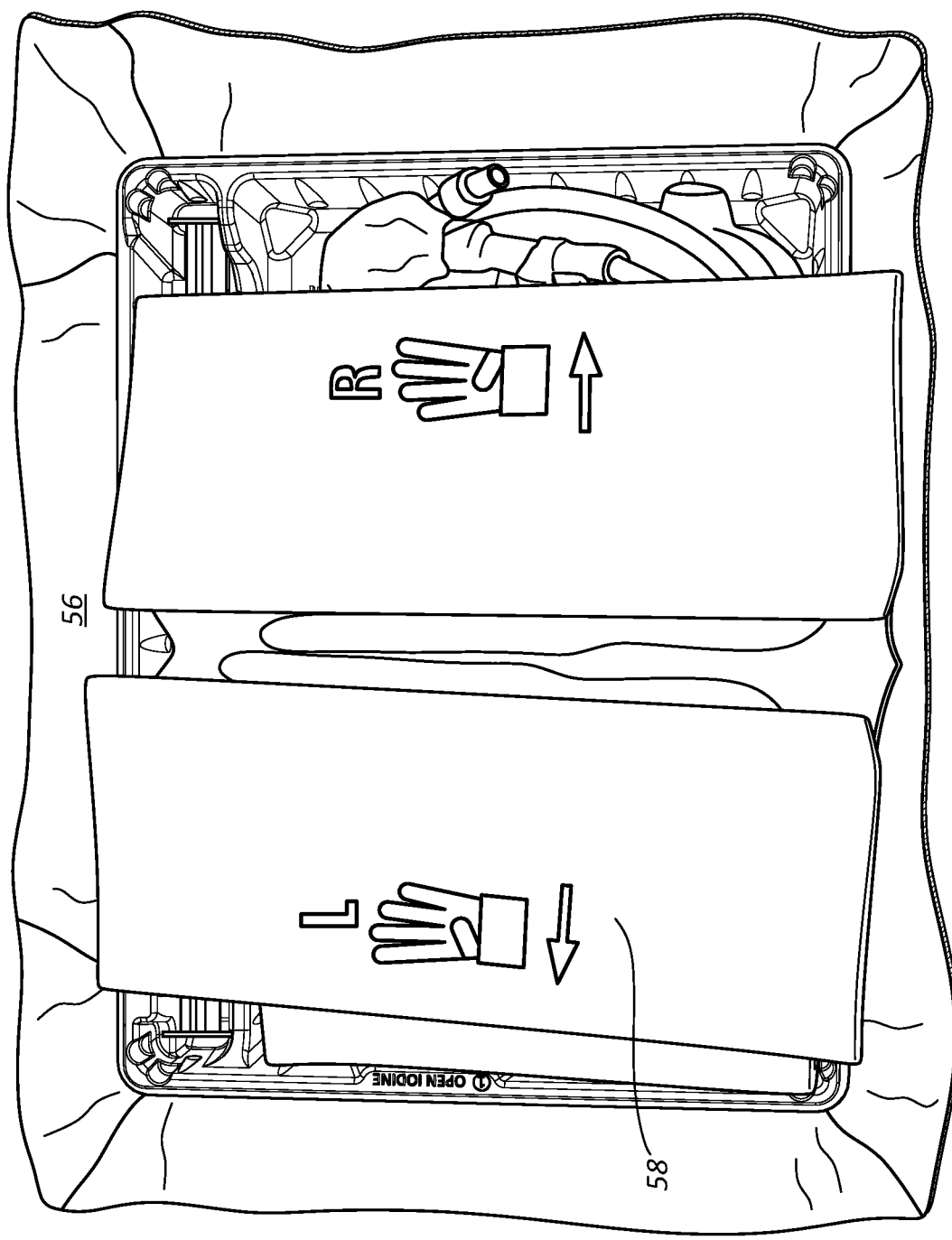
FIG. 23 shows a top view of the catheterization package of FIG. 23 with a package of sterile gloves partially unfolded and sitting on top of the catheterization tray.

As instructed on the belly band 46, after first opening the CSR wrap, the health care provider next dons the sterile gloves provided in the tray. As shown in FIG. 22, the top item in the tray after the CSR wrap is opened is a package 58 of sterile gloves (note that the cuff end of the gloves may be indicated on the package 58). The sterile gloves may be made of any material known to be suitable, e.g., latex, rubber, or latex-free materials). This placement of the gloves on top of the tray under the sterile wrap helps the health care provider to intuitively know he/she should don the gloves before proceeding further (because it is intuitive, it may be unnecessary to refer back to the instructions/procedural indicators on the belly band 46). The package of gloves 58 may be opened by folding the cuff down to be closest to the health care provider and then opening the package like a book, as shown in FIG. 23. If opened in this intuitive, logical way, the left hand glove is positioned on the health care provider's left side and the right hand glove is positioned on the health care provider's right side for easy donning of the gloves. A symbol or other indicator may be included on the package 58 to identify the left and right hand gloves as shown, for example, in FIG. 23.

Figure 24:
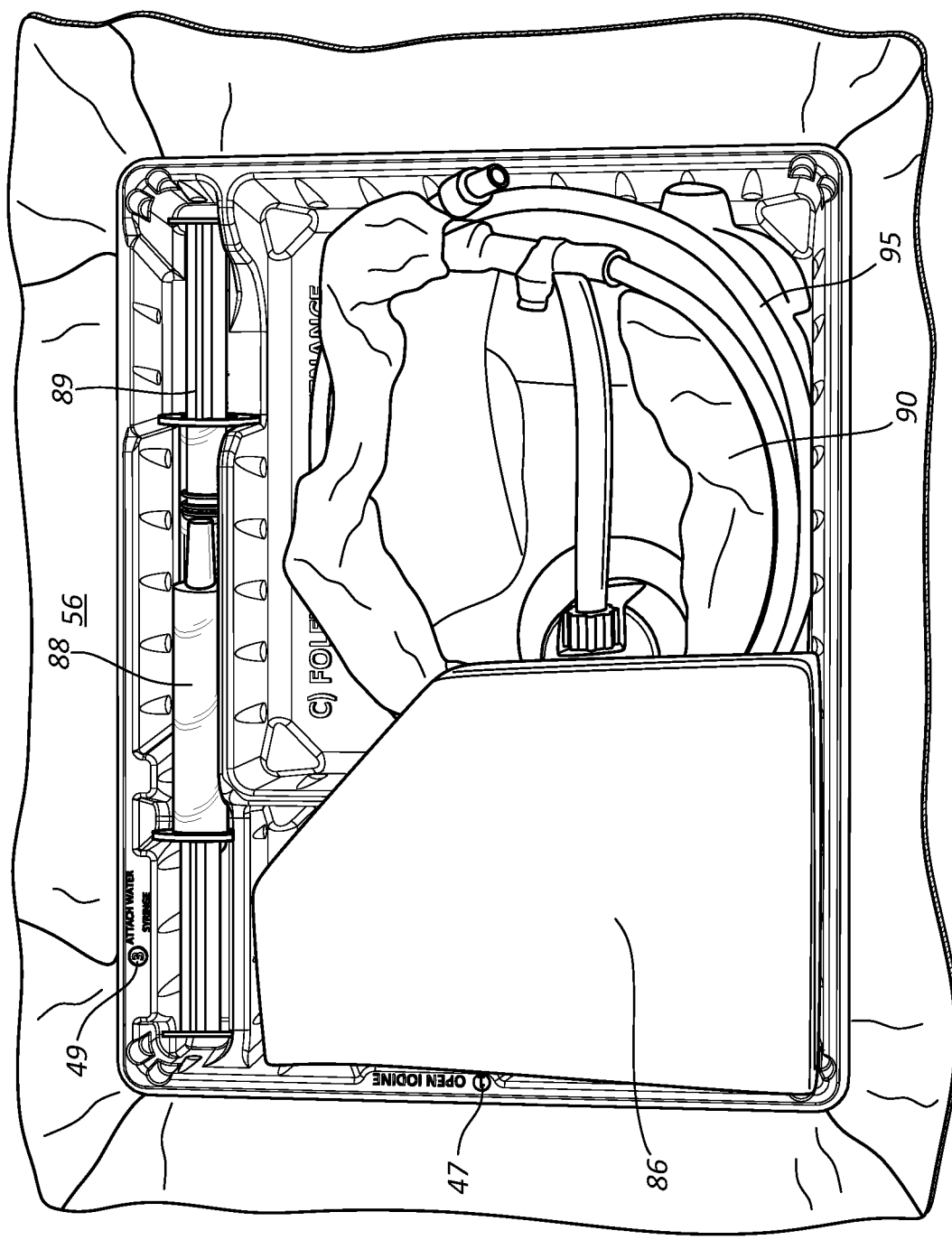
FIG. 24 shows a top view of the catheterization package of FIG. 24 without the package of sterile gloves, and revealing a pad/drape (representative of a waterproof underpad and/or a fenestrated drape) sitting on top of the catheterization tray.

As instructed on the belly band 46, after donning the gloves, the health care provider places an underpad under the patient's buttocks. As shown in FIG. 24, once the package of gloves is removed from the tray, the underpad and fenestrated drape are revealed. The folded pad/drape 86 shown in FIG. 24 is representative of: (1) a waterproof underpad, and (2) a separate fenestrated drape. The underpad may have a waterproof side and a liquid absorbent side. If so, the absorbent side is placed up under the patient, and the waterproof side (or plastic side) is placed down. As instructed on the belly band 46, after placing the underpad, the health care provider places the fenestrated drape on the patient such that the genitalia are visible through the central opening in the fenestrated drape. Although the underpad and fenestrated drape are not shown in FIG. 24 as distinct pieces, they are both included in the area of the pad/drape 86, and are arranged such that the underpad is on top of the fenestrated drape (i.e., because the underpad is placed first, which reveals the fenestrated drape for placement thereafter). The fenestrated drape is logically located and folded such that it is intuitive to open the drape away from clinician, which is preferable for how the drape is best used.

Figure 25:
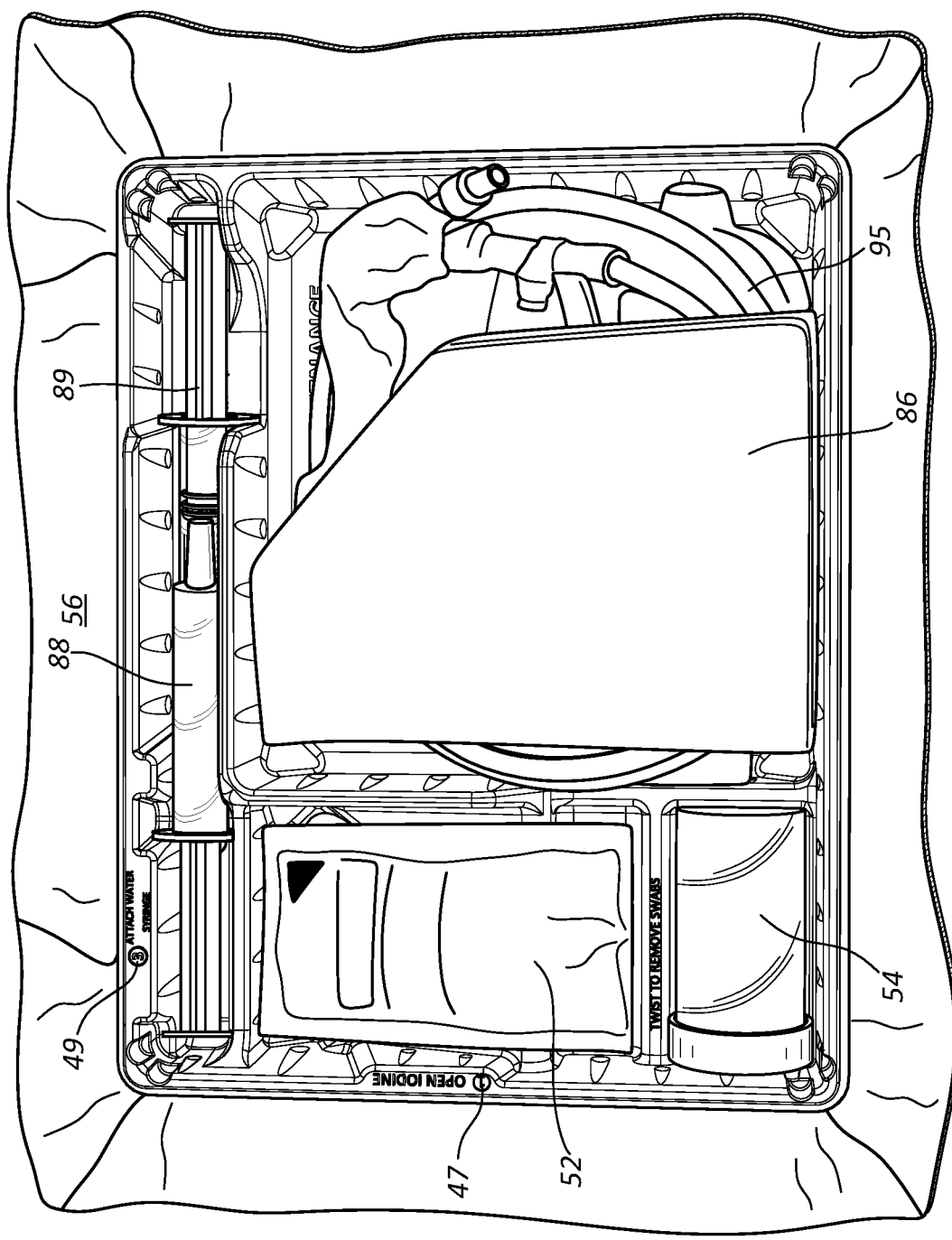
FIG. 25 shows a top view of the catheterization package of FIG. 25 with the pad/drape moved off the swab compartment, and revealing a packet of povidone-iodine solution sitting in the swab compartment and extending over the small storage or overflow compartment of the catheterization tray.

As instructed on the belly band 46, after placing the fenestrated drape, the health care provider follows the instructions/procedural indicators and/or takes the steps written on the catheterization tray itself. As shown in FIG. 25, removal of the underpad and fenestrated drape reveals a package of antiseptic solution 52 (e.g., povidone-iodine solution). (Note that FIG. 25 shows the fenestrated drape moved from over the swab compartment 3 into the main compartment 1. Moving the drape in this way or placing the fenestrated drape on the patient will reveal the antiseptic solution in the swab compartment.) Further, the first instruction/procedural indicator 47 on the tray (i.e., "(1) Open Iodine"; although, variations on this instruction or other instructions are possible) is visible on the left side of the tray (which is also the side closest to the patient and the region to be catheterized, if oriented as instructed by the belly band 46). Placement of the first instruction 47 on the left is logical because people read English from left to right, and beginning instructions on the left is intuitive (although in countries that do not read left to right, this might be adjusted). Also the instruction/procedural indicator is located close to the antiseptic or iodine solution 52 in the tray, which makes following the instruction/procedural indicator easier and more intuitive.

Assuming the clinician is right-handed, and has oriented the tray as instructed by the belly band 46, the antiseptic or iodine solution 52 is automatically positioned closest to patient. (However, as discussed above, another arrangement is possible where the tray is left-handed biased (e.g., essentially a mirror image of the tray in the figures) such that a left-handed user positioning the tray as instructed by the belly band would also automatically position the antiseptic or iodine solution closest to the patient (e.g., with the left-handed clinician standing on an opposite side of the tray from where a right-handed clinician would stand or on the side closest to the patient's left leg).) Positioning the antiseptic or iodine solution (and the swab compartment) closest to the patient is preferable for the use of the tray. Having the swab compartment 3 and well of iodine solution closest to the patient is beneficial, because it prevents dragging or moving swabs saturated with the antiseptic or iodine solution across the tray (which might drip on other components of the tray, if moved over them).

Figure 26:
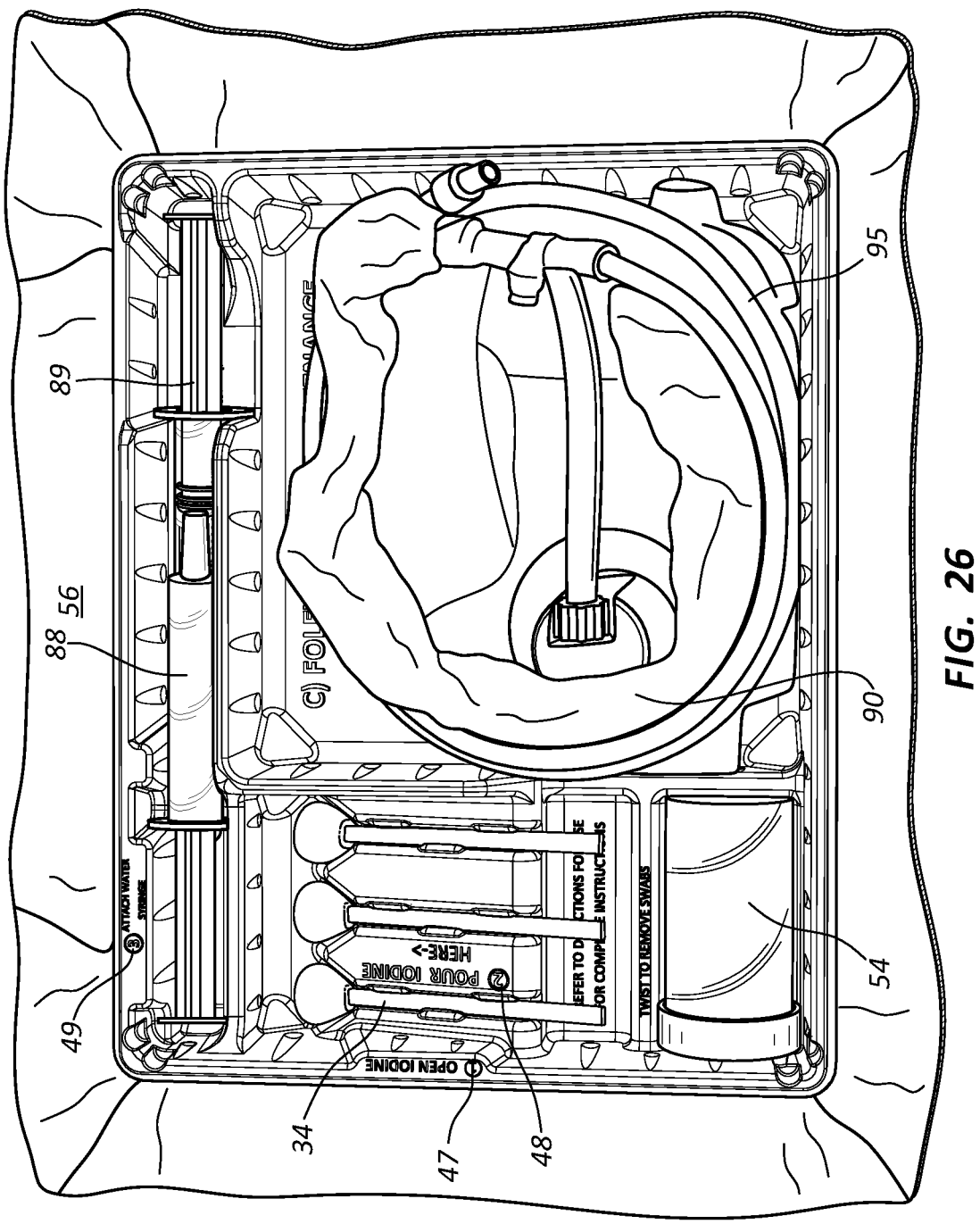
FIG. 26 shows a top view of the catheterization package of FIG. 26 without the povidone-iodine solution, and revealing the swabs or swabsticks in the swab compartment with the proximal ends of the sticks extending over the small storage or overflow compartment of the catheterization tray.

FIG. 26 shows the catheterization tray after removal of the povidone-iodine solution. Note that removal of the packet of antiseptic or iodine solution 52 reveals the swabs or swabsticks 34 and the second instruction/procedural indicator 48 on the tray. This intuitively leads the health care provider to logically follow the second instruction 48 after picking up the packet of antiseptic or iodine solution. The second instruction 48 on the tray is in the swab compartment 3 and says "(2) Pour Iodine Here→" and points to the lowest/deepest point or well of the swab compartment 3 (although, variations of this instruction or other instructions are possible). If antiseptic or iodine solution is poured on the barriers or channels of the swab compartment 3, the incline ensures the solution will flow to the lowest/deepest point or well.

Figure 27:
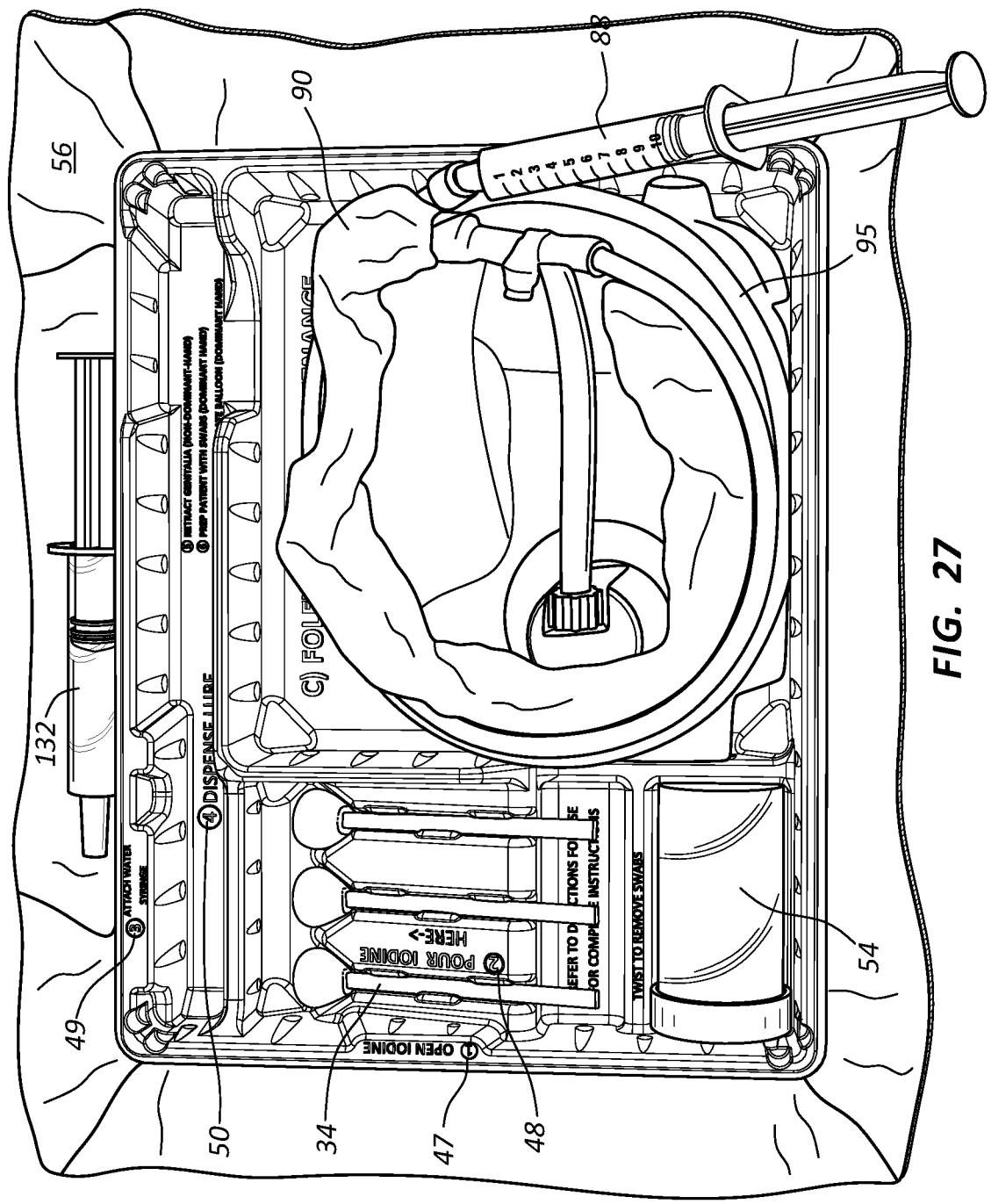
FIG. 27 shows a top view of the catheterization package of FIG. 27 with the syringe of sterile liquid attached to the inflation port of the catheter.

Once the health care provider has poured the antiseptic or iodine solution into the well of the swab compartment 3 such that the absorbent heads of the swabs begin absorbing the antiseptic or iodine solution, the health care provider may then attach the syringe of sterile liquid 88 to the inflation port of the catheter 92 (e.g., a Foley catheter) as is instructed by the third instruction/procedural indicator 49. The third instruction 49 is logically located on side 7 of the tray not far from the well of the swab compartment where the health care provider has just poured the antiseptic or iodine solution, and near the syringe of sterile liquid to be used in the third instruction. The third instruction 49 states "(3) Attach Water Syringe" (although, variations on this instruction or other instructions/procedural indicators are possible). FIG. 27 shows the syringe of sterile liquid or water 88 after it has been attached to the inflation port of the catheter 92.

Figure 28:
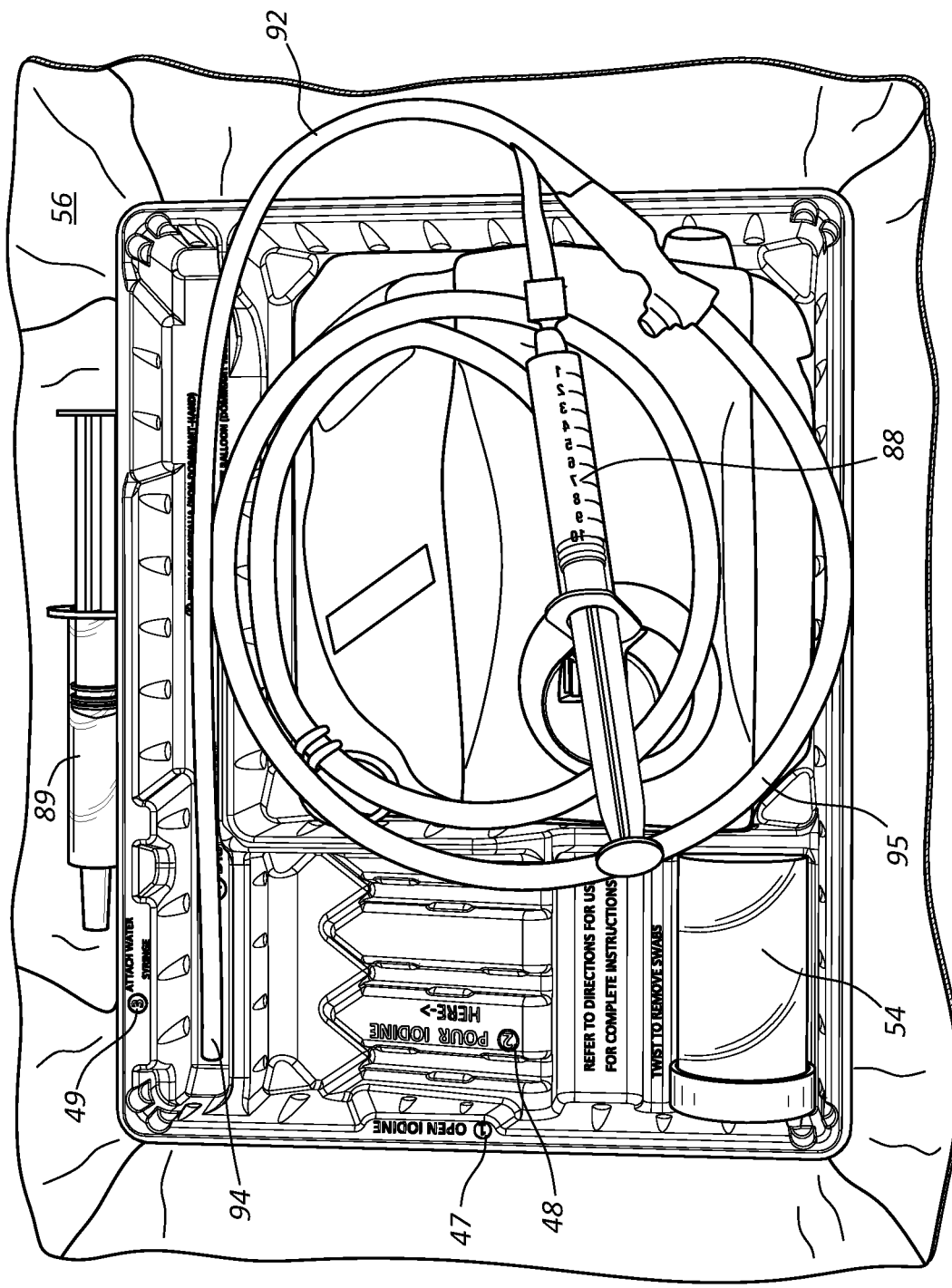
FIG. 28 shows a top view of the catheterization package of FIG. 28 with a distal portion of the catheter positioned in the syringe or catheter compartment and the syringe of lubricating jelly adjacent to syringe or catheter compartment ready to dispense the lubricating jelly on top of the distal region or distal end of the catheter.

Once the syringe of sterile liquid 88 is removed from the syringe or catheter compartment, the fourth instruction/procedural indicator 50 is revealed (which was previously obscured by the syringe of sterile liquid). The fourth instruction 50 may inform the health care provider to "(4) Lube Catheter" or "(4) Dispense & Lube Foley Here" or something similar (again, variations on this instruction or other instructions/procedural indicators are possible). Indeed, lubricating the catheter is the next step taken by the health care provider. To do so, the health care provider removes the syringe of lubricating jelly 89, which removal reveals the fifth, sixth, and seventh instructions/procedural indicators that were previously obscured by the syringe of lubricating jelly 89. In accordance with the present disclosure, the lubricating jelly can be provided in other suitable containers well-known to those of ordinary skill in the art, with non-limiting examples including a bellows, an ampoule, or the like. The health care provider can then lubricate the catheter in any way desired. In one embodiment, the health care provider can remove the plastic wrap 90 (shown in FIGS. 27 and 28) from over the catheter 92 (which can be a Foley catheter) and move a portion of the catheter 92 into the syringe or catheter compartment 2, e.g., as shown in FIG. 28. Placing the distal end 94 of the Foley catheter 92 in the syringe or catheter compartment 2 helps to line the catheter 92 up for lubrication and catheterization. For example, as shown in FIG. 28, with the distal end 94 of the catheter 92 positioned near the left-most side of the syringe or catheter compartment 2, the distal end 94 of the catheter 92 is positioned very near the patient and the region to be catheterized (assuming the tray has been oriented as directed by the belly band 46). Further, the distal tip of the catheter 92 is positioned such that it essentially points at the region to be catheterized such that the health care provider may simply lift the catheter 92 and move it a short distance in the direction it is pointing to begin insertion of the catheter 92 into the patient. Once the catheter 92 is positioned in the syringe or catheter compartment 2, the user may dispense the lubricating jelly from the syringe 89 into the syringe or catheter compartment 2 onto a distal portion of the catheter 92 (e.g., the syringe may be dispensed on the left side of the syringe or catheter compartment near the patient and the region to be catheterized), and twist the catheter 92 in the lubricating jelly to ensure it is properly lubricated.

While the above lubrication method is beneficial for the reasons discussed above, other methods of lubricating the catheter 92 are also possible. In one embodiment, the health care provider may dispense the lubricating jelly onto a portion of the sterile/CSR wrap around the tray and put the end of the catheter in the lubricating jelly to lubricate. In one embodiment, the user may dispense the lubricating jelly directly into the syringe or catheter compartment 2 before moving the catheter 92 from main compartment 1, and then move the distal portion of the catheter 92 into the lubricating jelly.

After lubricating the catheter 92, the health care provider may leave the catheter 92 temporarily in the syringe and catheter compartment 2 while he/she uses his/her non-dominant hand to retract the genitalia, and uses his/her dominant hand to prepare and sanitize the patient with the swabs or swabsticks saturated with antiseptic or iodine solution. The swabs or swabsticks (e.g., swabs or swabsticks 34 with absorbent head 36 and stick 38 discussed above) may be twisted either clockwise or counterclockwise to easily release them from the channels of the swab compartment as discussed above. Preferably each swab or swabstick will be used for one swipe on the patient only. For female patients, one may cleanse the patient by: (1) using a downward stroke with one swab or swabstick to cleanse the right labia minora and discard the swab or swabstick, (2) using a downward stroke with another swab or swabstick to cleanse the left labia minora and discard the swab or swabstick, and (3) using a third swab or swabstick to cleanse the middle area between the labia minora. For male patients, one may cleanse the patient with a swab or swabstick using a circular motion starting at the urethral meatus and working outward. After prepping and sanitizing the patient in this way, the health care provider uses his/her dominant hand to insert the catheter into the patient's bladder (urine becomes visible in the tubing when the catheter enters the bladder, but two additional inches beyond this point should be inserted to allow the retention balloon to enter the bladder), and inflate the retention balloon in the bladder by injecting the sterile liquid from the syringe of sterile liquid 88 into the catheter 92 through the inflation port. Indeed, these are the steps instructed on the tray in the fifth step, sixth step, and seventh step, which state, respectively, "(5) Retract Genitalia (Non-Dominant Hand)", "(6) Prep Patient with Swabs (Dominant Hand)", and "(7) Insert Catheter & Inflate Balloon (Dominant Hand)." Variations on these instructions/procedural indicators or other instructions/procedural indicators are possible. Once inflated, the health care provider may gently pull the catheter until the inflated balloon is snug against the bladder neck. These steps complete the catheterization stage or stage "B" of the procedure.

Figure 29:
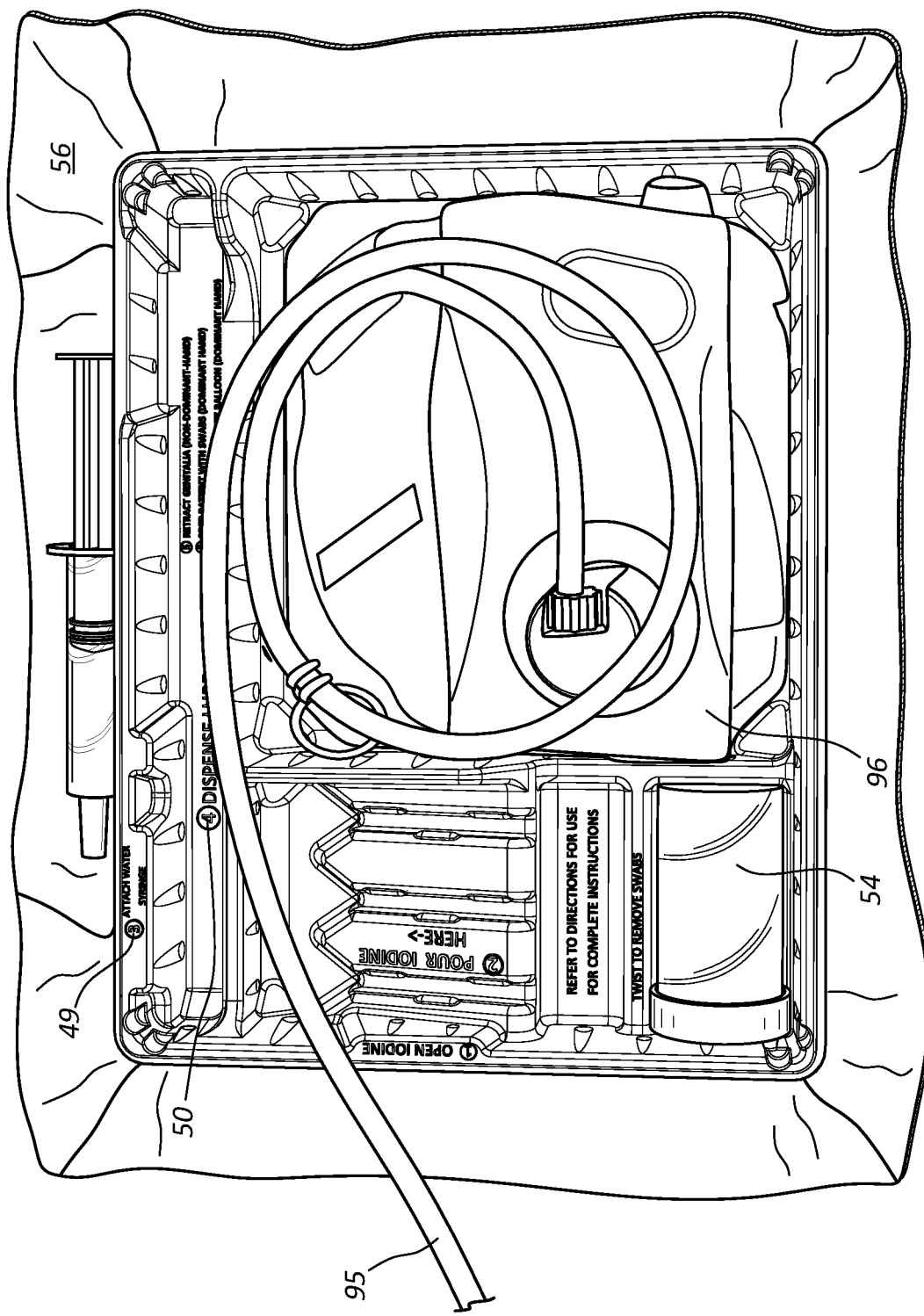
FIG. 29 shows a top view of the catheterization package of FIG. 29 after the catheter has been removed from the tray and inserted in a patient, with the drainage tubing extending in the direction of the patient.

FIG. 29 shows how the tray may look immediately after the catheter has been properly placed in the patient. Note that the drainage tubing 95 easily follows the catheter 92 toward the patient and out of the tray. A folded urine collection bag 96 is positioned in the main compartment 1 in FIG. 29 and may be packaged pre-connected to the tubing 95, catheter 92, and/or other components of the catheter assembly. Urine collection bag 96 may be unfolded and hung below the patient to collect urine as it drains from the patient.

After catheterization of the patient (i.e., after the catheter has been inserted and the retention balloon inflated in the patient's bladder), additional steps may be taken. For example, in stage "C" or the Care and Maintenance stage, the health care provider may: (1) secure the Foley catheter to the patient (e.g., using a StatLock® device), (2) position the urine bag and/or urine meter below the patient's bladder (e.g., hang the bag on a hanger on the bed rail at the foot of the bed) and secure the tubing to the bed sheets (e.g., with a clip) in such a way that the tubing is not kinked, (3) document the insertion date by indicating time and date of catheter insertion on a label and/or chart (e.g., the label/sheet 72 shown in FIG. 16) and document the procedure according to hospital protocol, (4) maintain the catheter (e.g., if it has a sterile red seal, then maintain the red seal), (5) re-assess the need for the indwelling catheter routinely evaluate whether the catheter becomes unnecessary, (6) and/or other care or maintenance steps.

Stage "C" and associated instructions/procedural indicators are identified in the main compartment of the catheterization tray as shown in FIGS. 1, 2, and 5. For example, the stage "C" instructions/procedural indicators may include: "(1) Secure Foley with StatLock®", "(2) position bag below bladder", "secure tubing to sheets with clip", "(3) document insertion date", "(4) maintain red seal per hospital policy", "(5) assess need for catheter routinely." Variations on these instructions/procedural indicators or other instructions/procedural indicators are possible. Urine samples may be taken as instructed in FIG. 14D. Ultimately, the catheter may be removed as instructed in FIG. 14C.

The catheterization package(s) and catheterization tray(s) described herein made be manufactured/packaged in different ways. For example, a manufacturer or vendor of catheterization packages may vary the steps or procedures described herein, may reorder the steps, may perform additional steps beyond those described, and/or may omit certain steps as circumstances and unique needs may require. Further, any features, components, arrangements, designs, ordering of components, etc. described above (e.g., features or arrangements that make using the catheterization package more intuitive or logical) may be added to or included in the catheterization package during manufacturing, e.g., in a method of manufacturing/packaging. However, non-limiting, methods of manufacture/packaging are described below. The steps described herein may be done in order as described or out of order.

In one embodiment, a catheterization package is manufactured/packaged by providing a catheterization tray (e.g., a catheterization tray similar to or including features of those shown in FIGS. 1-5 and described above). The tray may be purchased or formed by the manufacturer of the catheterization package. If manufactured, the tray may be formed using an injection molding process or other suitable processes. Instructions/procedural indicators may be integrated on, printed, or otherwise included on the tray as described above and as shown, for example, in FIGS. 1, 2, and 5.

Various components (e.g., any of the components discussed above or elsewhere herein) may be added to the tray. In one embodiment, a pre-connected drainage system may be added to/included in the tray, e.g., in the main compartment 1 as shown in FIG. 26. The drainage system may include a drainage/collection bag 96, drainage tubing 95, a catheter 92 (e.g., a Foley catheter), a drainage outlet, a urine meter, or other drainage components. Swabs or swabsticks 34 may be added to/included in the tray, e.g., in the swab compartment 3 as shown in FIG. 8 or FIG. 26. A specimen or sample container 54 and a label that can be filled out with details regarding the sample and adhered to the specimen or sample container may be added to/included in the tray, e.g., in the corner storage compartment 5 as shown in FIG. 26. A packet or container of an antiseptic skin cleanser 52 (e.g., a packet or container of povidone-iodine solution) may be added to/included in the tray, e.g., in the swab compartment 3 on top of the swabsticks 34 as shown in FIG. 25. A packet or container of lubricant 89 (e.g., a syringe of lubricating jelly) may be added to/included in the tray, e.g., in the syringe or catheter compartment 2 as shown in FIG. 26. A syringe of sterile liquid 88 (e.g., a 10 cc syringe of sterile water for inflating the retention balloon of the Foley catheter) may be added to/included in the tray, e.g., in the syringe or catheter compartment 2 on top of or partially on top of the syringe of lubricating jelly 89 as shown in FIG. 26. A fenestrated drape to place on patient may be added to/included in the tray, e.g., on top of other components, and may span portions of more than one compartment as shown in FIG. 24. An underpad to place under the buttocks of a patient (e.g., a waterproof absorbent underpad) may be added to/included in the tray, e.g., on top of the fenestrated drape or other components, and may span portions of more than one compartment. Both the underpad and fenestrated drape are represented in the figures by pad/drape 86. Gloves (e.g., a package 58 of rubber gloves, latex gloves, latex-free gloves) may be added to/included in the tray, e.g., on top of the underpad or other components and may span portions of more than one compartment as shown in FIG. 22.

Figure 13:
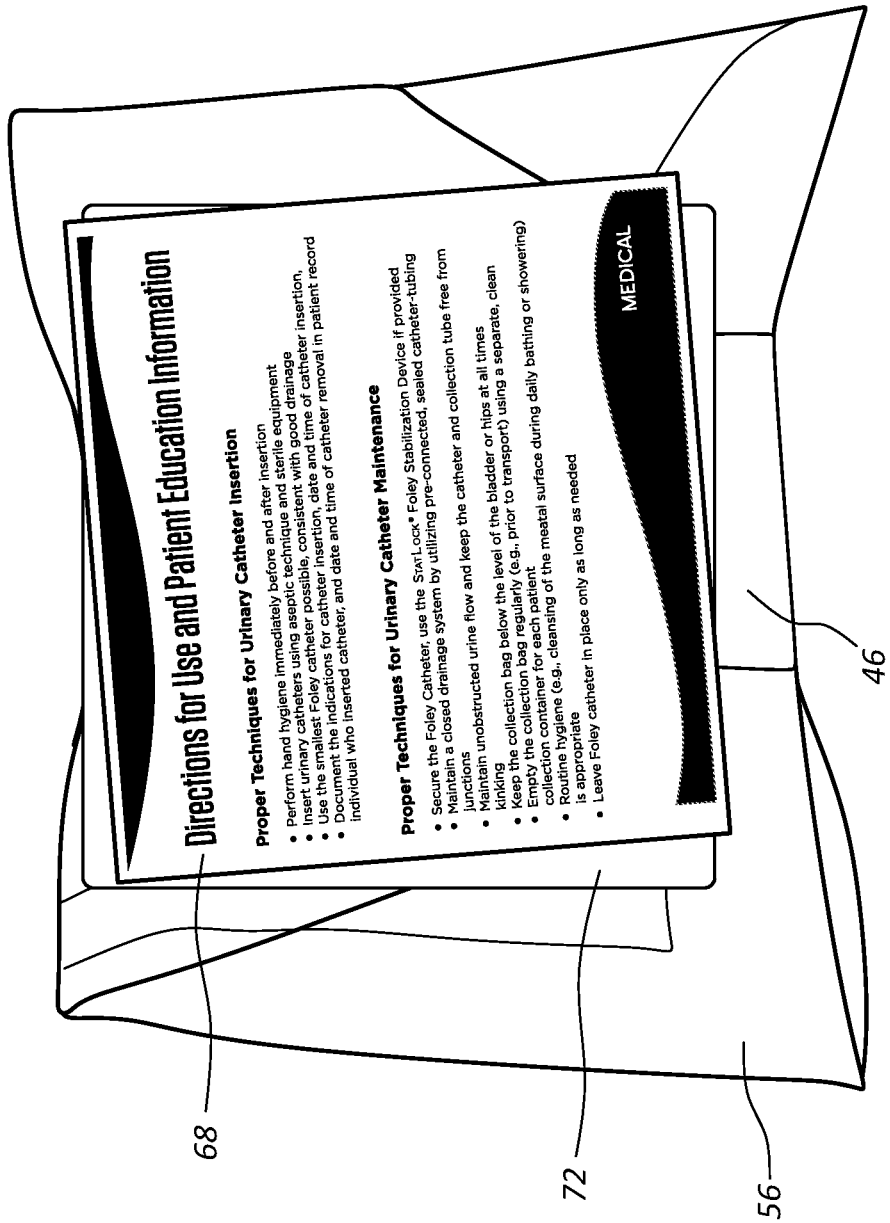
FIG. 13 shows a top view of a catheterization package (e.g., either the catheterization package of FIG. 9 or FIG. 10) after the sealed bag and packaging label have been removed, and showing detailed instructions/procedural indicators document or directions for use (DFU) document thereon.
Figure 14B:
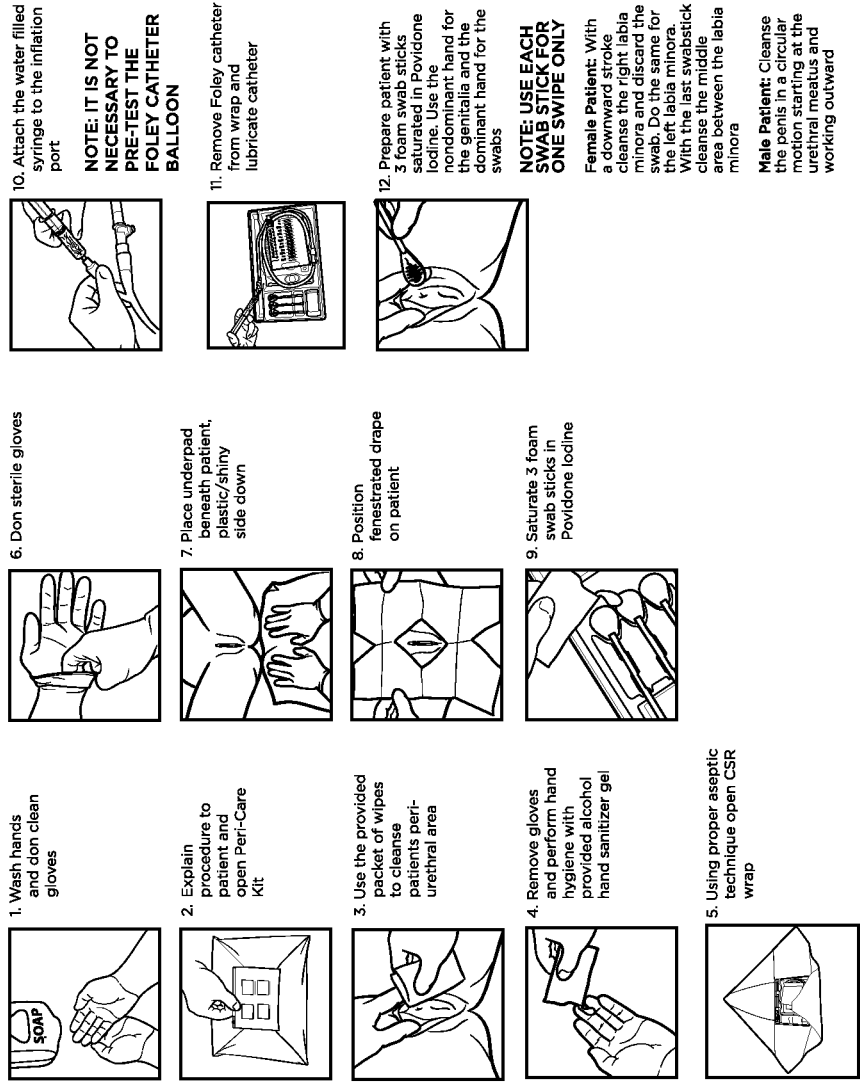
FIG. 14B shows another page of the document of detailed catheterization instructions/procedural indicators or directions for use (DFU) document of FIG. 14A.
Figure 14C:
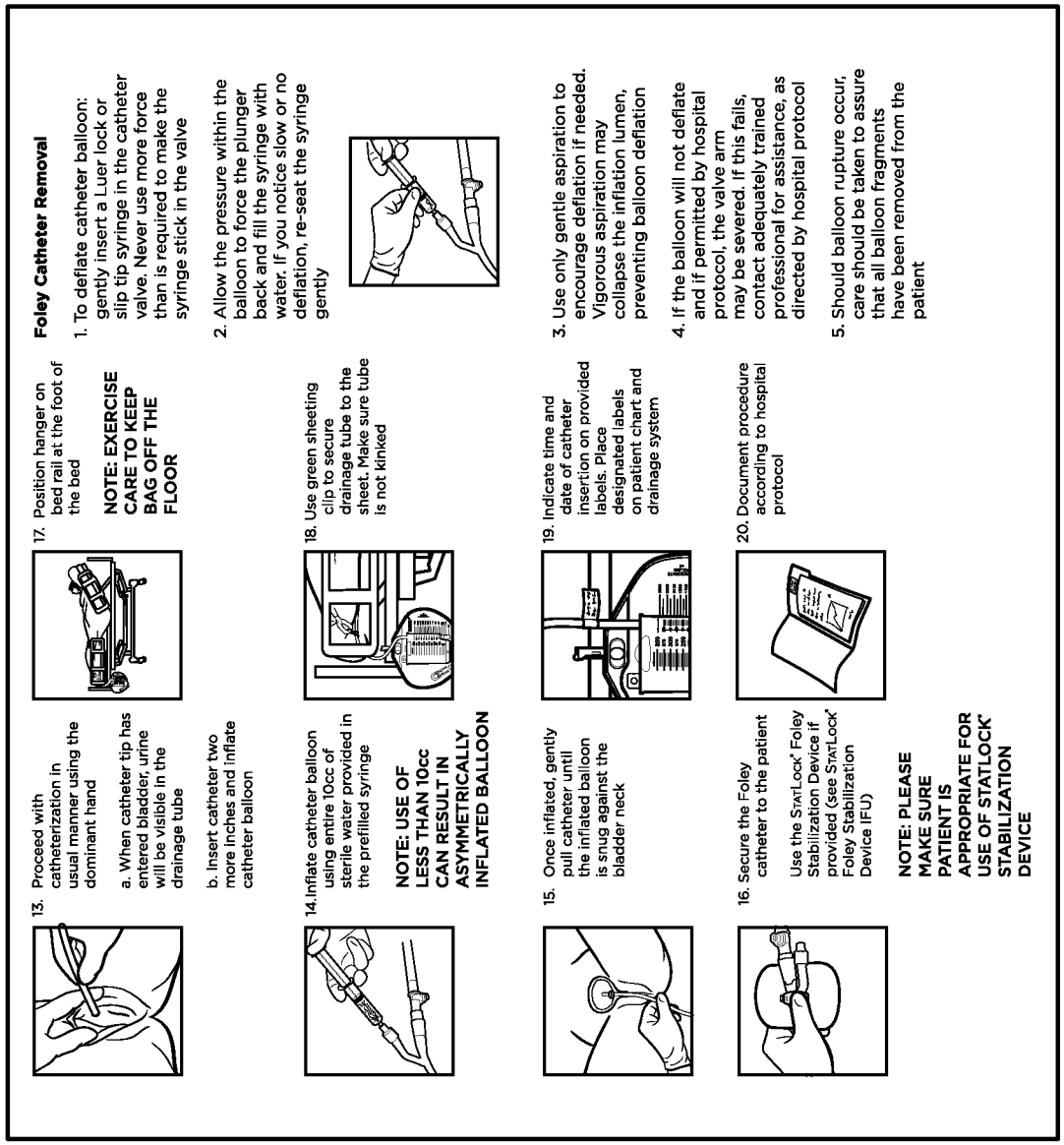
FIG. 14C shows another page of the document of detailed catheterization instructions/procedural indicators or directions for use (DFU) document of FIG. 14A.
Figure 14D:
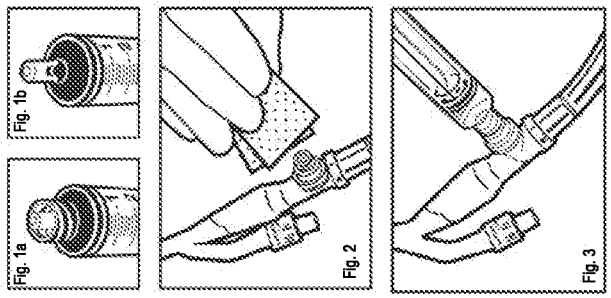
FIG. 14D shows another page of the document of detailed catheterization instructions/procedural indicators or directions for use (DFU) document of FIG. 14A.

The tray and components may be sterilized, and a sterile wrap 56 (e.g., a CSR wrap) may be folded or wrapped around the catheterization tray as shown in FIGS. 20-21. A belly band 46 (e.g., to hold the sterile wrap in a folded configuration and help to keep all the contents inside the tray, so the items do not move around) may be included around the sterile wrap 56 as shown in FIG. 20. A perineal care (or peri-care) packet or kit 74 (e.g., as shown in FIGS. 17-19) may be added to/included in the catheterization package, e.g., placed over the belly band 46 and/or sterile wrap 56 as shown in FIGS. 17 and 18. The perineal care packet or kit 74 may include hand sanitizer 76 (e.g., antiseptic gel hand rinse), moist towelettes 78 (e.g., a package of castile soap towelettes), instructions 80 (e.g., instruction for health care provider and/or instructions for patient), and/or other components (see e.g., FIG. 19). An insert sheet or label 72 with instructions or other information may be added to/included in the catheterization package, e.g., an insert sheet or label 72 with a checklist of safety considerations/steps and/or a patient information chart may be included on top of the perineal care packet or kit as shown in FIG. 16. A detailed instructions document (e.g., as shown in FIGS. 14A-14D) and/or patient educational information (e.g., as shown in FIGS. 15A and 15B) may be added to/included in the catheterization package, e.g., a directions for use (DFU) document 68 and/or a patient educational pamphlet 70 may be included on top of the insert sheet as shown in FIG. 13. A packaging label 62 (e.g., a packaging label as described above and shown in FIGS. 9-12) may be added to/included in the catheterization package, e.g., on top of all the other components and with edges folding down to cover the sides of the catheterization tray. The catheterization package may be sterilized and sealed, e.g., in sealed container or bag 60 as shown in FIGS. 9 and 10. Other components useful to catheterization or care may also be included.

In one embodiment, a catheterization system may include a ureteral catheter assembly and/or materials or supplies (e.g., catheterization elements or components, such as sanitizer liquid, lubricant, inflation liquid, gloves, etc.) suitable or necessary for a ureteral catheterization procedure. For instance, the catheterization system may include a catheterization tray that has multiple compartments for housing and/or securing a ureteral catheter assembly (e.g., an assembly including a Foley catheter) as well as other sterile and/or non-sterile catheterization elements, including any of those discussed above. Sterile catheterization elements may be housed in the catheterization tray in a manner that the sterile elements remain uncontaminated by non-sterile catheterization elements.

The catheterization tray may include one or more visual, procedural indicators or instructions that may aid a user during the catheterization procedure. For instance, the procedural indicators may aid the user in orienting the catheterization tray (and catheterization components or elements thereof) relative to a patient, such that the catheterization components and/or elements may be positioned at predictable and suitable or desirable locations and/or orientations relative to the user and/or to the patient. Additionally or alternatively, the procedural indicators may aid the user in sequencing use of the catheterization components and/or removal thereof from the catheterization tray.

As mentioned above, the catheterization tray and system including such tray may facilitate aseptic techniques during a catheterization procedure. In one embodiment, as shown in FIG. 30A, catheterization system 100 includes container 110 (e.g., a sealed bag), which may hermetically seal or contain the catheterization tray and catheterization components. For instance, the container 110 may facilitate maintaining sterility of sterile catheterization components. For example, the container 110 may be a plastic bag (e.g., a polyethylene bag). Moreover, the container 110 may include a peelable side 111, which may be detached from a non-peelable side 112 to form an opening in the container 110 (container 60 above may have similar features and properties); the contents located in the container 110 may be removed through the opening.

In one embodiment, the catheterization tray and at least some of the contents thereof (i.e., catheterization components) may be at least partially surrounded or enveloped by an identification cover 120. In one embodiment, the packaging label or identification cover 120 (e.g., similar to packaging label 62 discussed above) may include one or more visual identifiers including key information or variables, such as visual identifiers 121, 122, 123 (e.g., these can be similar to the information squares discussed above), which may provide indication related to the type and/or contents of the catheterization system 100.

For example, the packaging label or identification cover 120 may be fabricated from a sheet-like material, such as paper, cardboard, plastic (e.g., plastic film), etc. The visual identifiers 121, 122, 123 may be configured to convey sufficient information for the user to identify the specific type of the catheterization system 100 and/or contents thereof. For instance, the visual identifier 121 may identify the size of the catheter (e.g., 16 French, etc.). In one example, the visual identifier 122 may indicate that the catheterization system 100 includes a urine meter (which may be attached to the catheter), and/or the visual identifier 123 may indicate that the catheterization system 100 includes a catheter stabilization device (e.g., STATLOCK).

The visual identifiers 121, 122, 123 may be visually separated or isolated one from another. For example, the visual identifiers 121, 122, 123 may include a generally square or rectangular perimeter outline that may delimit or define the outer contours thereof. In other words, the identifying information of the visual identifiers 121, 122, 123 may be contained within the generally rectangular outlines of the visual identifiers 121, 122, 123. Hence, for instance, the user may easily and/or quickly locate the pertinent information of the identification cover 120, to identify and/or select the particular catheterization system 100 suitable for the procedure.

One, some, or all of the visual identifiers 121, 122, 123 may include any visible indications or information that may inform the user about specifics of the catheterization system 100. For example, the visual identifiers 121, 122, 123 may include text, images, symbols, etc. Moreover, the visual identifiers 121, 122, 123 and/or portions thereof may have any suitable color or multiple colors, which may aid the user in identifying and/or distinguishing among the visual identifiers 121, 122, 123. In one embodiment, at least one of the visual identifiers 121, 122, 123 may have a different color than others.

It should be appreciated that the particular contour shape, size, thickness, or combinations thereof, which surrounds or contains the identifying information of the visual identifiers 121, 122, 123 may vary from one embodiment to the next. As such, the visual identifiers 121, 122, 123 may have generally circular, triangular, or polygonal shapes. Furthermore, the identification cover 120 may include any number of suitable materials that may carry the visual identifiers 121, 122, 123 may vary from one embodiment to another. For instance, the visual identifiers 121, 122, 123 may be printed, embossed, or otherwise transferred onto the identification cover 120.

The identification cover 120 may include any number of visual identifiers. In other words, the visual identifiers 121, 122, 123 may be located at any number of suitable locations on the identification cover 120 and/or may be duplicated. For example, the identification cover 120 may include visual identifiers 121, 122, 123 on a major face thereof and on a minor face thereof. In one embodiment, the visual identifiers 121, 122, 123 may be located on one, some, or all visible sides of the catheterization system 100 (e.g., one, some, or all of the visual identifiers 121, 122, 123 may be visible from any side of the catheterization system 100 during storage thereof).

The identification cover 120 may be removable from the catheterization tray. For instance, the identification cover 120 may be generally detached from the catheterization tray (e.g., the identification cover 120 may lie on the catheterization tray and may be secured relative to the catheterization tray by the container 110). Furthermore, as shown in FIG. 30B, removing the identification cover may expose the catheterization tray, which may be wrapped by or into a central supply room (CSR) sterile wrap 130. Accordingly, the CSR sterile wrap 130 may at least temporarily secure components in the catheterization tray.

The CSR sterile wrap 130 may be unwrapped and removed from the catheterization tray and may be used during the catheterization procedure. For example, the CSR sterile wrap 130 may be placed near and/or under the patient to provide at least a partially sterile environment near the site of the catheterization procedure, thereby reducing risk of infections associated with the catheterization procedure. The CSR sterile wrap 130 may be substantially opaque, such that the contents of the catheterization tray and/or locations catheterization components are obscured or not be visible to the user. Optionally, the CSR sterile wrap 130 may be translucent or transparent, such that the user may view and/or visually identify catheterization components contained in the catheterization tray.

The catheterization system 100 may include a belly band or directional indicator wrapper 140, which may provide an indication of relative positioning and/or orientation of the components in the catheterization tray, which may not be visible to the user. For example, the belly band or indicator wrapper 140 may include a direction arrow 141 that may be aligned by the user to point toward the catheter insertion site, which may orient the catheterization tray and catheterization components therein relative to the patient. For instance, orienting the catheterization tray in a manner that aligns the direction arrow 141 in the direction of the insertion site may position the catheterization components and/or elements at least partially sequentially, such that the catheterization elements and/or components to be used earlier in the procedure are located closer to the patient than the catheterization components intended to be used later in the procedure.

In addition, the belly band or indicator wrapper 140 may include a warning indicator 142 to alert the user to proper aseptic technique for the catheterization procedure. For example, the warning indicator 142 may include one or more specific elements identifying the particular steps suitable or necessary for proper aseptic procedure. In one embodiment, the warning indicator 142 identifies one or more of the following steps: (1) open CSR sterile wrap 130; (2) don sterile gloves; (3) place underpad; (4) place fenestrated drape; or (5) follow steps identified by procedure indicators located inside the catheterization tray.

While the indicator wrapper 140 may wrap around the CSR sterile wrap 130, this disclosure is not so limited. For example, a sticker or an adhesive label may be attached to the CSR sterile wrap and may include the same or similar indicators as the indicator wrapper 140. Alternatively or additionally, the indicators may be placed directly onto the CSR sterile wrap 130 (e.g., may be printed, embossed, or otherwise transferred thereto).

Figure 31A:
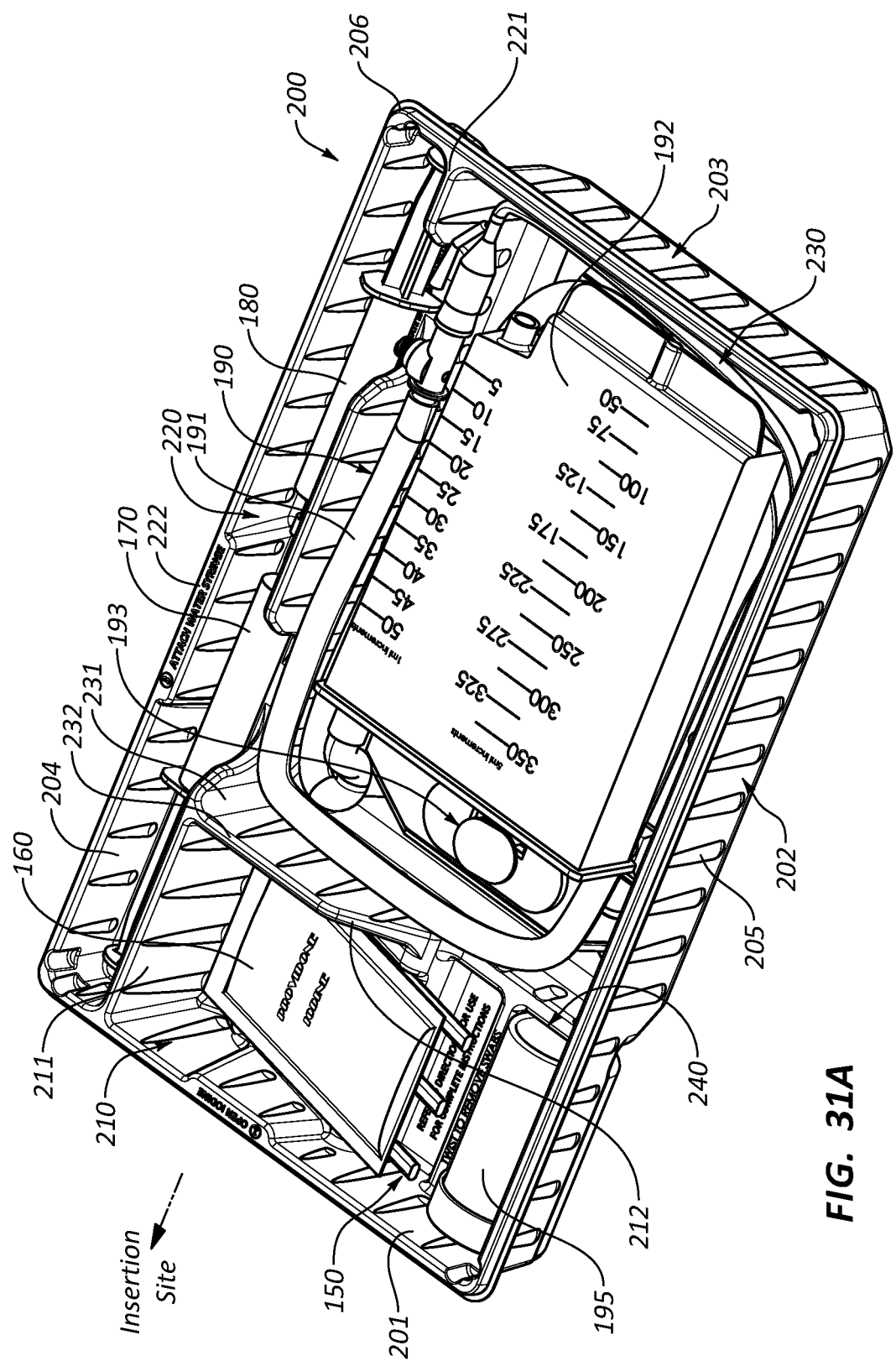
FIG. 31A is an isometric view of a catheterization tray with contents thereof.

After the CSR sterile wrap 130 is removed or unwrapped from the catheterization tray, the contents of the catheterization tray may be exposed. FIG. 31A illustrates a catheterization tray 200 of the catheterization system 100. The catheterization tray 200 may include multiple compartments that may secure or house various catheterization components. The shape and size of the catheterization tray 200 may be defined by the sides thereof. For instance, sides 201, 202, 203, and 204 may define an approximately rectangular outer shell or exterior perimeter of the catheterization tray 200.

The catheterization tray 200 may be molded (e.g., injection molded, thermoformed) or stamped (e.g., from a plastic material). Hence, the sides 201, 202, 203, and 204 may be formed from a sheet-like material. One or more of the sides 201, 202, 203, or 204 may include stiffening ribs 205, which may provide rigidity and/or stiffness to the sides 201, 202, 203, 204. The stiffening ribs 205 may have an approximately tapered shape and/or may protrude outward from the respective sides 201, 202, 203, or 204. More specifically, for example, lower portions of the stiffening ribs 205 (portions closer to the bottom/floor of the catheterization tray 200) may protrude out of the respective sides 201, 202, 203, or 204 more than the upper portions of the stiffening ribs 205 (portions closer to the opening of the catheterization tray 200). At least a portion of one, some, or all of the stiffening ribs 205 may have a partially conical shape.

The catheterization tray 200 may include a swab compartment 210, which may include one or more swabs 150 therein. Additionally or alternatively, the compartment 210 may include a cleansing/sanitizing solution or sanitizer packet 160, which may contain one or more sanitizing agents or cleansing/sanitizing solutions (e.g., containing povidone-iodine solution). The compartment 210 may be positioned near and at least partially defined by the side 201 of the catheterization tray 200. In some instances, the exterior of the sanitizer packet 160 may be non-sterile. Hence, the cleansing/sanitizing solution or sanitizer packet 160 may be placed inside another packaging or a bag, which may have a sterile exterior that may prevent or reduce contamination of other catheterization components in the catheterization tray 200 from the unsterilized packet 160 of cleansing solution or sanitizer. The plastic bag may include a zipper or similar mechanism that may be operated by the user to open and access the packet 160 and/or other components therein.

Catheterization instructions may include images and description of various steps or acts taken during the catheterization procedure. In some instances, instructions also may identify specific step or act numbers, thereby suggesting a particular sequence of steps or acts for the catheterization procedure. Catheterization instructions, which may be non-sterile, may be placed into a sterile container, such as a plastic bag, thereby isolating or separating the non-sterile instructions from sterile catheterization components in the catheterization tray 200. Also, in some examples, the catheterization system may include multiple sets of catheterization instructions, which may improve compliance with aseptic catheterization procedures. For example, catheterization instructions may could be attached or adhered to (e.g., as a sticker) inside the sterile plastic bag and/or to another catheterization element or component (e.g., to the sterile container with the sanitizer packet 160), to an exterior sleeve or portion of the catheterization system, etc.

The compartment 210 may be configured to contained sanitizing substance (e.g., liquid), which may be dispensed in the compartment 210 from the sanitizer packet 160. For example, as described below in more detail, the compartment 210 may have a slanted bottom/floor, such that the cleansing or antiseptic solution (e.g., povidone-iodine solution) or sanitizer from the packet 160 may pool near and/or at a lowermost corner between a bottom/floor and a side (e.g., partition 211) of the compartment 210. Furthermore, tips of the swabs 150 may be located at or near the lowermost corner between the bottom/floor and the side of the compartment 210, such that the tips of the swabs 150 are positioned in the dispensed sanitizing liquid.

The compartment 210 may be at least partially defined by a portion of the side 201 or inner wall thereof, the partition 211, by a partition 212, and by the slanted bottom/floor. For instance, the lowermost portion of the compartment 210 may be located at the corner edge formed by and between the partition 211 and the slanted bottom/floor. Hence, positioning the tips/absorbent heads of the swabs 150 near the slanted bottom/floor and/or near the partition 211 of the compartment 210 may locate the tips/absorbent heads of the swabs 150 at or near the lowermost portion of the compartment 210.

As described above, the catheterization tray 200 may be oriented relative to the patient in a manner that places the side 201 and the compartment 210 closer to the insertion site than the side 203 of the catheterization tray 200. In other words, orienting the catheterization tray 200 based on the direction arrow of the directional indicator wrapper (while the contents and compartments of the catheterization tray 200 are concealed or covered by the CSR sterile wrap 130 (FIG. 30B) may place the side 201 and the compartment 210 near the insertion site. In some instances, the insertion site may be first sterilized with the swabs 150 that may be saturated with the sanitizing liquid from the sanitizer packet 160. As such, positioning the compartment 210 together with the swabs 150 and sanitizer packet 160 near the insertion site may reduce spillage of the sanitizer liquid (e.g., onto one or more catheterization components in the catheterization tray 200) and/or contamination of the swabs 150, which may lead to contamination of the insertion site.

As described below in more detail, the compartment 210 may have a slanted bottom/floor. For instance, an upper edge (or surface), such as an upper edge 206 of the catheterization tray 200 may lie in an imaginary plane that may be approximately parallel to a support surface that may support the catheterization tray 200 (e.g., surface of the patient's bed). The slanted bottom/floor of the compartment 210 may have a non-parallel orientation relative to the imaginary plane of the upper edge 206 and/or to the support surface.

Furthermore, the bottom/floor of the compartment 210 may be non-parallel relative to bottoms/floors of one or more other compartments in the catheterization tray 200. For example, the catheterization tray 200 may be set on the support surface, such that bottoms/floors of one or more compartments support and/or orient the catheterization tray 200 on the support surface. Hence, as described above, the bottom/floor of the compartment 210 may have a non-parallel orientation relative to the support surface.

The catheterization tray 200 may include a side compartment 220. For example, the compartment 220 may extend along substantially an entire side or length of the catheterization tray 200 (e.g., the compartment 220 may extend between the sides 201 and 203 and/or may be partially defined thereby). Hence, in some instances, one side of the compartment 220 may be defined by a side such as by the side 204.

The compartment 220 may contain any number of suitable elements or components of the catheterization kit. For example, the compartment 220 may contain a syringe 170 with liquid that may be used for inflating a balloon of the catheter (described below) and/or a syringe 180 that may contain lubricant. As such, the width of the compartment 220 may be sufficient to accommodate the syringes 170, 180. In some instances, the syringes 170, 180 may be oriented lengthwise along the compartment 220, and may lie in a single row, one in front of the other therein.

The catheterization tray 200 may include one or more cutouts or recesses in a partition 221, which may separate the compartment 220 from an adjacent compartment(s) (e.g., from a catheter compartment 230). For example, one or more recesses in the partition 221 may have top edges thereof located below the upper edge 206 of the catheterization tray 200. More specifically, in some instances, the recesses may provide access to one or more of the syringes 170, 180 from the compartment 230. Hence, a user of the catheterization kit may remove the syringe 170 and/or syringe 180 by reaching into the compartment 230, in lieu of or in addition to reaching into the compartment 220.

In one embodiment, the syringes 170 and 180 may be differently sized. Hence, in one embodiment, at least a portion of the compartment 220 may be narrower than another portion thereof, to accommodate syringes 170, 180 of different sizes. For example, compartment 210 may include a narrowing protrusion 222, which may extend into the space of the compartment 220, thereby narrowing a portion of the compartment 220. For instance, the syringe 170 may have a smaller diameter or peripheral size than the syringe 180. Hence, the narrowing protrusion 222 may narrow the width of the (s) of the compartment 220 may be sufficiently wide to accommodate the syringe 180 (e.g., the narrowing protrusion 222 may prevent or limit lateral movement of the syringe 170 in the compartment 220).

As mentioned above, the catheterization tray 200 may include the main or catheter compartment 230. The compartment 230 may have an approximately rectangular shape. For example, the compartment 230 and the shape thereof may be at least partially defined by the side 203, at least a portion of the side 202, and by partitions 212, 221. While in one embodiment the compartment 230 may have a generally rectangular shape, it should be appreciated that the shape of the compartment 230 may vary from one embodiment to the next.

In any event, the compartment 230 may be sized (e.g., perimeter dimensions and depth), shaped, or otherwise configured to contain or house a catheter assembly 190. For instance, the catheter assembly 190 may include a catheter 191 that may be connected to a urine collection bag and/or urine meter 192. In some instances, the compartment 230 also may contain or house a STATLOCK 193, which may secure at least a portion of the catheter assembly 190 during the catheterization procedure.

The compartment 230 may have an approximately flat or planar bottom/floor, as described below in more detail. For example, the bottom/floor of the compartment 230 may support the catheterization tray 200 on the support surface. Hence, in one embodiment, the bottom/floor of the compartment 210 may have a non-parallel orientation relative to the bottom/floor of the compartment 230.

As mentioned above, the compartment 230 may have an approximately rectangular shape. Furthermore, the compartment 230 may have rounded or chamfered interior corners 231 between the inner walls that define the perimeter of the compartment 230. Additionally or alternatively, the upper portions of the inner walls and/or partitions may have one or more chamfers or fillets 232, which may extend at least partially along their respective lengths.

The catheterization tray 200 also may include an auxiliary compartment 240 that may contain or house an auxiliary container 195 (e.g., a specimen or sample container). For instance, the auxiliary container 195 may be approximately cylindrical and may include a cap. Furthermore, the compartment 240 may be shaped, sized, and configured to secure the auxiliary container 195 therein. In one embodiment, the length of the compartment 240 may be similar to the length of the auxiliary container 195 (e.g., the compartment 240 may include a small clearance or may have an interference fit with the auxiliary container 195). In one embodiment, the bottom/floor of the compartment 240 may be semi-cylindrical or generally arcuate and may approximately follow the general cylindrical shape of the auxiliary container 195. Hence, for instance, the bottom/floor of the compartment 240 may at least partially wrap around the auxiliary container 195.

Figure 31B:
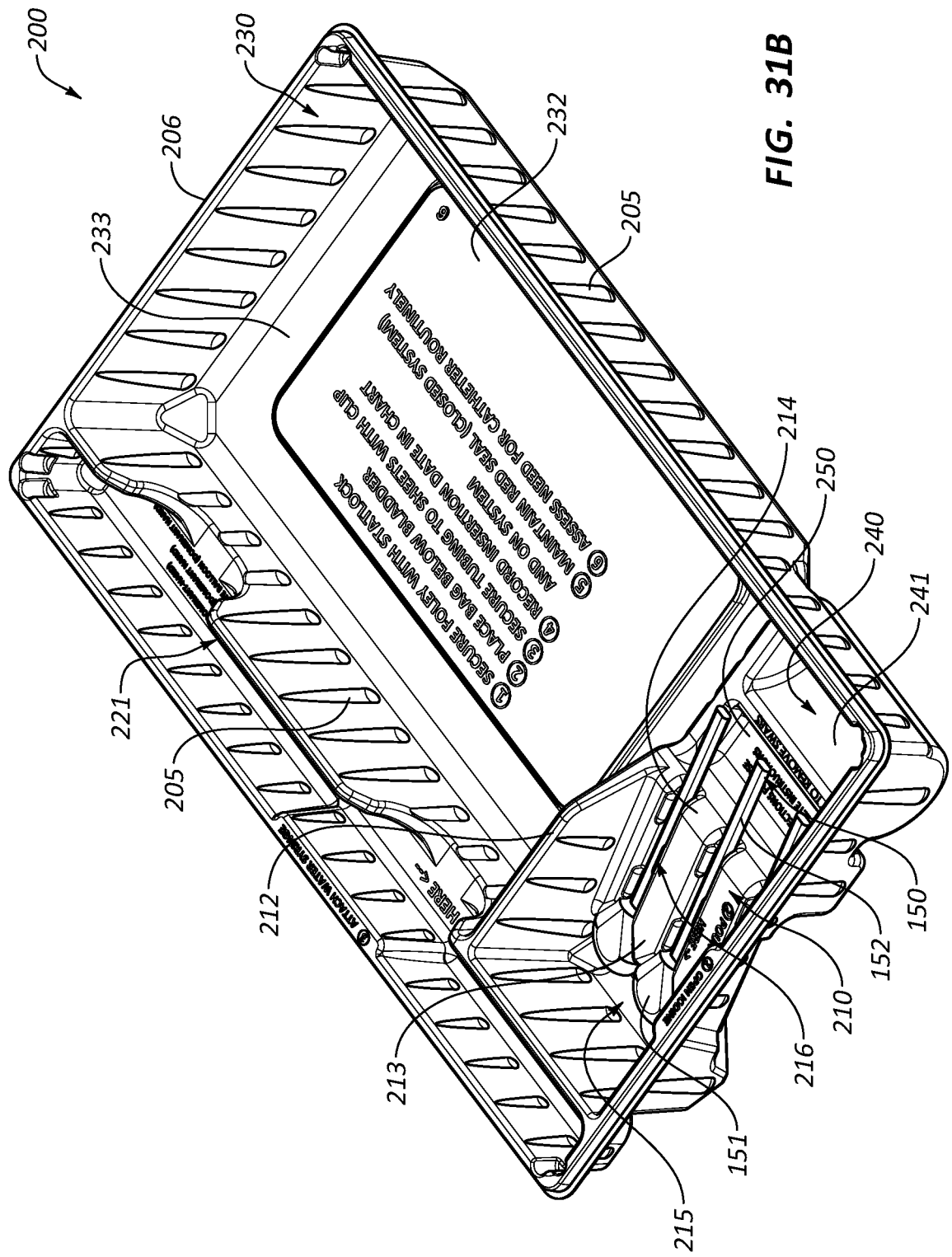
FIG. 31B is an isometric view of the catheterization tray of FIG. 31A with some of the contents thereof removed therefrom.

For example, as shown in FIG. 31B, the compartment 240 may have a partially rounded bottom/floor 241. The compartment 240 may be separated from the compartment 210 in the catheterization tray 200. For instance, the catheterization tray 200 may include an overflow cavity 250 located between the compartment 240 and the compartment 210. In one embodiment, the overflow cavity 250 may form a recess or depression between the compartment 210 and the compartment 240. For example, the overflow cavity 250 may prevent or limit overflow of the sanitizing liquid dispensed into the compartment 210. Moreover, the user may tap excess sanitizing liquid from the tips of the swabs 150 into the overflow cavity 250, before applying the sanitizing liquid at or near the insertion site.

The slanted bottom/floor 213 of the compartment 210 may be elevated or stepped above the overflow cavity 250. For example, the slanted bottom/floor 213 may terminate at a fillet or radius 214 that may extend from the slanted bottom/floor 213 downward toward the overflow cavity 250 or an edge thereof. The radius 214 may provide a transition between the slanted bottom/floor 213 and at least a portion of the overflow cavity 250 located below the slanted bottom/floor 213. In any event, the slanted bottom/floor 213 may slant downward and away from the overflow cavity 250.

As mentioned above, sanitizing liquid may be dispensed at the lowermost portion 215 of the compartment 210 (e.g., at or near the lowermost portion of the slanted bottom/floor 213). Furthermore, sanitizing liquid dispensed in the compartment 210 may generally flow toward and pool at the lowermost portion 215 of the compartment 210. In addition, the tips 151 of the swabs 150 may be set or positioned in the sanitizing liquid. As such, the user may remove the swabs 150 from the compartment 210 and apply sanitizing liquid at the insertion site without further acts.

The swabs 150 may be secured in the compartment 210 in a manner that positions the tip(s) or absorbent head(s) 151 in the sanitizing liquid dispense in the compartment 210. For example, one, some, or each of the swabs 150 may include an elongated stem/stick 152 and a tip/absorbent head 151 attached to the stem/stick 152. Moreover, the compartment 210 may include channels 216 that may house and secure the elongated stem/stick 152 of the swabs 150. Hence, the stems/sticks 152 of the swabs 150 may be secured in the channels 216 of the compartment 210.

The channels 216 may include one or more retention features (e.g., detents, overhangs), which may secure the stems/sticks 152 therein. For example, the stems 152 may have approximately rectangular or generally rectangular cross-sectional shapes. When the stems/sticks 152 are oriented along the longer side of the rectangular cross-sectional shapes thereof, the retention features may secure the elongated stem 152 in the channels 216. Also, rotating or twisting the swabs 150 in the channels 216 (e.g., such that the shorter side of the rectangular cross-sectional shapes of the stems 152 may be oriented to lie within the channels 216) may disengage the stems 152 from the channels 216.

In other words, spacing between the retention features of the channels 216 may be less than the width of the longer side of the rectangular cross-sectional shape of the elongated stem 152, such that the retention features may restrain the elongated stem/stick 152 in the channels 216. Moreover, the spacing between the retention features may be greater than the length of the shorter side of the rectangular cross-sectional shape of the elongated stem/stick 152. Accordingly, twisting or rotating the swabs 150 within the channels 216 may allow the elongated stem/stick 152 to pass between the retention features of the channels 216 in order to remove the elongated stem/stick 152 therefrom.

The catheterization tray 200 (as well as the catheterization trays shown in FIGS. 1-5) may be fabricated in any number of suitable ways and with any number of suitable manufacturing techniques. As mentioned above, the catheterization tray(s) may be injection molded, thermoformed, or otherwise mass-produced. For instance, the catheterization tray(s) may be fabricated from a sheet of plastic material that may be processed by compressing and heating the sheet into the suitable configuration, as described herein. As such, one or more of the sides of the catheterization tray(s) may comprise a relatively thin plastic material (e.g., 0.005 inch, 0.010 inch, 0.020 inch, 0.050 inch, 0. catheterization system 100 inch, etc.). As described above, the catheterization tray(s) may include stiffening ribs on one or more sides thereof, which may provide rigidity to such sides.

The catheterization tray(s) may include stiffening ribs as described herein on one or more partitions that divide the interior space of the catheterization tray(s) into the compartments described herein. Also, as described below in more detail, the partitions (e.g., the partition 221) may include folded or dual layers of sheet material. The stiffening ribs may protrude away from the compartments (e.g., away from the compartment 210, compartment 220, compartment 230) and into the space between the layers of the sheet material.

As described above, in the compartments, the inside corners and/or edges formed between the bottom/floor and inner walls, sides, and/or partitions may include fillets or chamfers. For example, such fillets or chamfers may reduce stress at the inside corners or edges of the compartments. Accordingly, the fillets and/or chamfers formed at the inside corners and/or edges of the compartments may reduce or prevent breakage or failure of the sheet material that forms the catheterization tray 200.

The bottom/floor of the compartment 230 may be substantially flat. Additionally or alternatively, the bottom/floor of the compartment 230 may have a protruding landing 232 and a recessed portion 233. For example, the recessed portion 233 may be lower or farther away from the upper edge 206 of the catheterization tray 200 than the landing 232. Furthermore, the recessed portion 233 may at least partially or completely wrap around the landing 232. As such, for instance, the recessed portion 233 may accommodate at least a portion of the catheter, which may wrap around the landing 232.

Figure 31C:
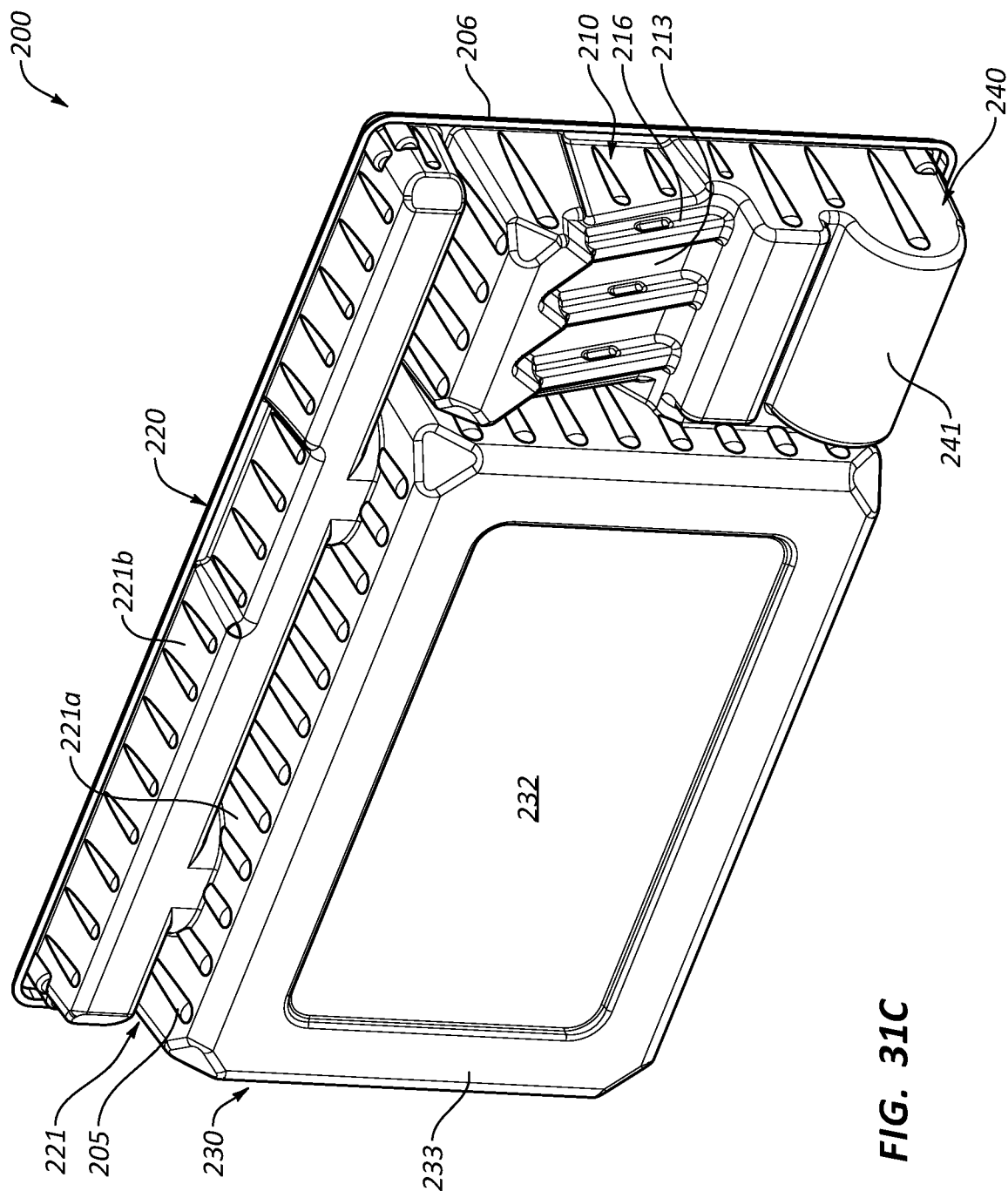
FIG. 31C is a back isometric view of the catheterization tray of FIG. 31A.

As described above, the catheterization tray 200 may be placed on a support surface, such as a surface of the patient's bed. For example, as shown in FIG. 31C the recessed portion 233 of the compartment 230 may form a protrusion on the exterior of the catheterization tray 200, while the landing 232 may form a recesses on the exterior of the catheterization tray 200. As such, the exterior surface of the recessed portion 233 may provide or form a surface that may orient and/or support the catheterization tray 200 on the support surface. Moreover, in one embodiment, the exterior surface of the recessed portion 233 may be approximately parallel to the imaginary plane of the upper edge 206.

Also, as mentioned above, the channels 216 of the compartment 210 may be generally parallel to the slanted bottom/floor 213 and slanted or non-parallel relative to the support surface. The channels 216 of the compartment 210 may have a non-parallel orientation relative to the exterior surface of the recessed portion 233. For instance, on the exterior of the catheterization tray 200, the channels 216 may protrude outward away from the slanted bottom/floor 213.

A compartment of the catheterization tray (e.g., compartment 210) or a portion thereof may carry the sanitizing or cleansing liquid (e.g., povidone-iodine solution) therein. For example, at least a portion of the compartment may carry the sanitizing liquid and may be sealed by a peelable cover. As such, during the catheterization procedure, the user may avoid pouring a sanitizing liquid out of a packet (e.g., into the catheterization tray), which may prevent or reduce spillage of the sanitizing liquid. The swabs may be at least partially submerged in the sanitizing liquid and/or at least partially sealed together therewith by the peelable cover. Alternatively or additionally, the swabs may be located in another compartment of the catheterization tray.

As described above, partitions of the catheterization tray 200 may be formed by two layers of a sheet material. At least some of the partitions may have space between the layers of the sheet material. For example, the partition 221 may include a first layer 221a and a second layer 221b spaced apart from each other (e.g., the first layer 221a may define or form the perimeter of the compartment 230, and the second layer 221b may define or form the perimeter of the compartment 220.

The stiffening ribs 205 on the first layer 221a of the partition 221 may protrude outward, away from the compartment 230 and into the space between the first and second layers 221a, 221b. The stiffening ribs 205 on the second layer 221b may also protrude outward, away from the compartment 220 and toward the outer perimeter or periphery of the catheterization tray 200. In any event, as described above, the compartments of the catheterization tray 200 may have indents that correspond to the protrusions formed on the exterior portions of the catheterization tray 200 by the stiffening ribs 205.

Figure 32:
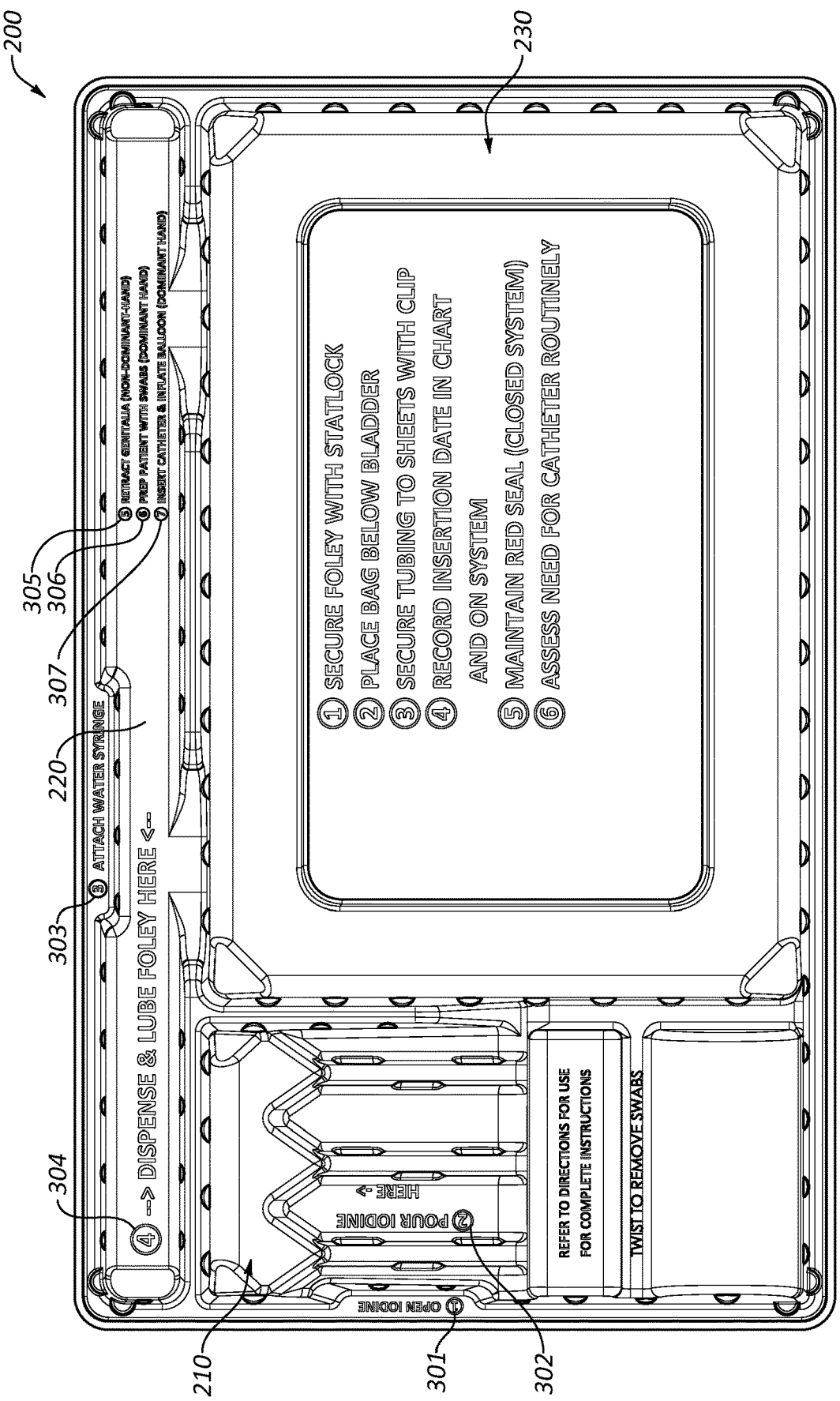
FIG. 32 is a top view of the catheterization tray of FIG. 31A with all of the contents thereof removed therefrom.

The catheterization tray 200 may include one or more instructions or procedural indicators that may assist a user during a catheterization procedure. For instance, as illustrated in FIG. 32, the catheterization tray 200 may include indicators 301-307, which may be printed on the catheterization tray 200. For example, a first indicator 301 may indicate to the user to open the package containing sanitizing liquid, and a second indicator 302 may indicate to the user to pour the sanitizing liquid into the compartment 210, during the catheterization procedure.

A third indicator 303 may indicate to the user to attach to the catheter the syringe containing liquid for inflating the catheter balloon. In one embodiment, a fourth indicator 304 may indicate to the user to dispense lubricant and/or may identify or suggest a location in the compartment 220 for dispensing lubricant. Also, indicators 305-307 may identify additional or alternative steps to take during the catheterization procedure (e.g., retract genitalia (with non-dominant hand), prepare patient with swabs (with dominant hand), insert catheter and inflate balloon (with dominant hand)).

The catheterization tray 200 may include an enlarged or bolded print of the indicators 301-307 for improved visibility. Further, other enlarged instructions/indicators may be printed on the bottom/floor of the compartment 230, as shown in FIG. 32. The presence of the indicators 301-307 on the catheterization tray 200 may obviate or reduce the necessity for printed handouts or similar instructions.

Figure 33:
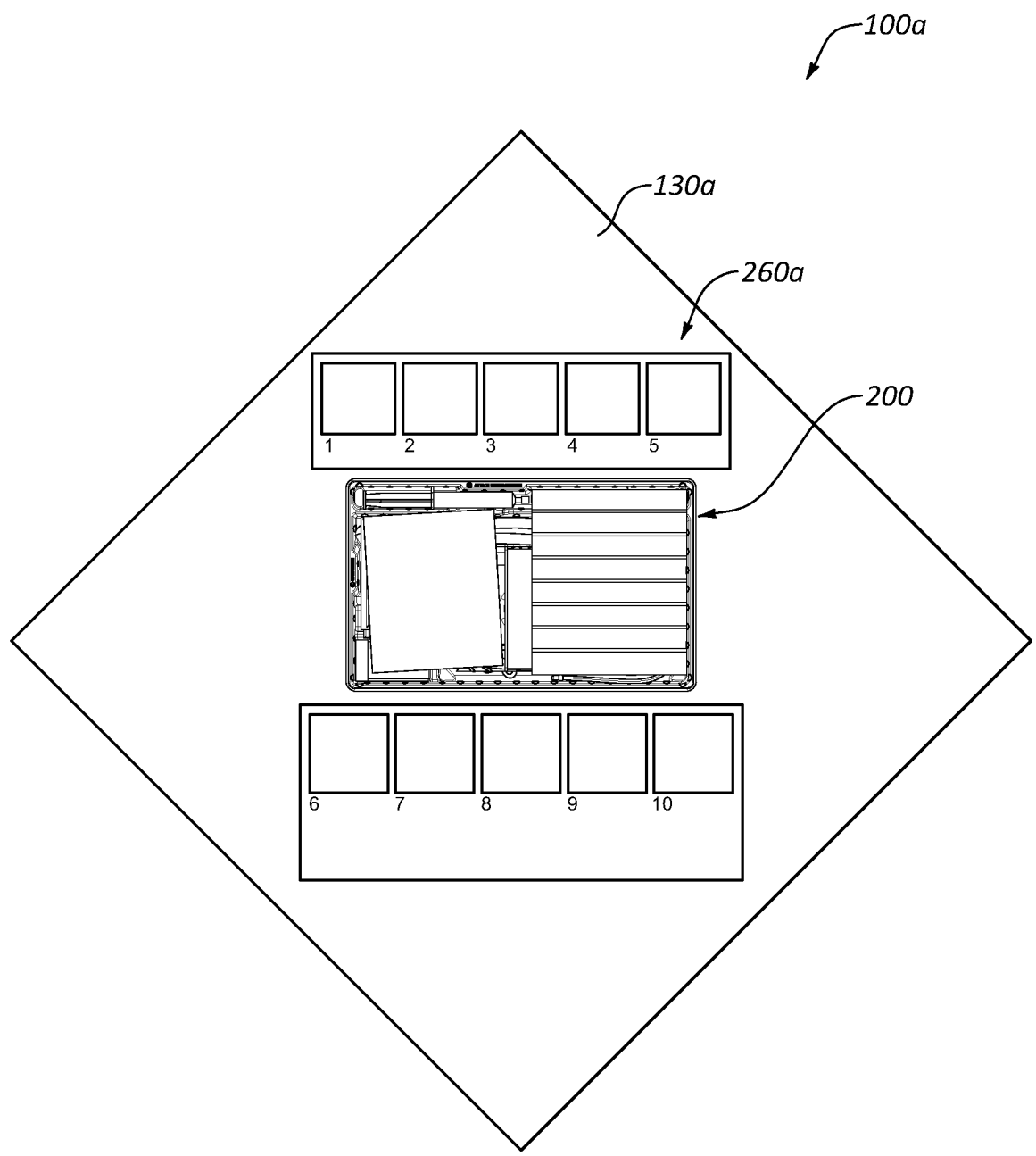
FIG. 33 is a top view of a catheterization system.

In one embodiment, as shown in FIG. 33, a catheterization system 100a may include one or more procedural indicators 260a on a CSR sterile wrap 130a. Except as otherwise described herein, the catheterization system 100a and its elements and components may be similar to or the same as catheterization system 100 (FIGS. 30A-32) and its respective elements and components. For example the catheterization system 100a may include the catheterization tray 200 and catheterization elements and/or components described above in connection with the catheterization tray 200 above.

In one embodiment, the CSR sterile wrap 130a may include one or more procedural indicators 260a that may assist a user during the catheterization procedure. For example, one or more of the procedural indicators 260a may be individually isolated and/or delimited, or otherwise visually enclosed by a perimeter outline. In particular, isolating each of the procedural indicators 260a may draw or focus user's attention thereto and may facilitate identification thereof. The procedural indicators 260a may contain similar or the same information as indicators 301-307 (FIG. 32).

Figure 34:
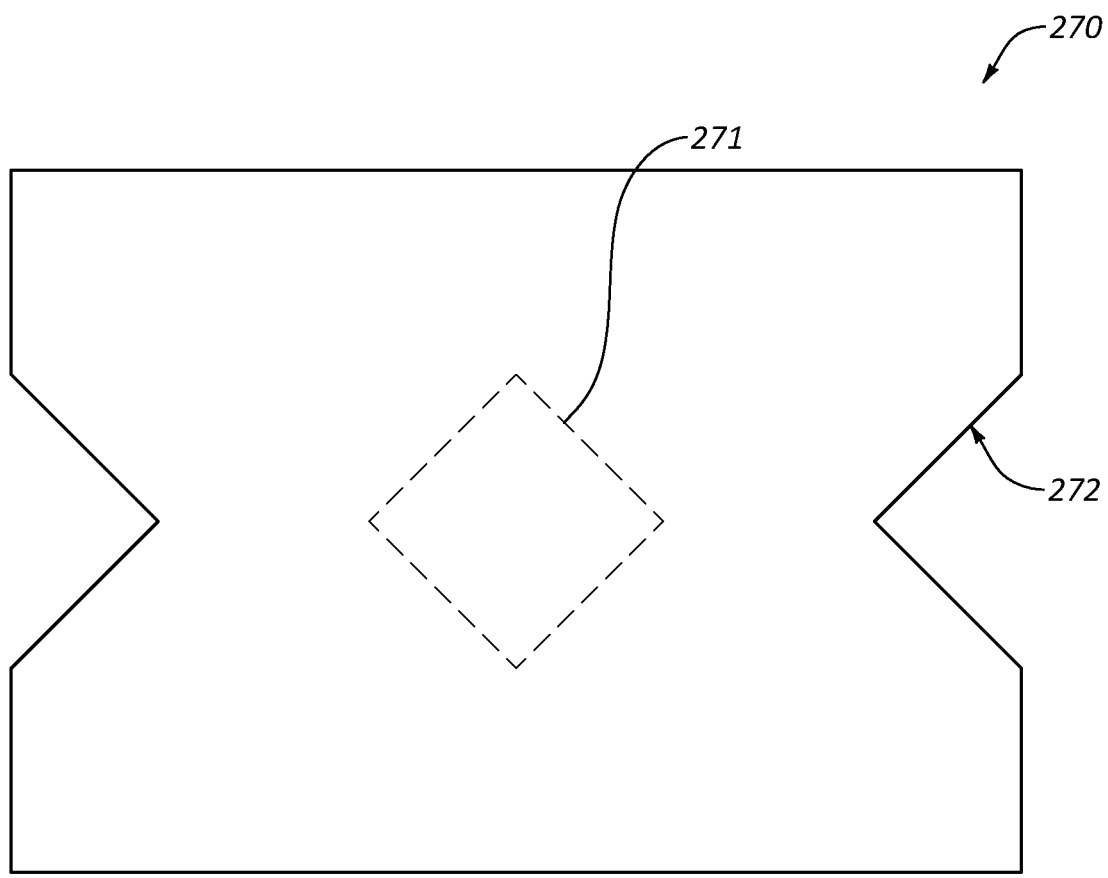
FIG. 34 is a top view of a fenestrated drape.

In one embodiment, the catheterization tray may include a fenestrated drape, which may partially cover the patient and may facilitate insertion of the catheter. FIG. 34 illustrates a fenestrated drape 270. The fenestrated drape 270 may have a generally rectangular shape. Moreover, the fenestrated drape 270 may include perforations 271. In particular, the perforations 271 may generally form a shape of a cutout in the fenestrated drape 270, which may be formed therein by tearing a portion of the fenestrated drape 270 delimited by the perforations 271. In one embodiment, the central portion of the fenestrated drape 270 is already opened, i.e., the central material inside the area circumscribed by perforations 271 is removed prior to packaging the fenestrated drape 270.

The shape defined by the perforations 271 or the shape of the central opening may be suitable for accessing the genitalia of the patient for performing the catheterization procedure after covering the patient with the fenestrated drape 270. Also, in some instances, the fenestrated drape 270 may include side cutouts 272. For instance, the side cutouts 272 may be generally V-shaped. In one embodiment, the side cutouts 272 may facilitate placement of the fenestrated drape 270 about the legs of the patient.

Figure 35:
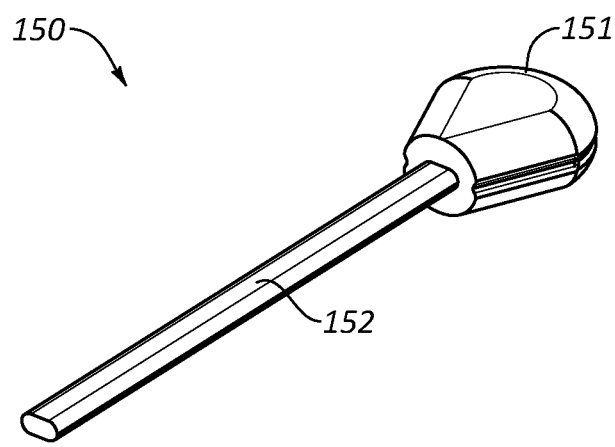
FIG. 35 is an isometric view of a swab.

As mentioned above, the catheterization system may include various components that may facilitate the catheterization procedure, such as swabs that may facilitate sanitizing area near or at the site of the catheterization. FIG. 35 illustrates a swab 150. For example, the swabs 150 may include the elongated member or stem/stick 152 and the tip/absorbent head 151 attached thereto.

The tip/absorbent head 151 may have a generally rounded outward or distal portion and a tapered proximal portion (e.g., tapering toward the proximal end of the tip/absorbent head 151 and toward the elongated stem/stick 152). For example, the tip/absorbent head 151 may be narrower at the proximal end of than at the distal portion (i.e., the distal portion may be generally flared and front edge thereof may be generally rounded).

The tip/absorbent head 151 may include any suitable material, which may vary from one embodiment to the next. The tip/absorbent head 151 may include or comprise liquid absorbing material, which may absorb sanitizing liquid and subsequently dispense the sanitizing liquid onto and/or near the site of catheterization. For instance, the tip/absorbent head 151 may comprise a suitable foam, sponge, cotton, etc.

The tip/absorbent head 151 may be attached to the elongated stem/stick 152 with any number of suitable mechanisms, which may vary from one embodiment to the next. For example, the tip/absorbent head 151 may be attached to the elongated stem/stick 152 with an adhesive, may be ultrasonically welded to the stem/stick 152, etc. The elongated stem 152 may enter into the tip/absorbent head 151 to a predetermined depth, which may facilitate suitably securing together the tip/absorbent head 151 and the elongated stem/stick 152, while leaving a sufficient portion of the tip/absorbent head 151 beyond the elongated stem/stick 152 (e.g., in a manner that avoids contacting and/or injuring or hurting the patient with the elongated stem/stick 152 during application of the sanitizing liquid at the insertion site. For instance, after being secured to the elongated stem/stick 152, the tip/absorbent head 151 may have sufficient flexibility and sufficient resilience and/or stiffness, such that the tip may substantially remain unbent after absorption of the sanitizing liquid and may resiliently bend during application of the sanitizing liquid at the insertion site.

Figure 36A:
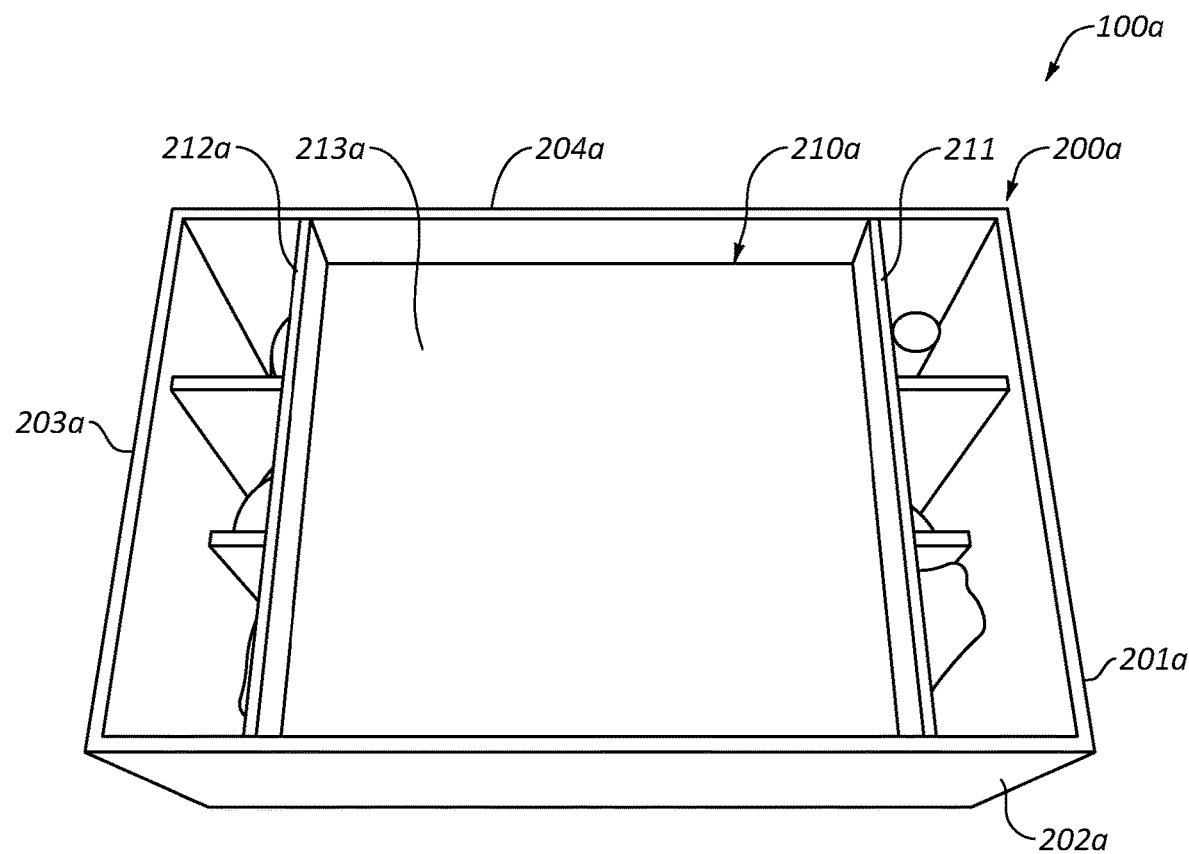
FIG. 36A is an isometric view of a catheterization system.
Figure 36B:
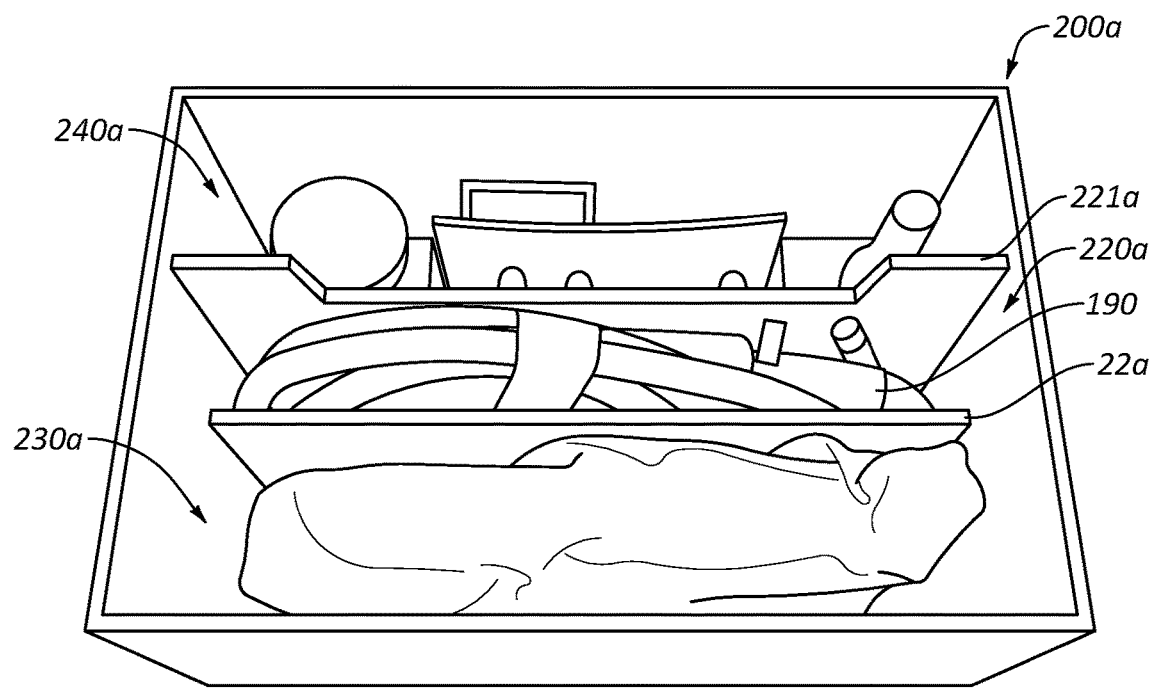
FIG. 36B is an isometric view of a catheterization tray of the catheterization system of FIG. 36A.

As described above, in some examples, the catheter assembly in the catheterization tray may be oriented generally parallel to the support surface that supports the catheterization tray. The catheter assembly in the catheterization tray may be generally oriented vertically or perpendicularly to the support surface. FIGS. 36A-36B illustrate a catheterization system 100a that includes a catheterization tray 200a, which secures a catheter assembly and/or one or more components or elements for catheterization procedures. Except as described herein, the catheterization system 100a and its elements and components may be similar to or the same catheterization system 100 (FIG. 30A) and its elements or components. For instance, except as described herein, the catheterization tray 200a and catheterization elements and components contained in the catheterization tray 200a may be similar to the catheterization tray 200 (FIGS. 31A-32) and catheterization elements or components contained therein.

For example, as shown in FIG. 36A, the catheterization tray 200a may have a generally rectangular shape, which may be defined by sides 201a-204a. The sides 201a-204a may be approximately planar, hence, may define a box-like structure or periphery of the catheterization tray 200a. The catheterization tray 200a also may include a top compartment 210a that may contain instructions and/or one or more catheterization components. In one embodiment, the top compartment 210a may be defined by partitions 211a, 212a and a bottom 213a. In one embodiment, the partitions 211a, 212a, and/or the bottom 213a may be removable from the catheterization tray 200a.

In one embodiment, removal of the partitions 211a, 212a, and/or the bottom 213a may provide access to additional catheterization components contained in the catheterization tray 200a. For example, as shown in FIG. 36B, after removing the partitions 211a, 212a, and the bottom 213a (FIG. 36A), a center compartment 220a of the catheterization tray 200a may be exposed and/or accessible to the user. For instance, the compartment 220a may house or contain catheter assembly 190. In one embodiment, the compartment 210a may be separated from adjacent compartments by one or more partitions (e.g., by partitions 221a, 222a). As mentioned above, the catheter assembly 190 in the compartment 210a may be oriented approximately vertically relative to the support surface (e.g., when the catheterization tray 200a is placed on the support surface, such as a surface of the patient's bed).

In one embodiment, the partitions 221a, 222a may separate the center compartment 220a from adjacent compartments 230a, 240a. Compartments 230a and/or 240a may house or contain various catheterization elements or components for procedure, which may be similar to or the same as catheterization components described above in connection with catheterization tray 200 (FIGS. 31A-32). In some instances, the partitions 221 and/or 222a may be removable from the catheterization tray 200a, which may facilitate removal of catheterization elements or components from the catheterization tray 200a.

The catheterization tray 200a may be constructed of any suitable material. For example, the catheterization tray 200a may be constructed of thick sheet-like material or panels (e.g., plastic material). For instance, thickness of the panels may be in one or more of the following ranges: about 0.1 inches to about 0.2 inches; about 0.15 inches to about 0.3 inches; about 0.25 inches to about 0.5 inches. It should be appreciated, however, panel thickness may be less than 0.1 inches or greater than 0.5 inches. Moreover, the catheterization tray 200a may be reused after the catheterization procedure (e.g., the catheterization tray 200a may be sanitized and/or repacked for reuse).

Figure 37A:
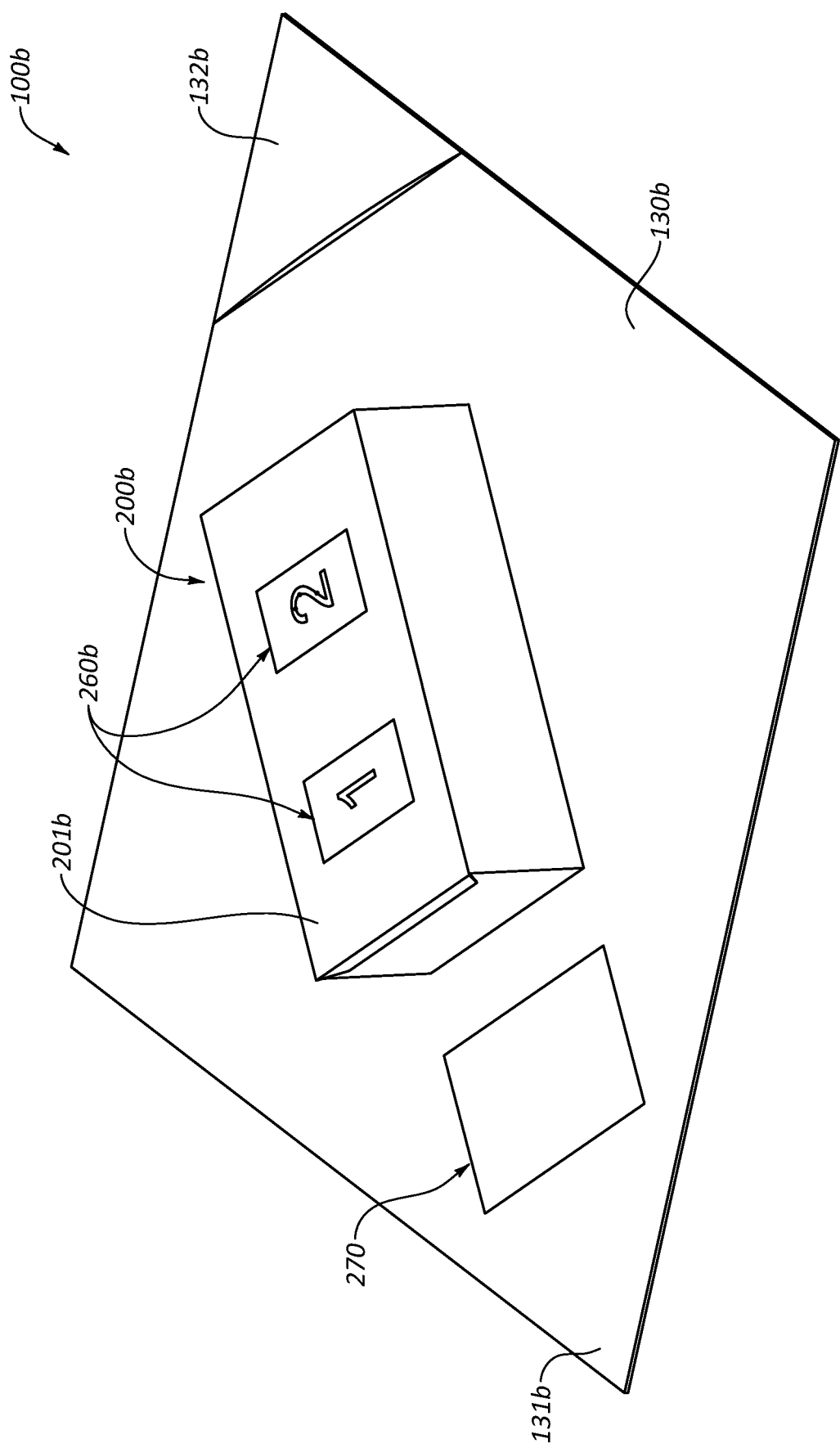
FIG. 37A is an isometric view of a catheterization system.

In one embodiment, the catheterization tray may be at least partially disassembled (e.g., in addition to or in lieu of removing partitions). FIG. 37A illustrates a catheterization system 100b that may include a catheterization tray 200b, which may be unfolded to access contents therein. As mentioned above, the catheterization system 100b may include a catheterization tray 200b that may be wrapped in a CSR sterile wrap 130b, which may be unwrapped to access the catheterization tray 200b. For instance, initially a flap or portion 131b of the CSR sterile wrap 130b may be unfolded toward the patient (e.g., thereby covering the support surface with the sterile portion 131b of the CSR sterile wrap 130b.

In one embodiment, the CSR sterile wrap 130b may include a pocket 132b, which may be exposed when the CSR sterile wrap 130b is unwrapped to expose the catheterization tray 200b. In one embodiment, during and/or after the catheterization procedure, used items or trash may be placed in the pocket 132b. Subsequently, the trash may be disposed together with the CSR sterile wrap 130b.

A drape (e.g., fenestrated drape 270) may be attached to the CSR sterile wrap 130b, such that after the unwrapping the CSR sterile wrap 130b, the drape is exposed and may be removed from the CSR sterile wrap 130b and used in the catheterization procedure. In one embodiment, the fenestrated drape 270 may be attached to the CSR sterile wrap 130b in any suitable manner, which may vary from one embodiment to the next. In one example, the fenestrated drape 270 may be attached to the CSR sterile wrap 130b with light adhesive, tape, tabs, etc.

As mentioned above, the catheterization tray 200b may be exposed after unwrapping the CSR sterile wrap 130b. The catheterization tray 200b may include one or more identifiers 260b, which may identify or suggest an order of step and/or use of catheterization components in the catheterization procedure (e.g., the identifiers may be on one or more outer surfaces of the catheterization tray 200b). For example, the identifiers 260b may be located on the top surface of the catheterization tray 200b and may indicate further steps in the catheterization procedure. According to one embodiment, a top panel 201b of the catheterization tray 200b may be opened to unfold the catheterization tray 200b and access the catheterization components in the catheterization tray 200b.

Figure 37B:
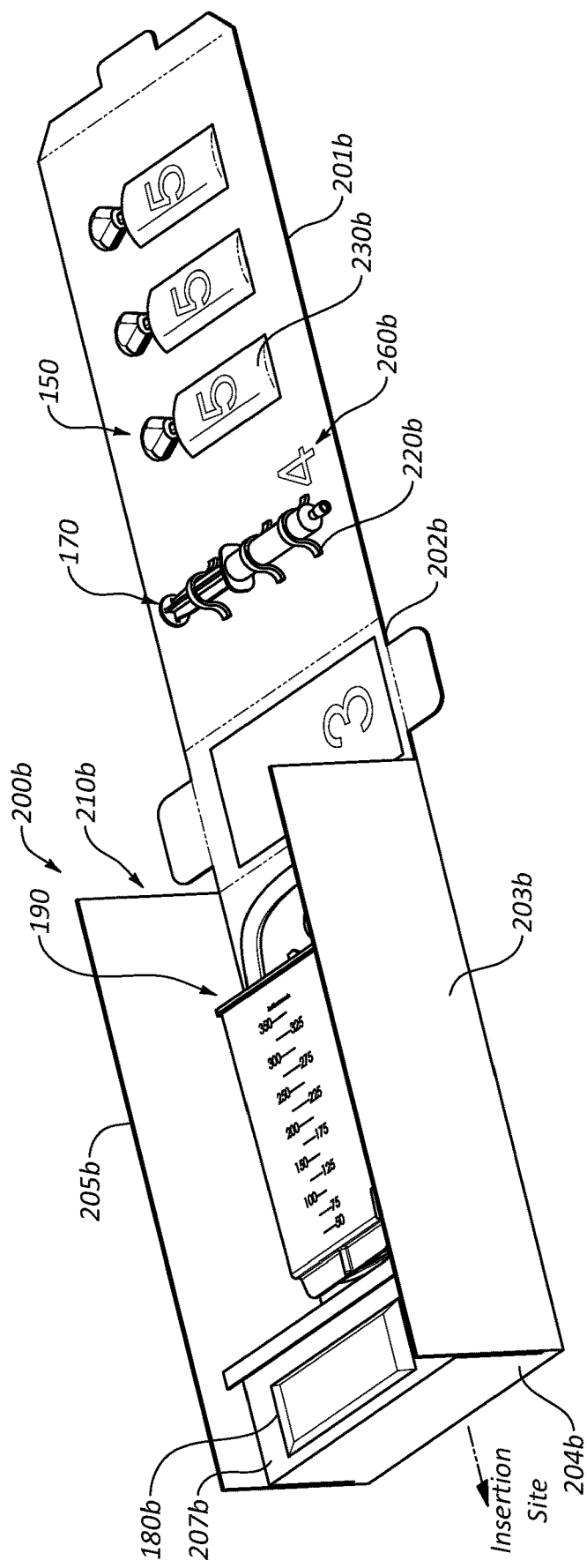
FIG. 37B is an isometric view of a partially unfolded catheterization tray of the catheterization system of FIG. 37A.

As shown in FIG. 37B, after opening the catheterization tray 200b, the user may access the compartment 210b, which may contain the catheter assembly 190 for the catheterization procedure. For instance, the top panel 201b together with a side panel 202b (connected thereto) may be unfolded away from panels 203b, 204b, 205b. More specifically, the side panels 203b, 204b, stiffening ribs 205b may partially define the periphery of the compartment 210b. Unfolding the side panel 202b and the top panel 201b from the side panels 203b, 204b, 205b may provide access to the compartment 210b through a side (from which the side panel 202b was unfolded) and through the top (where the top panel 201b was removed). In one embodiment, the side panel 202b and the top panel 201b may be unfolded in a general direction that is opposite to or away from the insertion site (e.g., in a manner that would not interfere with the catheterization procedure).

Moreover, on the interior surface of the panel 201b, the catheterization tray 200b may include additional or alternative catheterization components, such as the syringe 170 and swabs 150. Such catheterization components may be attached or secured to the top panel 201b and/or to the side panel 202b. For example, the syringe 170 may be secured to the top panel 201b with one or more straps 220b. Furthermore, in some instances, the swabs 150 may be secured to the top panel 201b within one or more pockets 230b. It should be appreciated that, the catheterization components (such as the syringe 170, swabs 150, etc.) may be attached or secured to the top panel 201b in any number of suitable ways and with any number of suitable mechanisms (e.g., adhesive, tabs, etc.). In any event, the catheterization components secured on the interior of the top panel 201b and/or side panel 202b may be accessible and removable therefrom after unfolding thereof away from the side panels 203b, 204b, 205b.

Moreover, the side panel 202b and/or the top panel 201b may include one or more procedural indicators 260b near one or more corresponding catheterization components. For example, procedural indicators 260b may identify the catheterization components with a number that may correspond with a suggested number of a step in a suggested sequence of steps for the catheterization procedure. Also, the catheterization components and corresponding procedural indicators 260b may be arranged in a sequential manner, such that the indicators with higher numbers and corresponding catheterization components are generally positioned increasingly farther from the insertion site. In other words, the catheterization components that are used earlier in the catheterization procedure may be closer to the insertion site, while the catheterization components that are used later in the catheterization procedure are located farther away from the insertion site (based on the orientation of the catheterization tray 200b).

In one embodiment, the catheterization tray 200b may include a horizontal panel 207b, which may be connected to and extend from the side panel 204b (e.g., the horizontal panel 207b may be folded into the compartment 210b and/or may be approximately parallel to the support surface supporting the catheterization tray 200b). In some instances, the horizontal panel 207b may support and/or secure one or more catheterization components. For example, the horizontal panel 207b may secure a pouch 180b with lubricant that may be removed therefrom and used in the catheterization procedure.

Figure 37C:
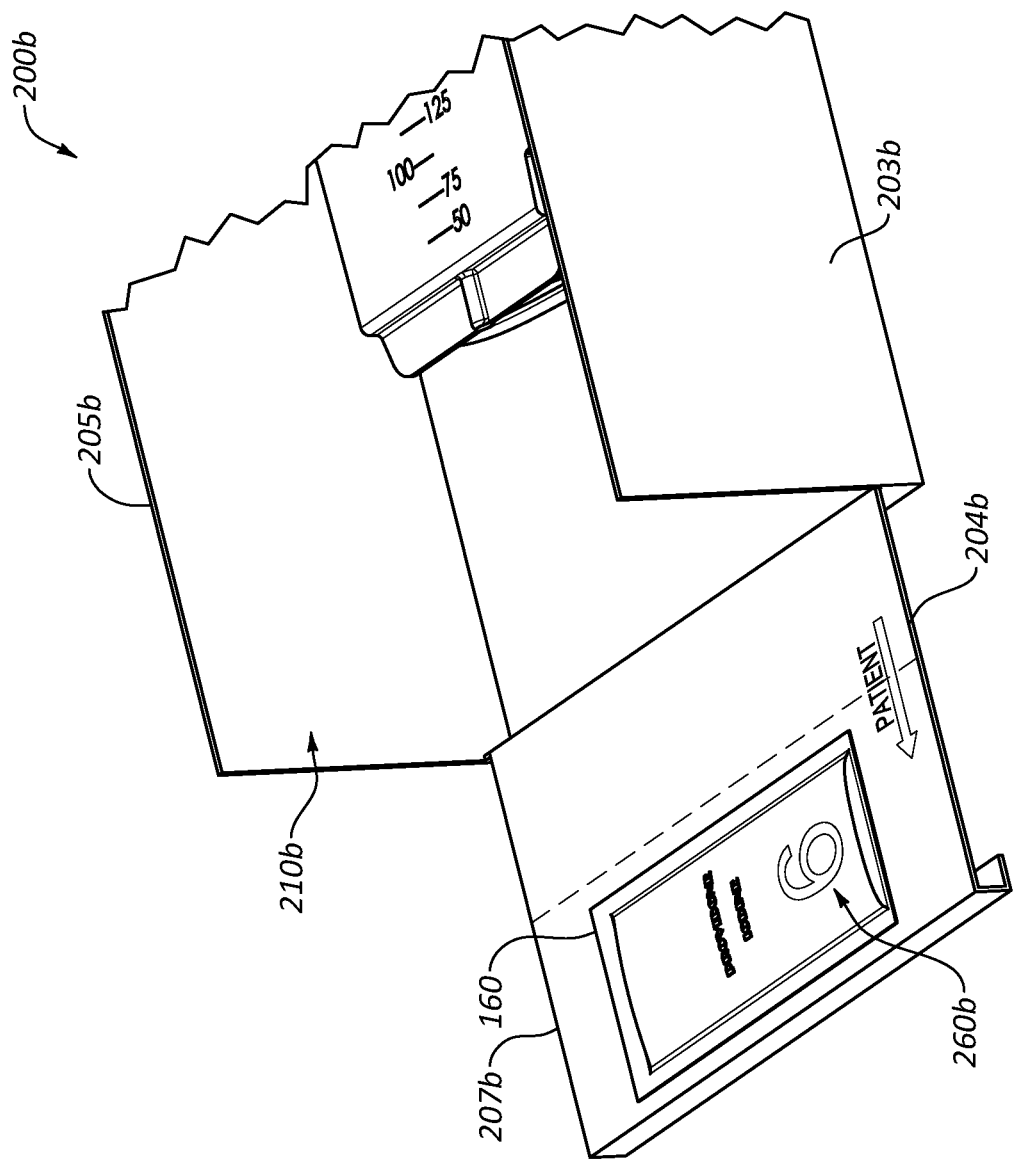
FIG. 37C is a partial isometric view of the unfolded catheterization tray of the catheterization system of FIG. 37A.

In one embodiment, the side panel 204b and horizontal panel 207b may be unfolded away from the side panels 203b and 205b, as shown in FIG. 37C. For instance, unfolding the side panel 204b may provide access into the compartment 210b. Furthermore, one or more catheterization components may be attached to the side panel 204b and/or to the interior side of the horizontal panel 207b, on the interior surface thereof. For example the sanitizer packet 160 may be attached to the horizontal panel 207b and/or to the side panel 204b (e.g., with light adhesive). Also, the catheterization tray 200b may include indicator 260b identifying the step or particular order or place in the sequence of the catheterization procedure where the sanitizer packet 160 may be used.

As described above, the catheterization system may include a catheterization tray wrapped into a sterile wrap, which may be used during the catheterization procedure. The catheterization system may include one or more catheterization components packaged by and/or secured in a sterile wrap (e.g., directly in the sterile wrap without the catheterization tray). Such catheterization system may reduce waste or materials that are thrown away after the catheterization procedure. For instance, after completing the catheterization material, the sterile wrap may be disposed and/or composted to reduce long term waste from the catheterization system.

Figure 38A:
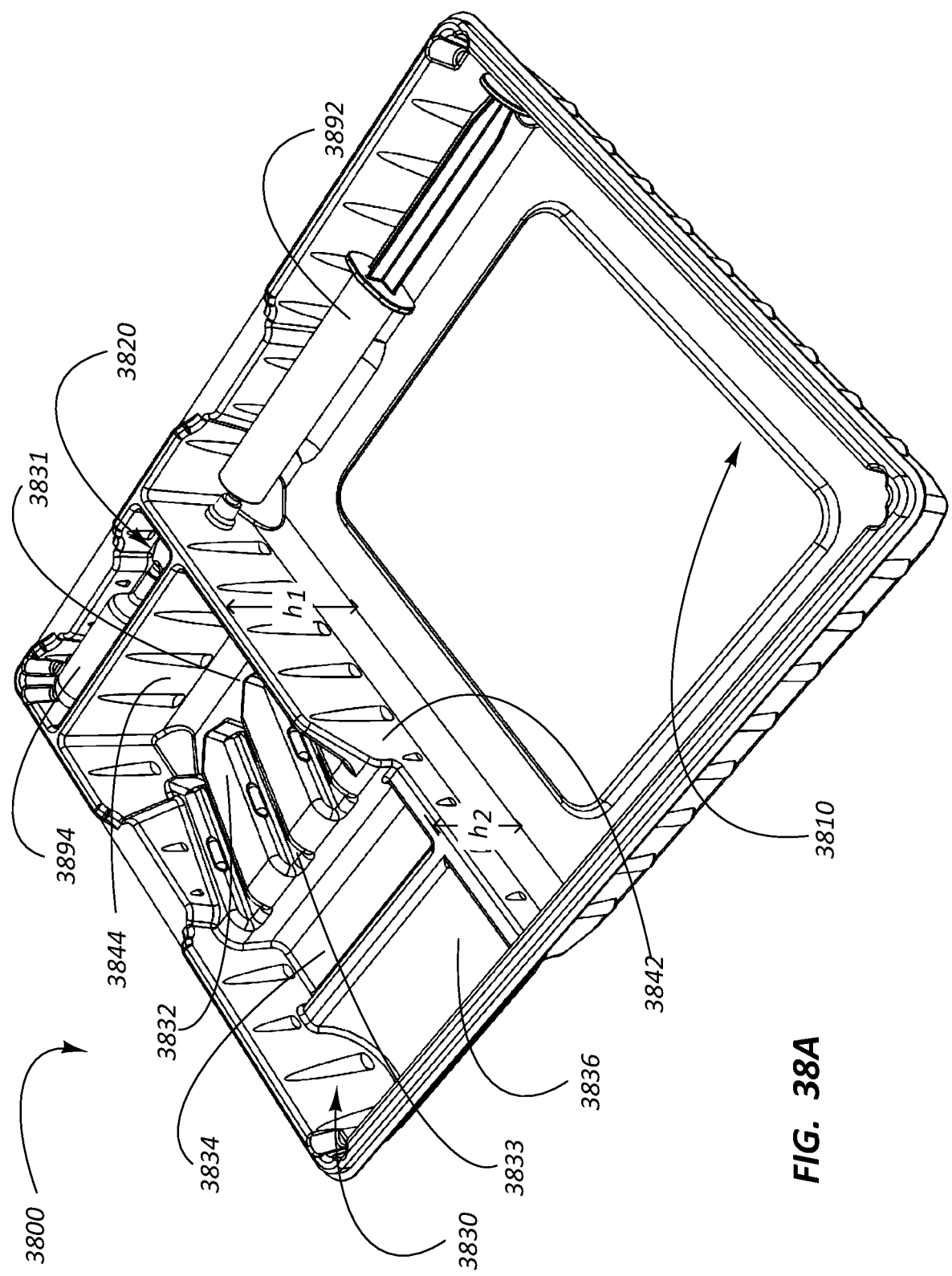
FIG. 38A shows a view of another medical-procedure tray in accordance with some embodiments.

Following on the foregoing, FIGS. 38A, 39A, 40A, 41A, 42A, and 43A provide medical-procedure trays for medical-procedure packages (e.g., catheterization trays for catheterization packages) in accordance with some alternative embodiments to previously described medical-procedure trays. For expository expediency, features of alternative embodiments shared with medical-procedure trays previously described in detail above will not be described in similar detail below. It should be understood that description for each of the shared features is incorporated by reference, as appropriate, by the shared feature's name when describing alternative embodiments. For additional expository expediency, not every feature of alternative embodiments shared with previously described medical-procedure trays will be further described. Instead, it should be understood that shared visual elements between the alternative embodiments and the previously described medical-procedure trays represent shared features between the alternative embodiments and the previously described medical-procedure trays. Thus, the shared visual elements provide a basis for incorporating by reference, as appropriate, description for each of the shared features for the alternative embodiments. For example, FIGS. 2 and 38A provide medical-procedure trays including stiffening ribs. (See stiffening ribs 20 of FIG. 2 and the description therefor.) While the stiffening ribs of the alternative embodiment of FIG. 38A are not expressly described, the description for the stiffening ribs is incorporated by reference in view of the shared visual elements representing the stiffening ribs.

Figure 38B:
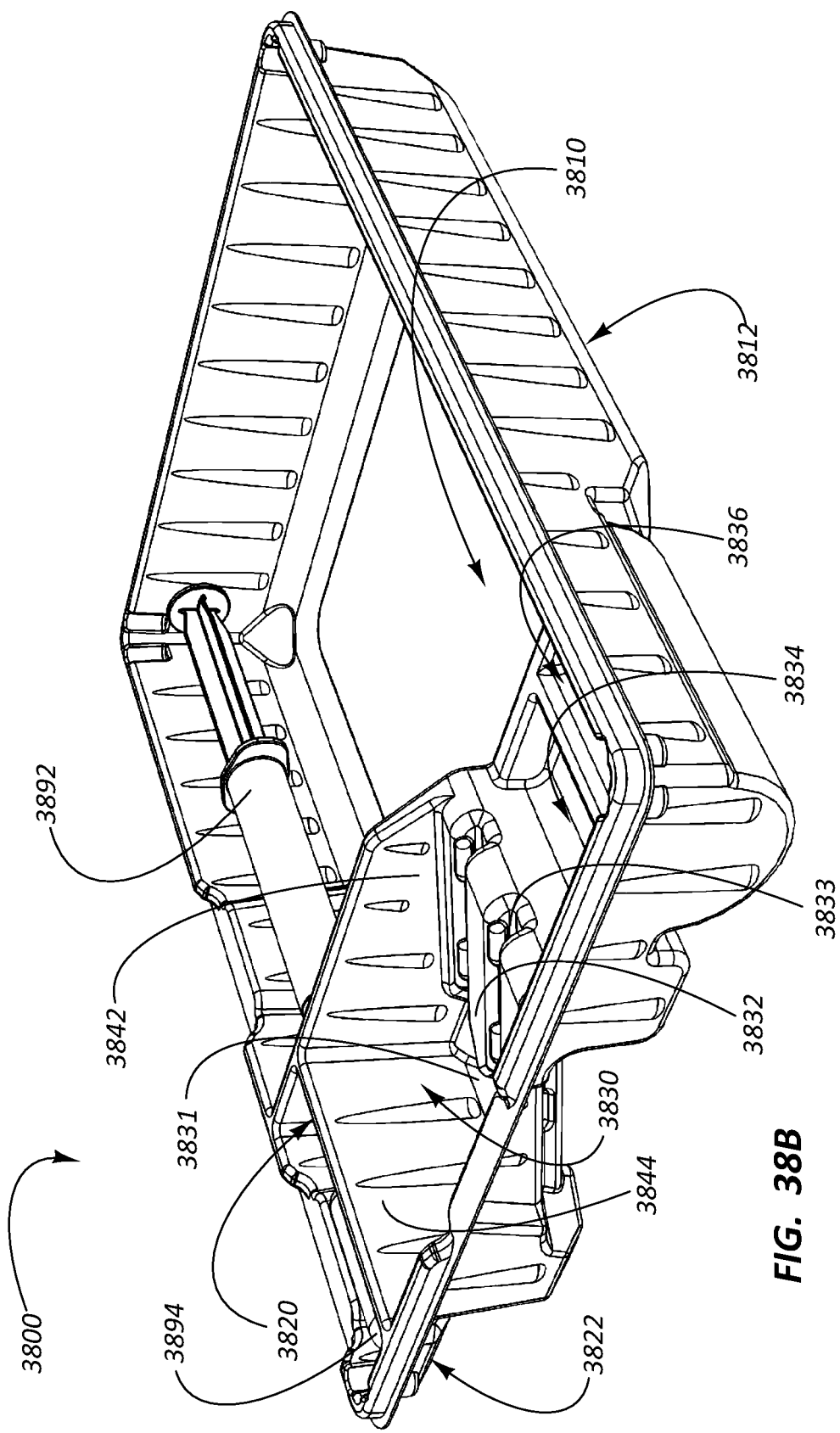
FIG. 38B shows another view of the medical-procedure tray of FIG. 38A.
Figure 38C:
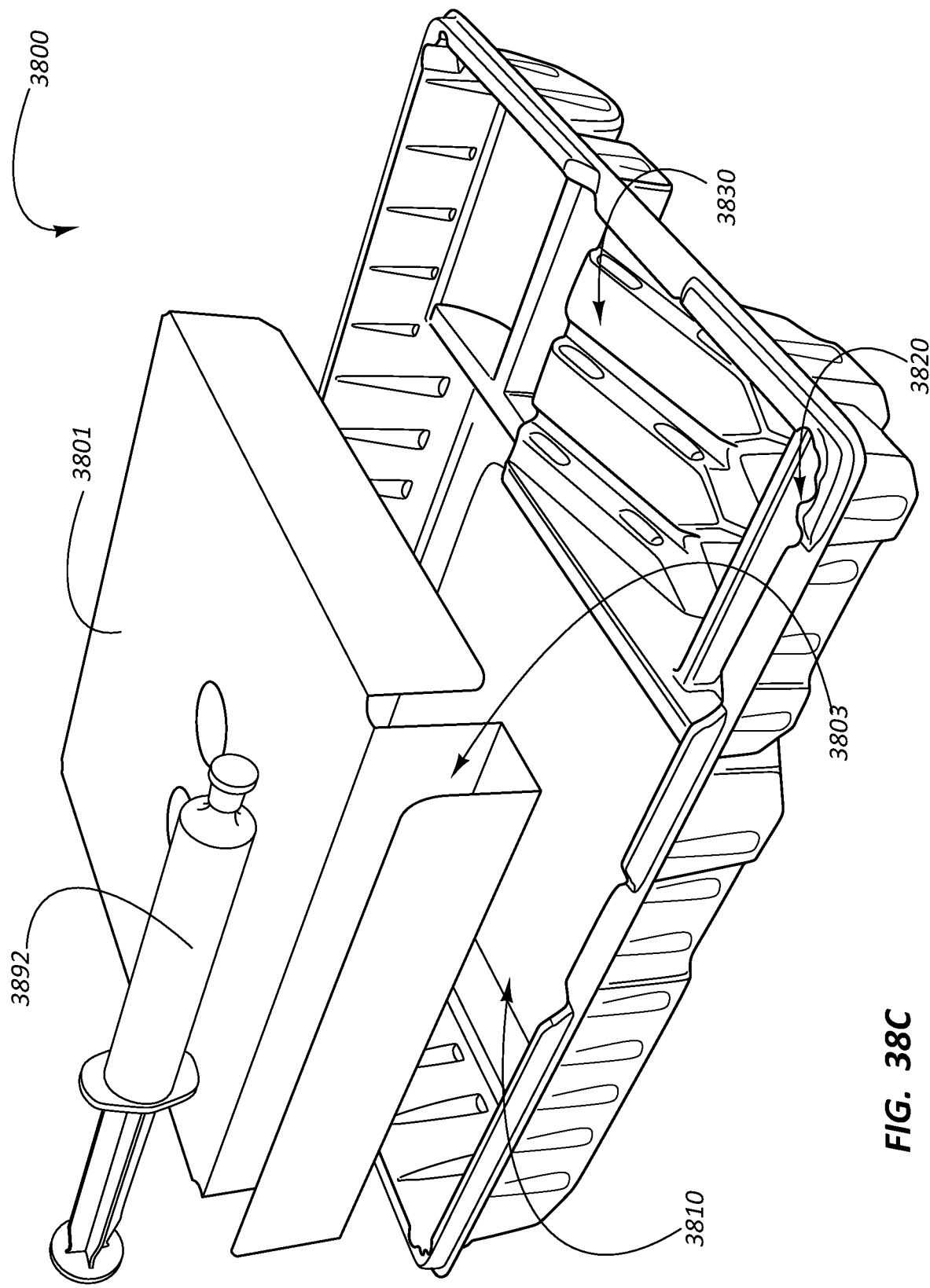
FIG. 38C shows another view of the medical-procedure tray of FIG. 38A together with a cover.
Figure 38D:
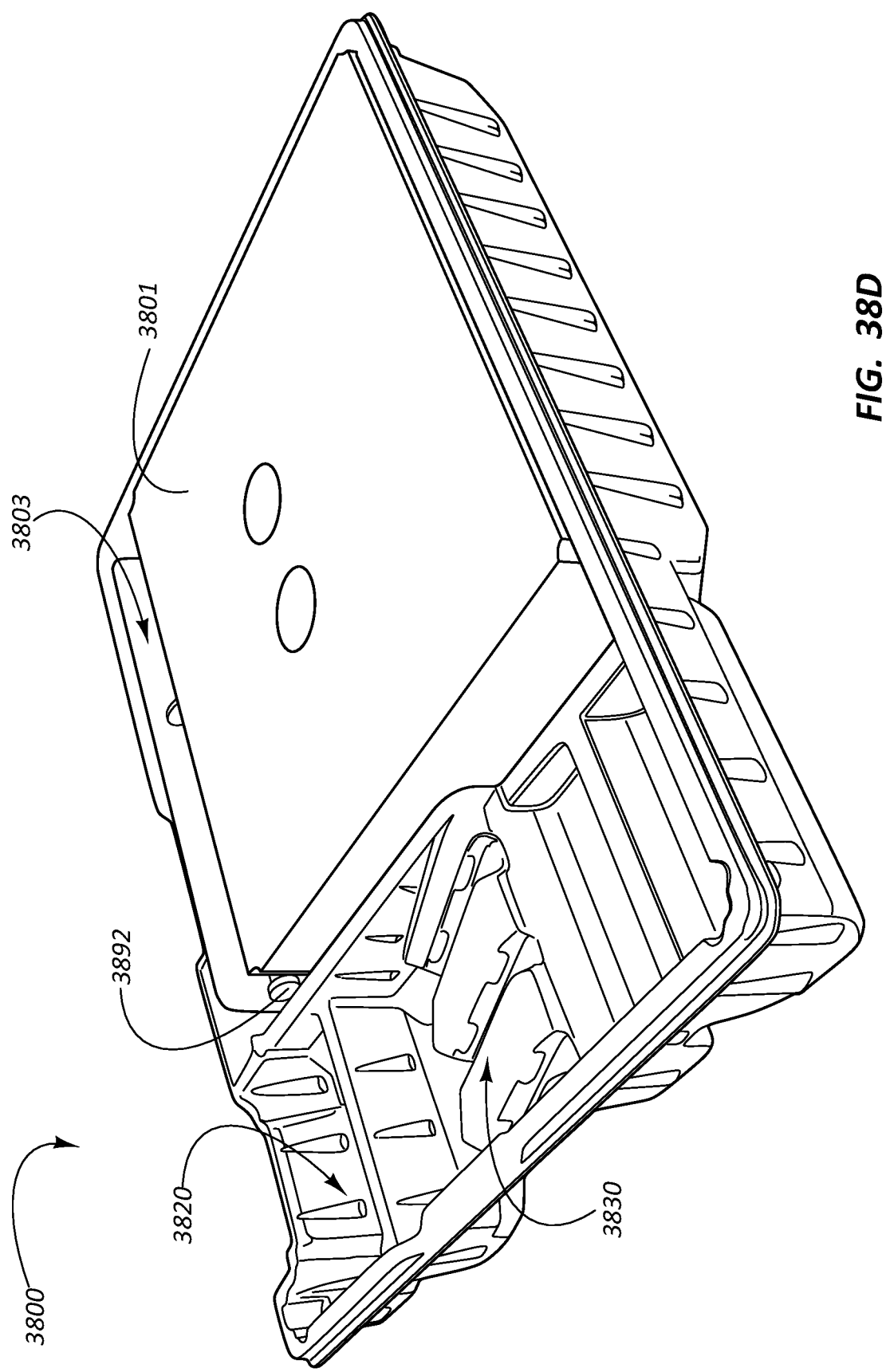
FIG. 38D shows another view of the medical-procedure tray of FIG. 38A together with a cover.

FIG. 38A shows a view of another medical-procedure tray 3800 in accordance with some embodiments. FIG. 38B shows another view of the medical-procedure tray 3800 of FIG. 38A. FIG. 38C shows another view of the medical-procedure tray 3800 of FIG. 38A together with a cover 3801. FIG. 38D shows another view of the medical-procedure tray 3801 of FIG. 38A together with the cover 3801.

The medical-procedure tray 3800 of FIGS. 38A, 38B, 38C, and 38D can include a first section 3810, a second section 3820, and a third section 3830. As described herein, a section of a medical-procedure tray can be designated for one or more particular uses (e.g., well for iodine, section for storage, etc.), and a section can be at least partially and up to wholly separated from one or more other sections by one or more physical features (e.g., one or more partitions), thereby forming a compartment for one or more particular uses. As shown, the medical-procedure tray 3800 includes a first partition 3842 formed from the medical-procedure tray 3800 itself. The first partition 3842 or at least a first section-facing face of the first partition 3842 (see FIG. 38A) has a first height $h_1$ equal to a height of the medical-procedure tray 3800 at least an end of the medical-procedure tray 3800 including the second section 3820. The first partition 3842 or at least the first section-facing face of the first partition 3842 (see FIG. 38A) has a second height $h_2$ less than the first height at least an end of the medical-procedure tray 3800 opposite the second section 3820. In view of the first partition 3842, the first section 3810 can be considered a first compartment 3810 at least partially separated from the third section 3830 and wholly separated from the second section 3820. As further shown, the medical-procedure tray 3800 includes a second partition 3844 formed from the medical-procedure tray 3800 itself. The second partition 3844 or at least a third section-facing face of the second partition 3844 (see FIG. 38A or 38B) has a first height equal to the height of the medical-procedure tray 3800. In view of the first partition 3842 and the second partition 3844, the second section 3820 can be considered a second compartment 3820 wholly separated from the first section 3810 and the third section 3830. Further in view of the first partition 3842 and the second partition 3844, the third section 3830 can be considered a third compartment 3830 at least partially separated from the first section 3810 and wholly separated from the second section 3820.

As with previously described medical-procedure trays, the medical-procedure tray 3800 can include medical-procedure instructions imprinted directly on the medical-procedure tray 3800, at least some of which instructions can be revealed in step with steps of the medical procedure. When the medical-procedure tray 3800 is incorporated into a medical-procedure package with contents for the medical procedure (e.g., a drainage system including a catheter, a container of lubricant, a syringe of water, a skin-preparation kit, etc. for a catheterization procedure), step-wise removal of the contents can reveal the step-wise instructions for the medical procedure imprinted on the medical-procedure tray 3800.

With respect to the first section or compartment 3810, the first section 3810 can be configured to accommodate a first set of contents for a medical procedure. In some embodiments, the medical procedure is a catheterization procedure and the first set of contents can include, but is not limited to, a drainage system including a catheter (e.g., a Foley catheter), drainage tubing, and a drainage bag. The first set of contents can further include a syringe of sterile water for inflating a balloon such as a balloon of a Foley catheter. When the medical-procedure tray 3800 is incorporated into a medical-procedure package, the first section 3810 can include the first set of contents. For a visual reference, the medical-procedure tray 3800 of FIGS. 38A, 38B, 38C, and 38D is shown with a syringe of sterile water 3892. As shown in FIGS. 38A and 38B, the syringe of sterile water 3892 can be simply placed alongside an inner wall of the medical-procedure tray 3800 or fit into position alongside the inner wall with a loose-fit interference fit at both end of the syringe of sterile water 3892. As shown in FIGS. 38C and 38D, the syringe of sterile water 3892 can still be placed alongside the inner wall of the medical-procedure tray 3800; however, the syringe of sterile water 3892 can be further placed within a folded portion or retainer 3803 of the cover 3801.

Referring to FIGS. 38C and 38D, the medical-procedure tray 3800 is shown together with the cover 3801 such as the packaging label 62 described in reference to FIGS. 11 and 12, the identification cover 120 described in reference to FIG. 30A, or a combination thereof. As further shown, the cover 3801 can be folded to form the retainer 3803 for retaining certain contents of the medical-procedure package in the first section 3810. For example, the retainer 3803 can be configured for keeping the syringe of sterile water 3892 in the first section 3810 apart from certain other contents of the medical-procedure package in the first section 3810. Other portions of the cover 3801 can be folded to form other retainers for retaining contents of the medical-procedure package in the appropriate sections. As shown, the cover 3801 can be configured to fit within the first section 3810 of the medical-procedure tray 3800; however, the cover 3801 can be alternatively configured to fit within the first section 3810 and additional sections (e.g., the second section 3820, the third section 3830, etc.) of the medical-procedure tray 3800 or portions thereof. The cover 3801 can be alternatively configured to fit over the medical-procedure tray 4100 in any of the foregoing configurations up to the whole medical-procedure tray 4100 excepting folded or otherwise shaped portions of the cover 3801 forming retainers for retaining contents of the medical-procedure package in the appropriate sections.

With respect to the second section or compartment 3820, the second section 3820 can be configured to accommodate a second set of contents for the medical procedure. In some embodiments, the medical procedure is a catheterization procedure and the second set of contents can include, but is not limited to, a container containing lubricant (e.g., lubricant for a Foley catheter). When the medical-procedure tray 3800 is incorporated into a medical-procedure package, the second section 3820 can include the second set of contents. For a visual reference, the medical-procedure tray 3800 of FIGS. 38A and 38B is shown with a container of lubricant 3894.

Insofar as configuration of the second section or compartment 3820 for the second set of contents, the second section 3820 can be configured as a retainer to retain or otherwise secure the second set of contents (e.g., the container of lubricant 3894) while simultaneously providing open access for easy removal of the second set of contents. The second partition 3844 formed from the medical-procedure tray 3800 can have the previously described first height (e.g., equal to the height of the medical-procedure tray 3800) at the third section-facing face of the second partition 3844 (see FIG. 38A or 38B); however, the second partition 3844 can further have a second height at a second section-facing face of the second partition 3844. The second height at the second section-facing face of the second partition 3844 can be less than the first height at the third section-facing face of the second partition 3844, which, in turn, serves to elevate a bottom 3822 of the second section 3820 above a bottom 3812 of the first section 3810 or the tray 3800 (see FIG. 38B). Again, for a visual reference, the medical-procedure tray 3800 of FIGS. 38A and 38B is shown with the container of lubricant 3894. The container of lubricant 3894 can be fit into position alongside an inner wall (or a protrusion thereof) of the medical-procedure tray 3800 shared with the second section 3820 and the second section-facing face of the second partition 3844 with a loose-fit interference fit on both sides of the container of lubricant 3894, at both ends of the container of lubricant 3894, or a combination thereof. The bottom 3822 of the second section 3820 elevated above the bottom 3812 of the first section 3810 or the tray 3800 provides for the open access for easy removal of the second set of contents.

With respect to the third section or compartment 3830, the third section 3830 can be configured to accommodate a third set of contents for the medical procedure. In some embodiments, the medical procedure is a catheterization procedure and the third set of contents can include, but is not limited to, a specimen container, optionally, a label for the specimen container, and a skin-preparation kit including a packet of antiseptic (e.g., an iodophor such as povidone-iodine, tincture of iodine, aqueous iodine, etc.) and one or more swabs. When the medical-procedure tray 3800 is incorporated into a medical-procedure package, the third section 3830 can include the third set of contents. The medical-procedure tray 3800 of FIGS. 38A and 38B is shown without the specimen container or the skin preparation kit; however, FIGS. 8, 26, and 27 provide visual references for inclusion of the one or more swabs 34 in the medical-procedure tray 3800, FIGS. 25-29 provide visual references for inclusion of the specimen container 54 in the medical-procedure tray 3800, and FIG. 25 provides a visual reference for inclusion of the packet of antiseptic 52 in the medical-procedure tray 3800.

Insofar as configuration of the third section or compartment 3830 for the third set of contents, the third section 3830 can be configured with one or more additional sub-sections or sub-compartments. As shown in FIGS. 38A and 38B, the one or more additional sub-sections or sub-compartments can include a swab compartment 3832, an overflow compartment 3834, and a corner storage compartment 3836. The swab compartment 3832, in turn, can include a well 3831 and one or more channels, one channel of which is indicated as channel 3833. The well 3831 can be positioned at a base of the second partition 3844, which separates the second section 3820 from the third section 3830 as shown in FIGS. 38A and 38B. The well 3831 can be further positioned at a base of the one or more channels, thereby adjoining each channel of the one or more channels at a well-end thereof. The well 3831 can be configured to contain a fluid such as the antiseptic of the medical-procedure package when poured therein.

The one or more channels can be configured to respectively hold the one or more swabs of the skin-preparation kit for subsequent use with the antiseptic of the packet of antiseptic. Each channel of the one or more channels can be configured to hold a respective swab of the one or more swabs optionally under at least one snap-in feature or snap-in tab positioned along a length or a longitudinal side of the channel. Any two or more snap-in tabs, such as any three or more snap-in tabs, and, for example, any four or more snap-in tabs positioned along a length or longitudinal sides of a channel can be staggered with respect to each other. As shown between FIGS. 38A and 38B, each channel of the one or more channels can include three staggered snap-in tabs along the longitudinal sides thereof (See also FIG. 8 and the description therefor.) Each channel of the one or more channels can be further configured with an incline or an angle with respect to the bottom 3812 of the tray 3800. Furthermore, each channel of the one or more channels can be configured with a delta or delta shape at the well-end thereof adjoining the well 3831. With such a configuration, a handle end of a swab held under the snap-in tabs of a channel can be elevated with respect to an absorbent-head end of the swab when the absorbent-head end is positioned in an accommodating delta therefor. As such, an absorbent head of a swab can angle downwardly into the well 3831 of the swab compartment 3832 of the third section 3830 and an elongate member of the swab can angle upwardly for gripping and removal at an appropriate step of unboxing the medical-procedure package containing the tray 3800 and the swab.

The overflow compartment 3834 can be positioned at an end of the one or more channels opposite the well 3831. The overflow compartment 3834 can be fluidly connected to the well 3831 through the one or more channels, each channel of which can be further configured to convey a fluid (e.g., the antiseptic of the skin-preparation kit) along its length when the fluid is poured therein or thereon. Should a medical procedure require additional antiseptic for skin preparation or the like, the additional antiseptic can be safely added to the well 3831 with assurance that any volume of antiseptic exceeding a total volume of the swab compartment 3832 (e.g., a combined volume of the well 3831 and the one or more channels) can spill into the overflow compartment 3834 via the one or more channels.

With respect to the corner storage compartment 3836, the corner storage can be positioned between the overflow compartment 3834 and an inner wall of the tray 3800, and, thereby share the inner wall of the tray 3800. The corner storage compartment 3836 can be configured to accommodate the specimen container of the medical-procedure package. Furthermore, while the medical-procedure package can include the packet of antiseptic in or over the swab compartment 3832 and the overflow compartment 3834 as shown in FIG. 25, the corner storage compartment 3836 can be further configured to accommodate at least a portion of the packet of antiseptic. In such a configuration, the packet of antiseptic can be placed in or over the swab compartment 3832, the overflow compartment 3834, the corner storage compartment 3836, or a combination thereof in a medical-procedure package containing the tray 3800.

Figure 39A:
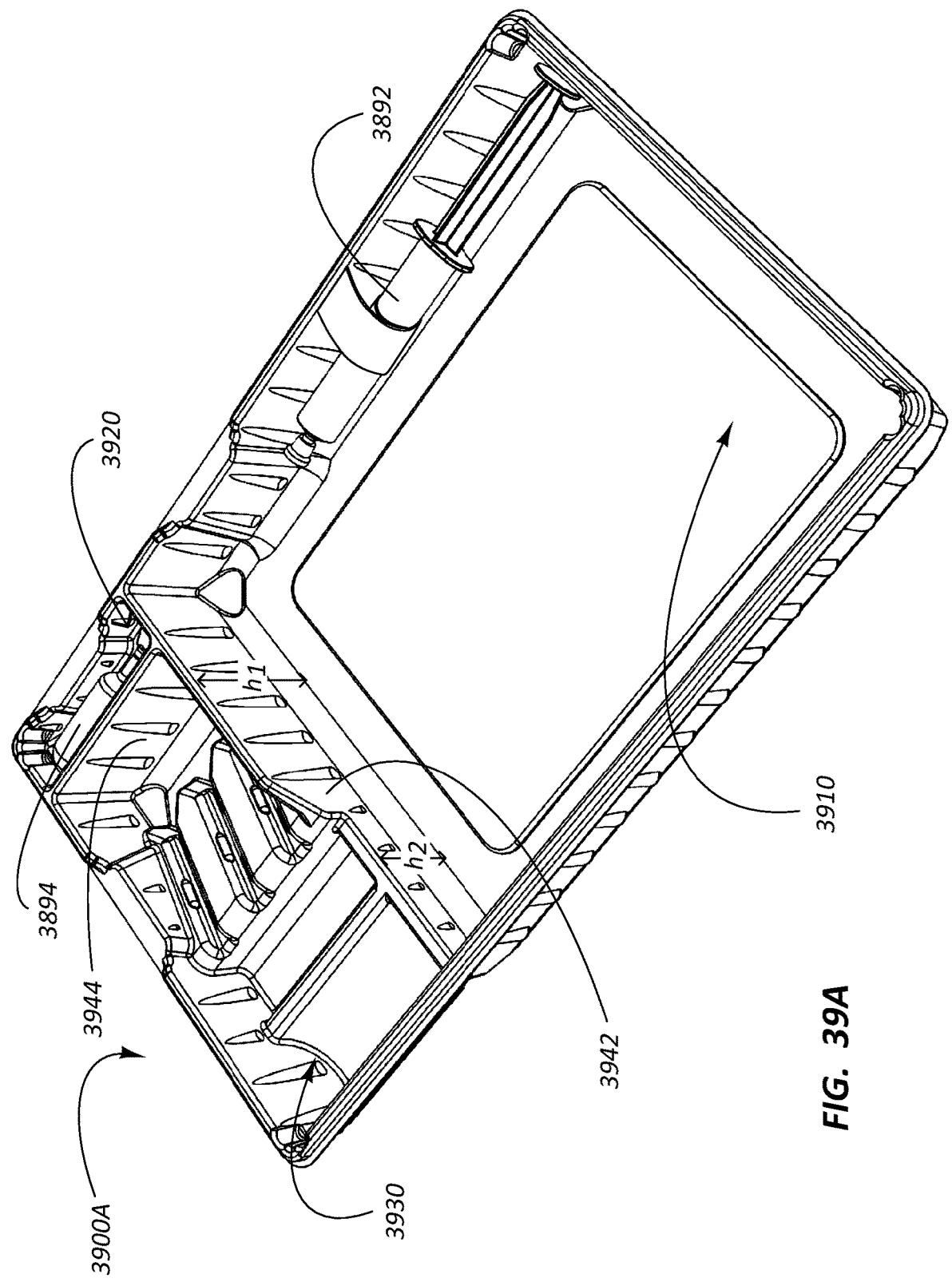
FIG. 39A shows a view of another medical-procedure tray in accordance with some embodiments.
Figure 39B:
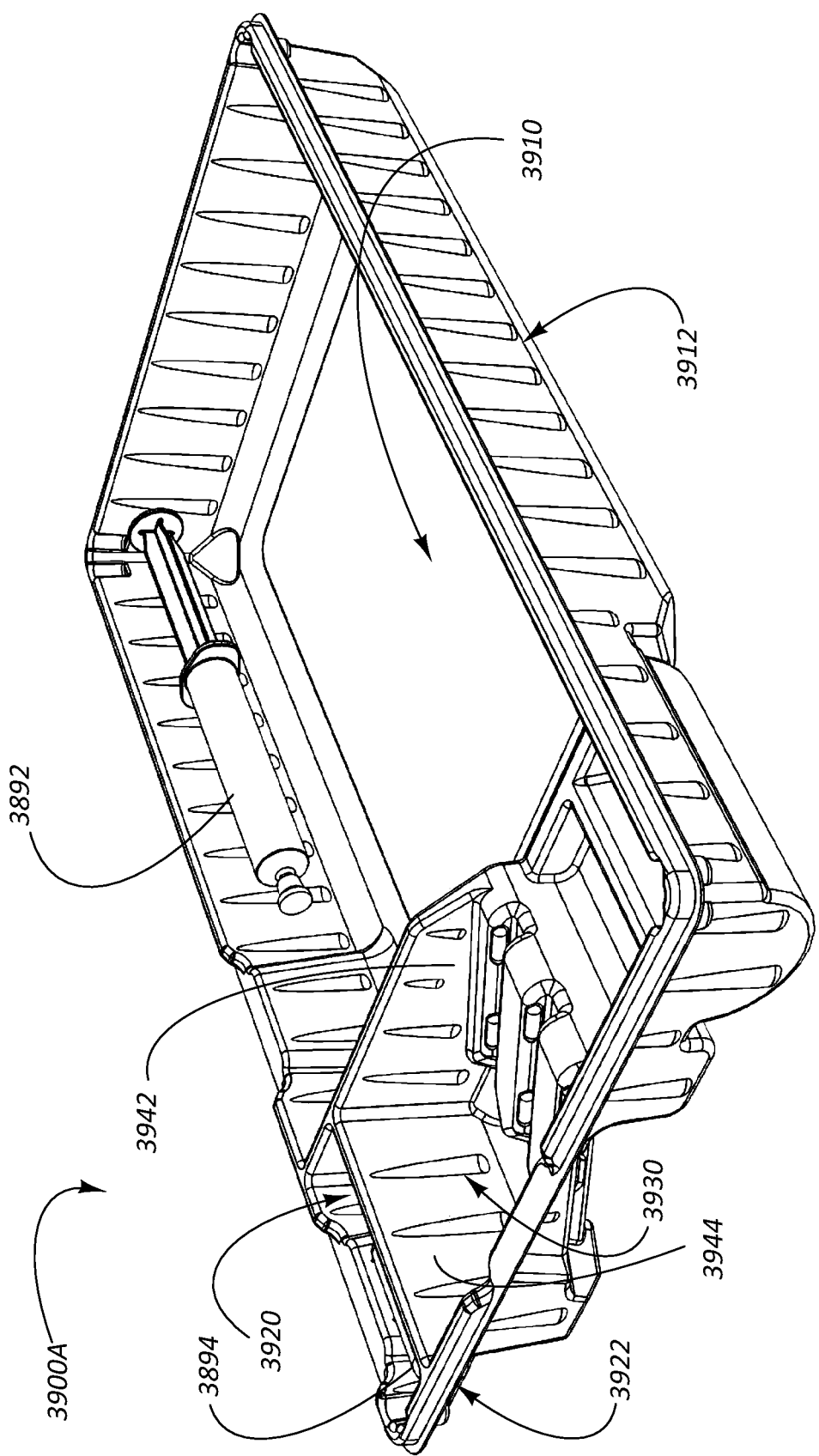
FIG. 39B shows another view of the medical-procedure tray of FIG. 39A.

FIG. 39A shows a view of another medical-procedure tray 3900 in accordance with some embodiments. FIG. 39B shows another view of the medical-procedure tray 3900 of FIG. 39A.

The medical-procedure tray 3900A of FIGS. 39A and 39B can have a configuration similar to the medical-procedure tray 3800 described in reference to FIGS. 38A, 38B, 38C, and 38D. As such, the tray 3900A can likewise include a first section or first compartment 3910, a second section or second compartment 3920, and a third section of third compartment 3930, each of which can be configured to accommodate and hold contents for a medical procedure. However, as shown, the first section 3910 of the tray 3900A can have a different configuration than the first section 3810 of the tray 3800. For example, the first section 3810 of the tray 3800 of FIGS. 38A, 38B, 38C, and 38D has more of a square-shaped footprint, whereas the first section 3910 of the tray 3900A of FIGS. 39A and 39B has more of a rectangle-shaped footprint. This results from sides of the tray 3900A about the first section 3910 (e.g., a side of the tray 3900A adjacent a syringe of sterile water 3892 and an opposite side thereof) being longer than similar sides of the tray 3800 about the first section 3810. Configuring the first section 3910 in this way allows for a comparatively larger capacity for comparatively more contents of the medical-procedure package including the tray 3900A.

Not only can the first section 3910 of the tray 3900A have a different configuration than the first section 3810 of the tray 3800, but one or more partitions of the tray 3900A can have a different configuration than the one or more partitions of the tray 3800. While not shown in FIGS. 39A and 39B, the different configuration can include a disproportionally or proportionally shorter height for the one or more partitions of the tray 3900A compared to the one or more partitions of the tray 3800, which one or more partitions can have a height (e.g., a maximum height) equal to a height of the tray. For an example of a disproportionally shorter height, a first partition 3942 of the tray 3900A can have a disproportionally shorter height than the first partition 3842 of the tray 3800, wherein an analogous first height $h_1$ of the first partition 3942 can be shorter than the first height $h_1$ of the first partition 3842, and wherein an analogous second height $h_2$ of the first partition 3942 can be substantially the same as the second height $h_2$ of the first partition 3842. FIG. 41B provides a visual reference for such a disproportionally shorter height for the first partition 3942 compared to the first partition 3842 with the understanding that the first partition 3942 of the tray 3900A continues to the inner wall of the tray 3900A as shown in FIGS. 39A and 39B. For an example of a proportionally shorter height, a second partition 3944 of the tray 3900A can have a proportionally shorter height than the second partition 3844 of the tray 3800. FIG. 41B also provides a visual reference for such a proportionally shorter height for the second partition 3944 compared to the second partition 3844. Configuring the one or more partitions of the tray 3900A to be disproportionally or proportionally shorter in height than the one or more partitions of the tray 3800 allows for a bottom of the second section 3920 to be lower than the bottom 3822 of the second section 3820 of the tray 3800 while still providing open access for easy removal of the container of lubricant 3894. For example, the bottom of the second section 3920 can be substantially co-planar with a bottom of the first section 3910 or a bottom of the tray 3900A. FIG. 41B again provides a visual reference for such a bottom of the second section 3920 of the tray 3900A with the understanding that the first partition 3942 of the tray 3900A continues to the inner wall of the tray 3900A as shown in FIGS. 39A and 39B. The embodiment of the co-planar bottom of the second section 3920 of the tray 3900A and that of the elevated bottom 3822 of the tray 3800 provide open access for easy removal of the container of lubricant 3894 in that both embodiments do not have the container of lubricant 3894 ensconced too deeply in a second-section well.

While embodiments are disclosed for an elevated second-section bottom of a tray (e.g., the elevated bottom 3822 of the second section 3820 of the tray 3800) and a second-section bottom co-planar with a bottom of the tray (e.g., the co-planar bottom of the second section 3920 of the tray 3900A), it should be understood that a bottom of any compartment of any medical-procedure tray disclosed herein can vary in elevation from a bottom of the tray in accordance with that described for the trays 3800 and 3900A.

Figure 39C:
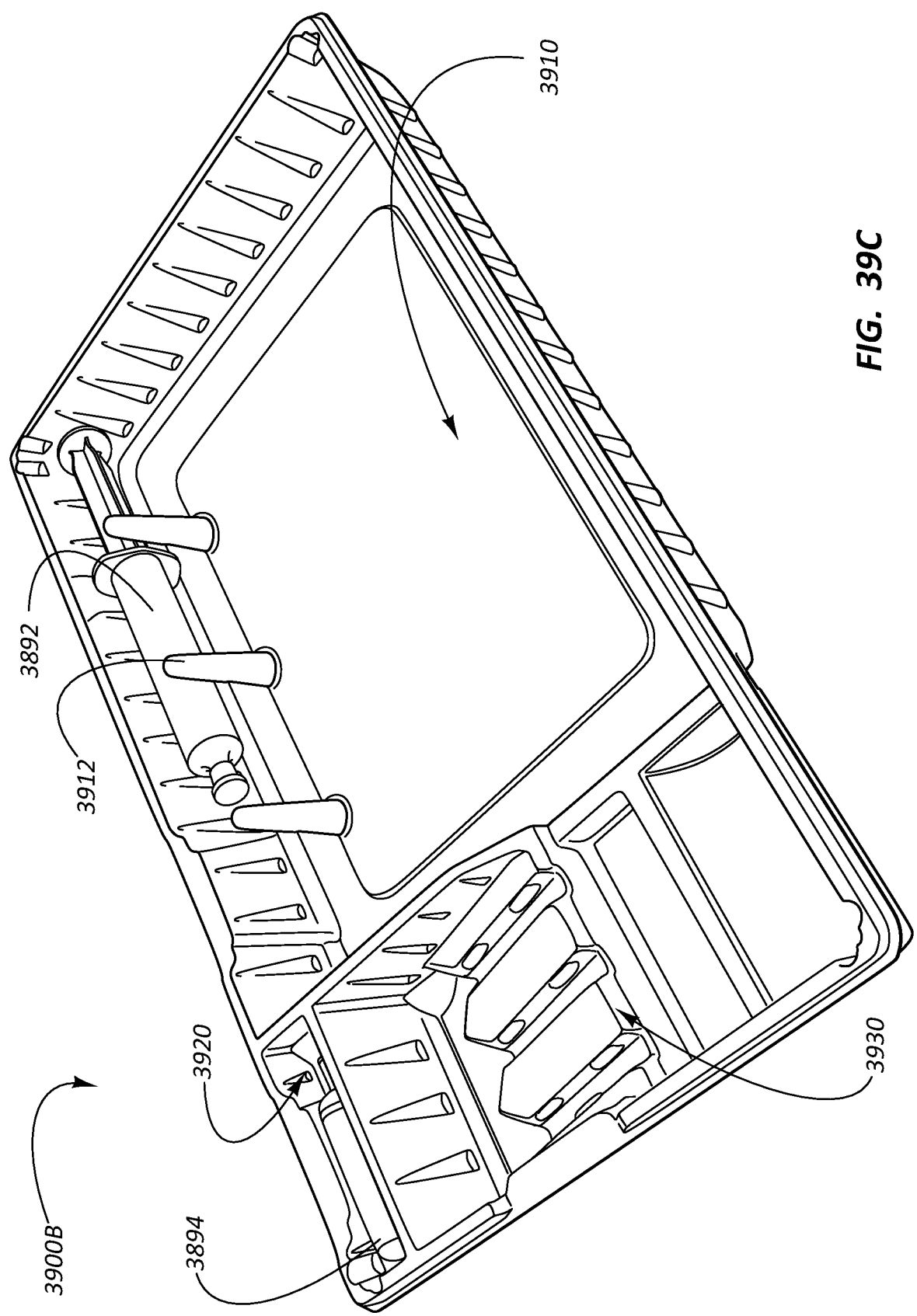
FIG. 39C shows a view of a medical-procedure tray including a number of retainers in a first configuration in accordance with some embodiments.

FIG. 39C shows a view of a medical-procedure tray 3900B including a number of retainers in a first configuration in accordance with some embodiments.

The medical-procedure tray 3900B of FIG. 39C can have a configuration similar to the medical-procedure tray 3900A described in reference to FIGS. 39A and 39B. As such, the tray 3900B can likewise include a first section 3910, a second section 3920, and a third section 3930, each of which can be configured to accommodate and hold contents for a medical procedure. However, as shown, the first section 3910 of the tray 3900B can have a different configuration than the first section 3910 of the tray 3900A. For example, the first section 3910 of the tray 3900B of FIG. 39C can have a number of retainers, one retainer of which is indicated as retainer 3912. In contrast, the first section 3910 of the tray 3900A of FIGS. 39A and 39B is shown without the number of retainers; however, it should be understood that the tray 3900A, as well as any tray provided herein, can optionally include one or more retainers of any type provided herein. The number of retainers in the first section 3910 of the tray 3900B can be configured for retaining certain contents of the medical-procedure package in the first section 3910. For example, the number of retainers can be configured for keeping the syringe of sterile water 3892 in the first section 3910 apart from certain other contents of the medical-procedure package in the first section 3910. Any of a number of different types of retainers (e.g., column or tapered column-type retainers, rack-type retainers, tab-type retainers, removable retainers, etc.) can be formed, and any of a number of retainers (e.g., 1, 2, 3, 4, or 5 or more retainers) can be formed—some of which retainers can be formed from the tray 3900B itself. As shown, in FIG. 39C, the first section 3910 of the tray 3900B can include at least 3 tapered column-type retainers equidistant from the side of the tray 3900B adjacent the syringe of sterile water 3892.

Figure 39D:
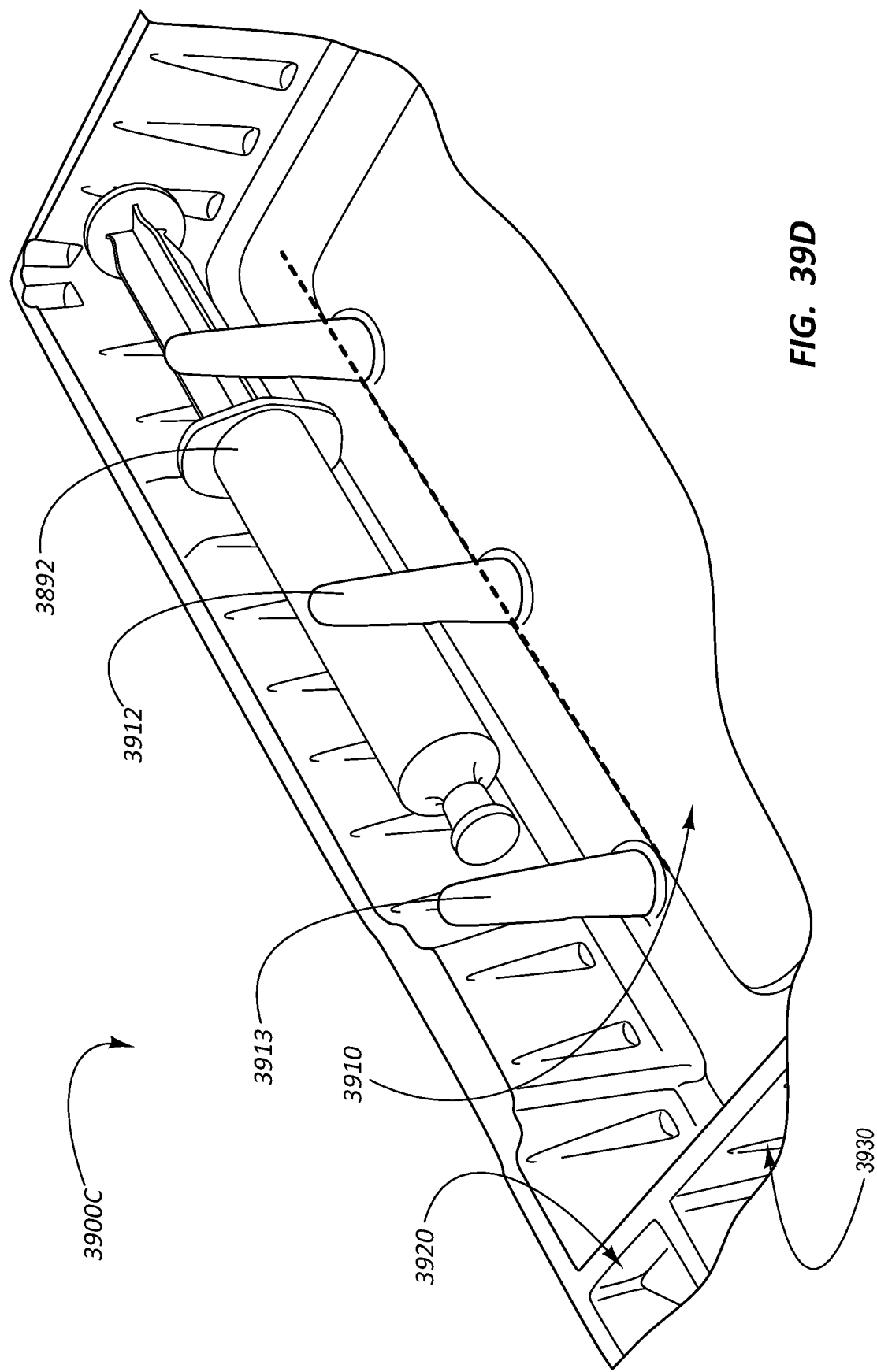
FIG. 39D shows a view of a medical-procedure tray including a number of retainers in a second configuration in accordance with some embodiments.

FIG. 39D shows a view of a medical-procedure tray 3900C including a number of retainers in a second configuration in accordance with some embodiments.

The medical-procedure tray 3900C of FIG. 39D can have a configuration similar to the medical-procedure tray 3900B described in reference to FIG. 39C. As such, the tray 3900C can likewise include a first section 3910, a second section 3920, and a third section 3930, each of which can be configured to accommodate and hold contents for a medical procedure. However, as shown, the first section 3910 of the tray 3900C can have a different configuration than the first section 3910 of the tray 3900B. For example, the first section 3910 of the tray 3900C of FIG. 39D can similarly have at least 3 tapered column-type retainers, one retainer of which is indicated as retainer 3912, and another retainer of which is indicated as retainer 3913. However, in contrast to the at least 3 tapered column-type retainers equidistantly spaced from the side of the tray 3900B, at least one retainer (e.g., the retainer 3913) of the at least 3 tapered column-type retainers of the tray 3900C can be offset from the others as shown by the dotted line. Such a different configuration can further restrict degrees of freedom of certain contents (e.g., the syringe of sterile water 3892) of the medical-procedure package in the first section 3910. As such, such a different configuration can further keep such certain contents in the first section 3910 apart from certain other contents of the medical-procedure package in the first section 3910.

Figure 40A:
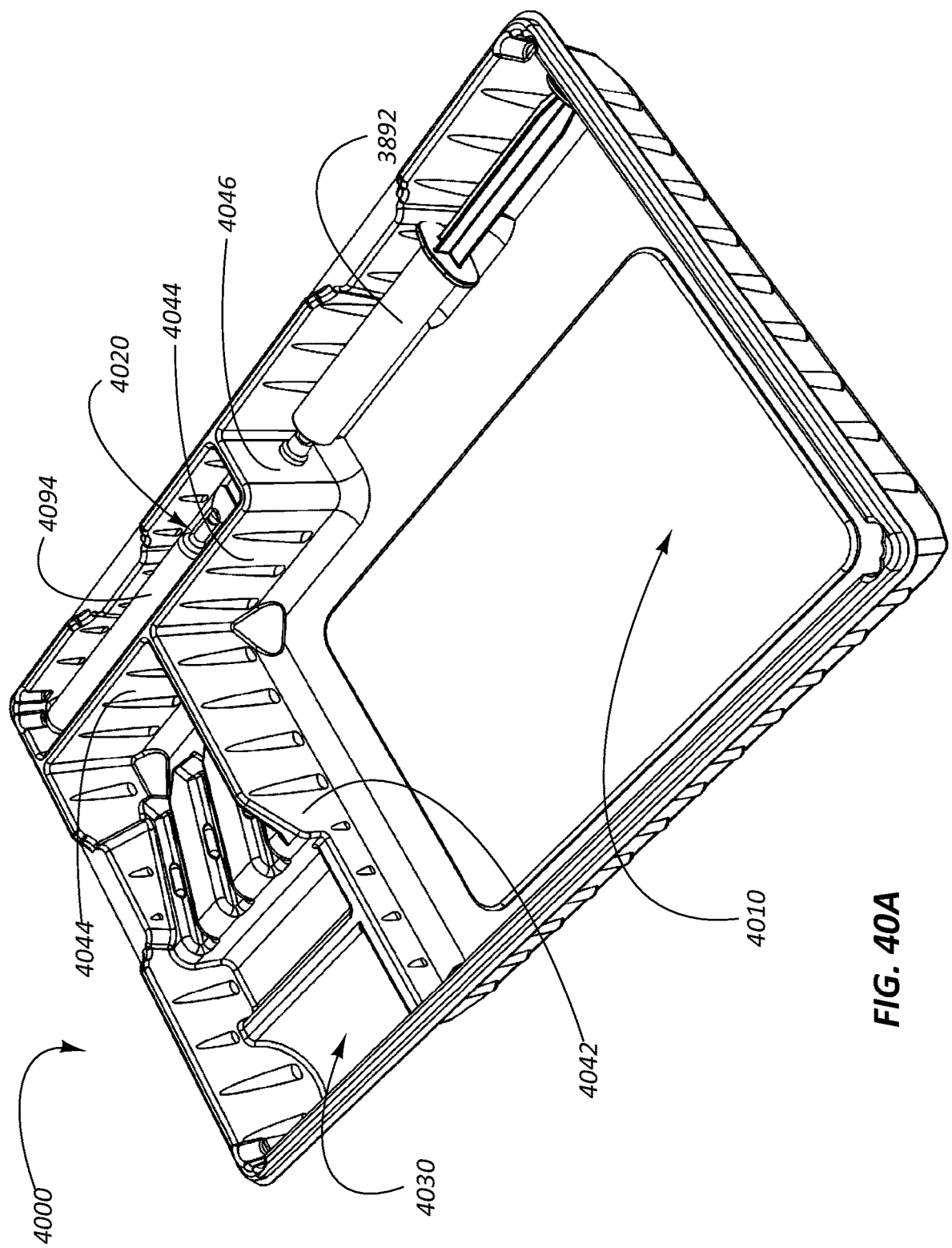
FIG. 40A shows a view of another medical-procedure tray in accordance with some embodiments.
Figure 40B:
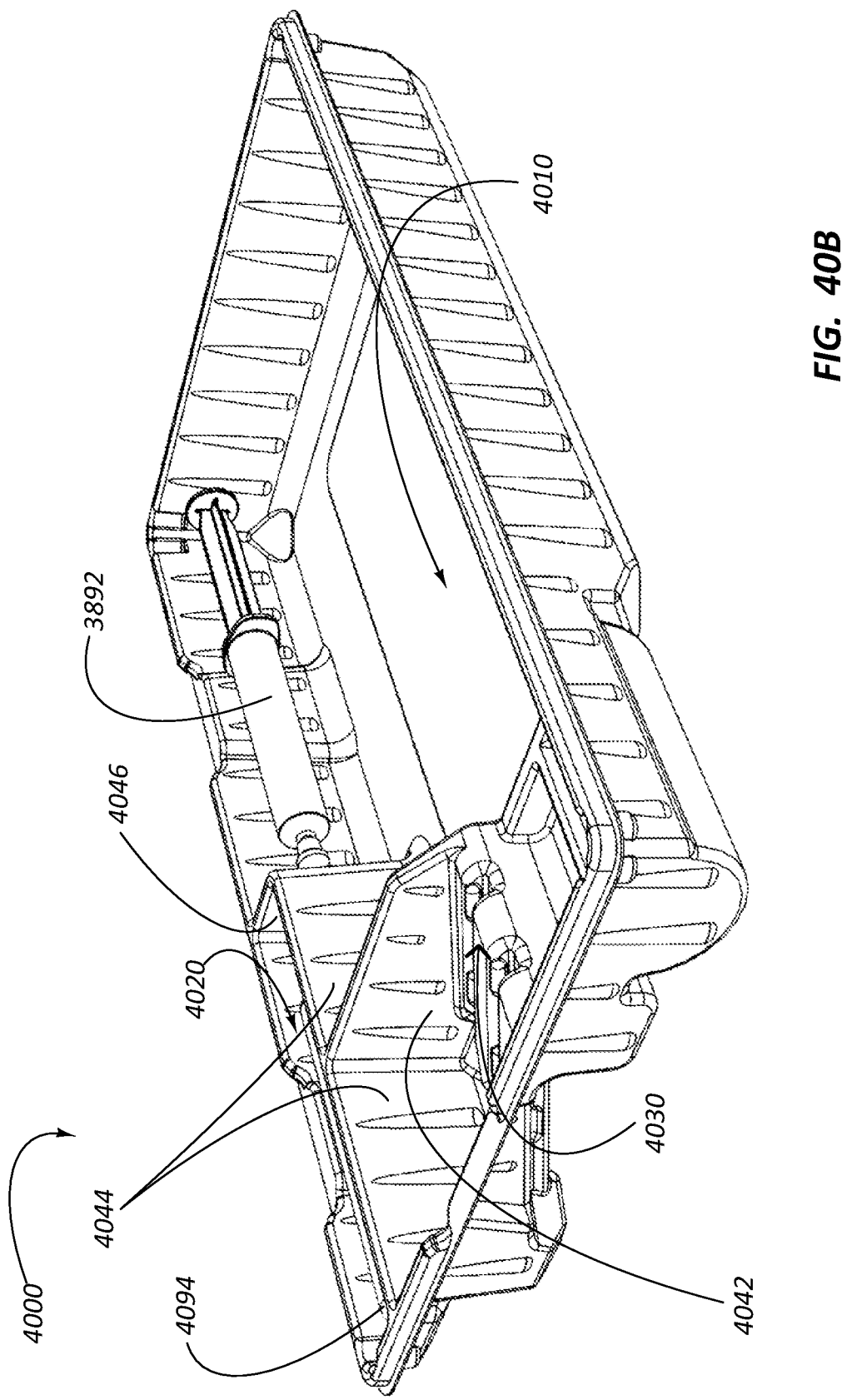
FIG. 40B shows another view of the medical-procedure tray of FIG. 40A.

FIG. 40A shows a view of another medical-procedure tray 4000 in accordance with some embodiments. FIG. 40B shows another view of the medical-procedure tray 4000 of FIG. 40A.

The medical-procedure tray 4000 of FIGS. 40A and 40B can have a configuration similar to the medical-procedure tray 3900A described in reference to FIGS. 39A and 39B. As such, the tray 4000 can likewise include a first section or first compartment 4010, a second section or second compartment 4020, and a third section or third compartment 4030, each of which can be configured to accommodate and hold contents for a medical procedure. However, as shown, the second section 4020 of the tray 4000 can have a different configuration than the second section 3920 of the tray 3900A. For example, the second section 4020 of the tray 4000 can be an extended section extending into the first section 4010, whereas the second section 3920 of the tray 3900A terminates at a common partition to both the second section 3920 and the third section 3930 of the tray 3900A, namely at the first partition 3942. The extended second section 4020 of the tray 4000 can be formed from an extended second partition 4044 extending into the first section 4010 and terminating at a third partition 4046 in the first section 4010 of the tray 4000. In addition, a first partition 4042 separating the third section 4030 from the first section 4010 can terminate at a medial portion of the extended second partition 4044 instead of at an inner wall of the tray 4000. With the second section 4020 configured as an extended section, the extended second section 4020 can accommodate more contents, larger contents, or both as needed for a medical procedure. As shown, the extended second section 4020 includes a larger container of lubricant 4094 compared to the container of lubricant 3894 shown in FIGS. 39A and 39B.

Figure 41A:
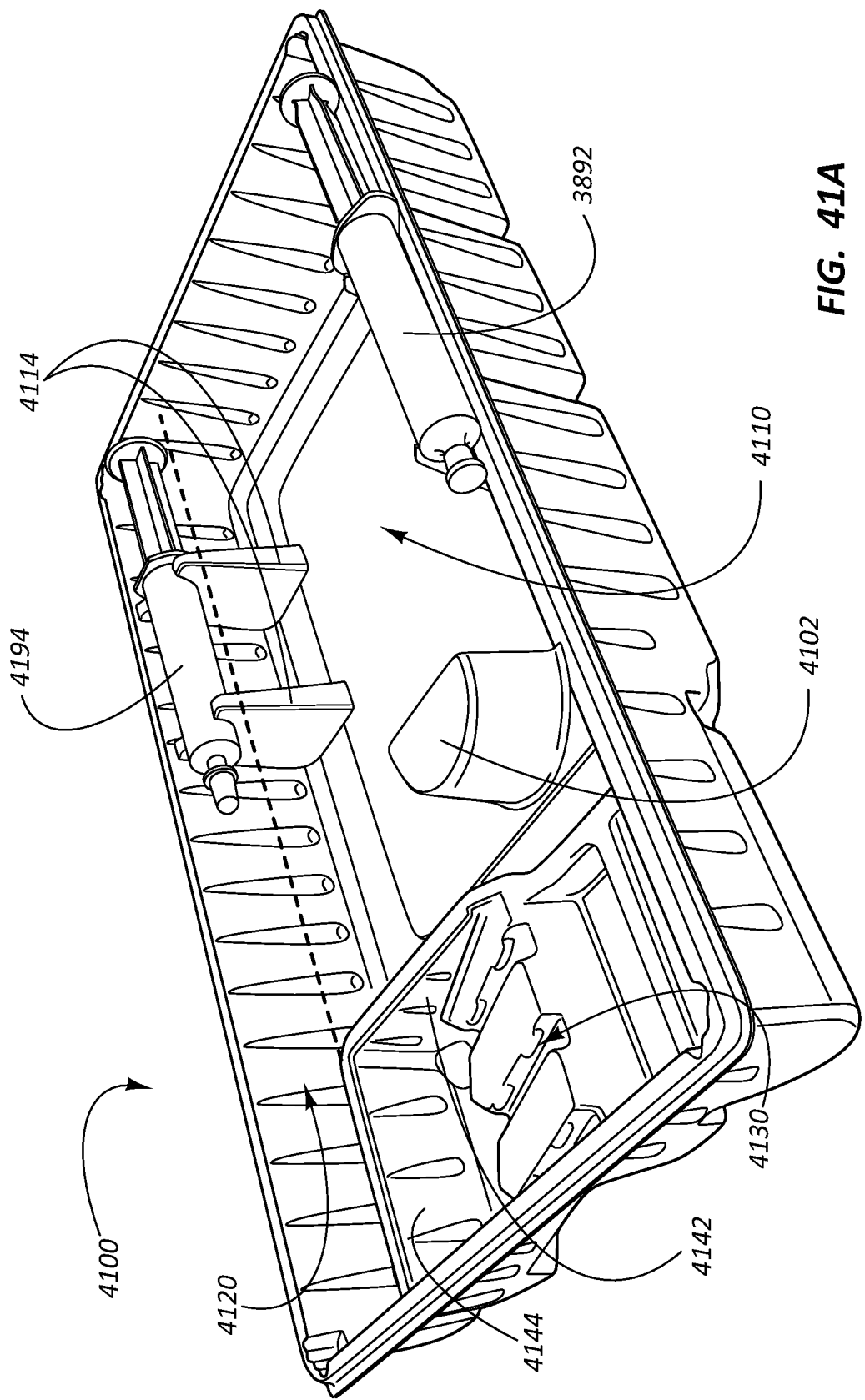
FIG. 41A shows a view of another medical-procedure tray in accordance with some embodiments.
Figure 41B:
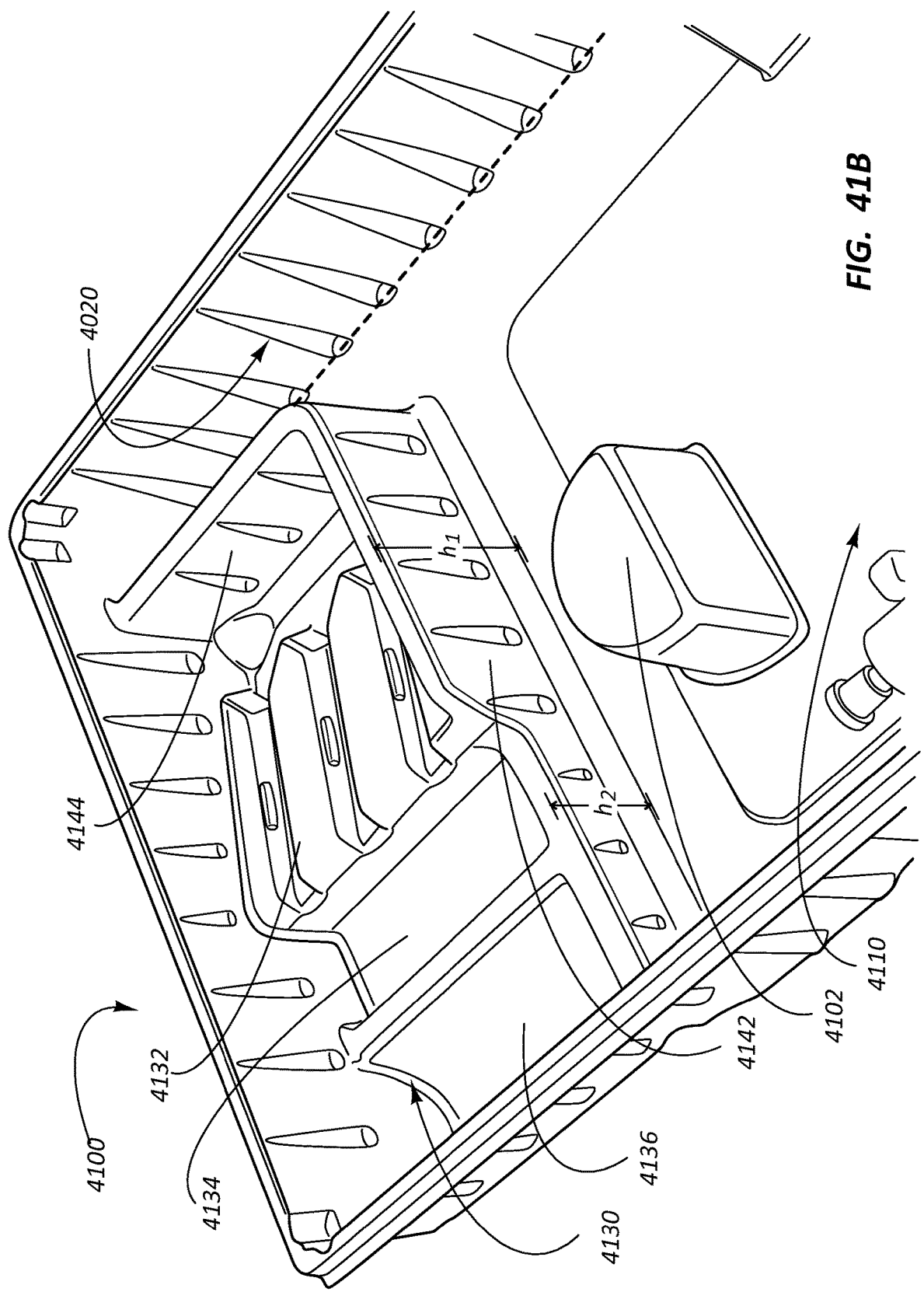
FIG. 41B shows another view of the medical-procedure tray of FIG. 41A.
Figure 41C:
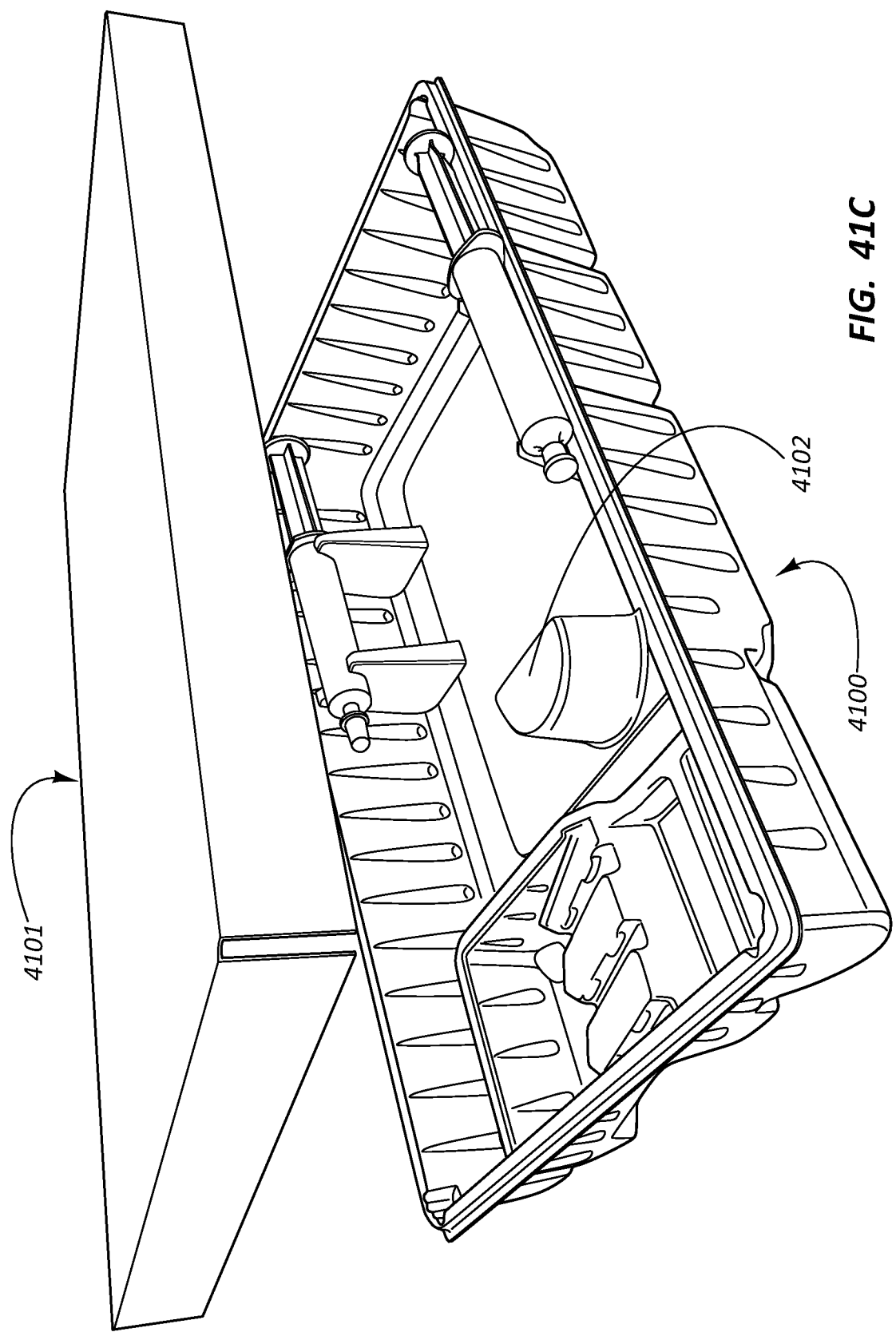
FIG. 41C shows another view of the medical-procedure tray of FIG. 41A.

FIG. 41A shows a view of another medical-procedure tray 4100 in accordance with some embodiments. FIG. 41B shows another view of the medical-procedure tray 4100 of FIG. 41A. FIG. 41C shows a third view of the medical-procedure tray 4100 of FIG. 41A.

The medical-procedure tray 4100 of FIGS. 41A, 41B, and 41C can include a first section 4110, a second section 4120, and a third section 4130, each of which can be configured to accommodate and hold contents for a medical procedure. As described herein, a section of a medical-procedure tray can be designated for one or more particular uses, and a section can be at least partially (e.g., the second section 4120) and up to wholly (e.g., the third section 4130) separated from one or more other sections by one or more physical features (e.g., one or more partitions), thereby forming a compartment for one or more particular uses. As shown, the tray 4100 includes a first partition 4142 and a second partition 4144 wholly separating the third section 4130 from the first section 4110 and the second section 4120. In addition, the second partition 4144 partially separates the second section 4120 from the first section 4110. Like the medical-procedure tray 3800 of FIGS. 38A and 38B, the first partition 4142 of the tray 4100—or at least a first section-facing face of the first partition 4142—can have a first height $h_1$ and a second height $h_2$ (see FIG. 41B), and the second partition 4144—or at least the third section-facing face of the second partition 4144—can have a first height (not shown). Unlike the tray 3800 of FIGS. 38A and 38B, the first height of the first partition 4142 and the first height of the second partition 4144 are, as shown, less than a height of the medical-procedure tray 4100. In addition, a second section-facing face of the second partition 4144 can have a height equal to the height of the third section-facing face of the second partition 4144 making a bottom of the second section 4120 co-planar with a bottom of the first section 4110 or the tray 4100. (See FIG. 41B.)

With respect to the first section 4110 of the tray 4100, the first section 4110 can be configured to accommodate a first set of contents for a medical procedure such as a catheterization procedure. As previously described, the first set of contents can include, but is not limited to, the drainage system including the catheter (e.g., the Foley catheter), the drainage tubing, the drainage bag, and the syringe of sterile water 3892 for inflating the balloon of the Foley catheter. For a visual reference, the syringe of sterile water 3892 is shown mounted in or on a retainer (e.g., a rack-type retainer) of the first section 4110 of a different type than the retainers (e.g., tapered column-type retainers) described in reference to trays 3900B and 3900C respectively of FIGS. 39C and 39D. Like the number of retainers of trays 3900B and 3900C, the retainer for the syringe of sterile water 3892 can be formed of the tray 4100 itself and configured to keep the syringe of sterile water 3892 in the first section 4110 apart from other contents of the medical-procedure package in the first section 4110. The syringe of sterile water 3892 can simply lay in the retainer or rack, or the syringe of sterile water 3892 can be fit into the retainer or rack with a loose-fit interference fit about the syringe of sterile water 3892.

With respect to the second section 4120 of the tray 4100, the second section 4120 can be configured to accommodate a second set of contents for the medical procedure such as the catheterization procedure. As previously described, the second set of contents can include, but is not limited to, the container containing lubricant (e.g., lubricant for the Foley catheter) such as a syringe of lubricant 4194. For a visual reference, the syringe of lubricant 4194 is shown mounted in or on a retainer 4114 (e.g., a rack-type retainer) like that described in reference to the retainer in the first section 4110 for the syringe of sterile water 3892. The syringe of lubricant 4194 can simply lay in the retainer or rack 4194, or the syringe of lubricant 4194 can be fit into the retainer or rack 4194 with a loose-fit interference fit about the syringe of lubricant 4194.

The retainer 4194 and the retainer for the syringe of sterile water 3892 can have the same or different dimensions as required by the size of the syringe of lubricant 4194 and the size of the syringe of sterile water 3892 required by the medical procedure. When the size of the syringe of lubricant 4194 and the size of the syringe of sterile water 3892 are the same, the retainers or racks therefor can have the same dimensions, and the syringe of lubricant 4194 and the syringe of sterile water 3892 can be swapped with respect to their placement in the medical-procedure package, for example, to better orchestrate steps of the medical procedure. Therefore, the second section 4120 is not limited to accommodating and holding the syringe of lubricant 4194, and the first section 4110 is not limited to accommodating and holding the syringe of sterile water 3892. The second section 4120 can be configured to accommodate and hold the syringe of sterile water 3892, and the first section 4110 can be configured to accommodate the syringe of lubricant 4194—even if the size of the syringe of lubricant 4194 and the size of the syringe of sterile water 3892 are different.

With respect to the third section 4130, the third section 4130 includes a swab compartment 4132, an overflow compartment 4134, and a corner storage compartment 4136 configured as described herein to accommodate a third set of contents for the medical procedure such as the catheterization procedure. As previously described, the third set of contents can include, but is not limited to, the specimen container, optionally, the label for the specimen container, and the skin-preparation kit including the packet of antiseptic (e.g., an iodophor such as povidone-iodine, tincture of iodine, aqueous iodine, etc.) and the one or more swabs. The medical-procedure tray 4100 of FIGS. 41A, 41B, and 41C is shown without the specimen container or the skin preparation kit for which the third section 4130 is configured; however, FIGS. 8, 26, and 27 provide visual references for inclusion of the one or more swabs 34 in the swab compartment 4132, FIGS. 25-29 provide visual references for inclusion of the specimen container 54 in the corner storage compartment 4136, and FIG. 25 provides a visual reference for inclusion of the packet of antiseptic 52 in the medical-procedure tray 4100 over the swab compartment 4132 and the overflow compartment 4134.

Adverting to FIG. 41C, the medical-procedure tray 4100 is shown together with a cover 4101 such as the packaging label 62 described in reference to FIGS. 11 and 12, the identification cover 120 described in reference to FIG. 30A, or a combination thereof. As shown, the cover 4101 can be configured to fit over the whole medical-procedure tray 4100; however, the cover 4101 can be alternatively configured to fit over a portion of the medical-procedure tray 4100, the portion including any one or more sections selected from the first section 4110, the second section 4120, and the third section 4130. The cover 4101 can be alternatively configured to fit within the medical-procedure tray 4100 in any of the foregoing configurations such as within the whole medical-procedure tray 4100 or a portion of the medical-procedure tray 4100. (See, for example, cover 3801 of FIGS. 38C and 38D.) As further shown, the tray 4100 can be configured with an optional support 4102 in the first section 4110 of the tray 4100. The support 4102 can prevent caving of the cover 4101 and damage to the contents of the tray 4100 thereunder when one or more medical-procedure packages are stacked on the medical-procedure package including the medical-procedure tray 4100 and the cover 4101. The support can be configured with a height substantially equal to a height of the tray 4100 and a width sufficient to withstand the weight of a stack of one or more medical-procedure packages stacked thereon.

Figure 42A:
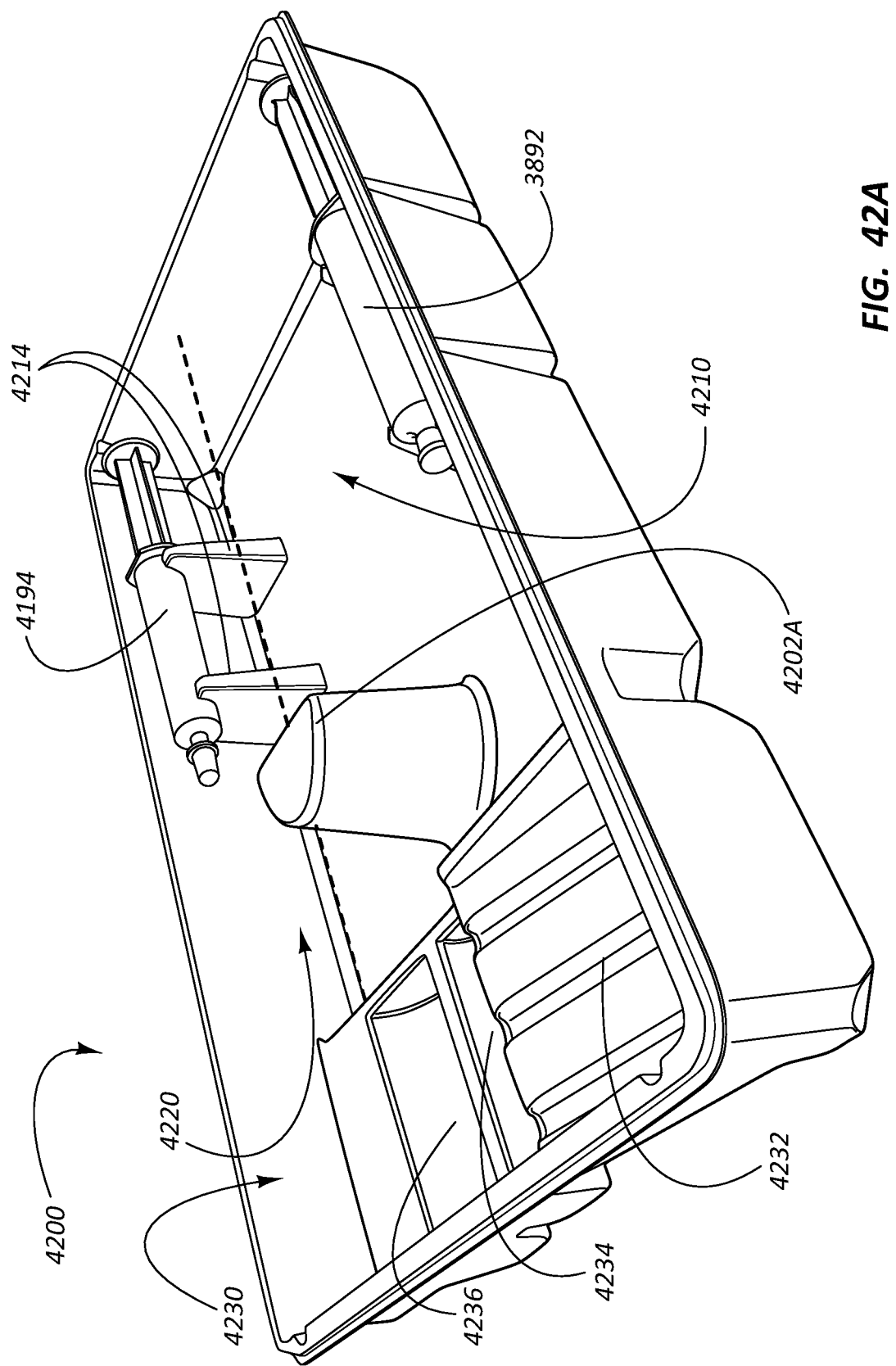
FIG. 42A shows a view of another medical-procedure tray in accordance with some embodiments.
Figure 42B:
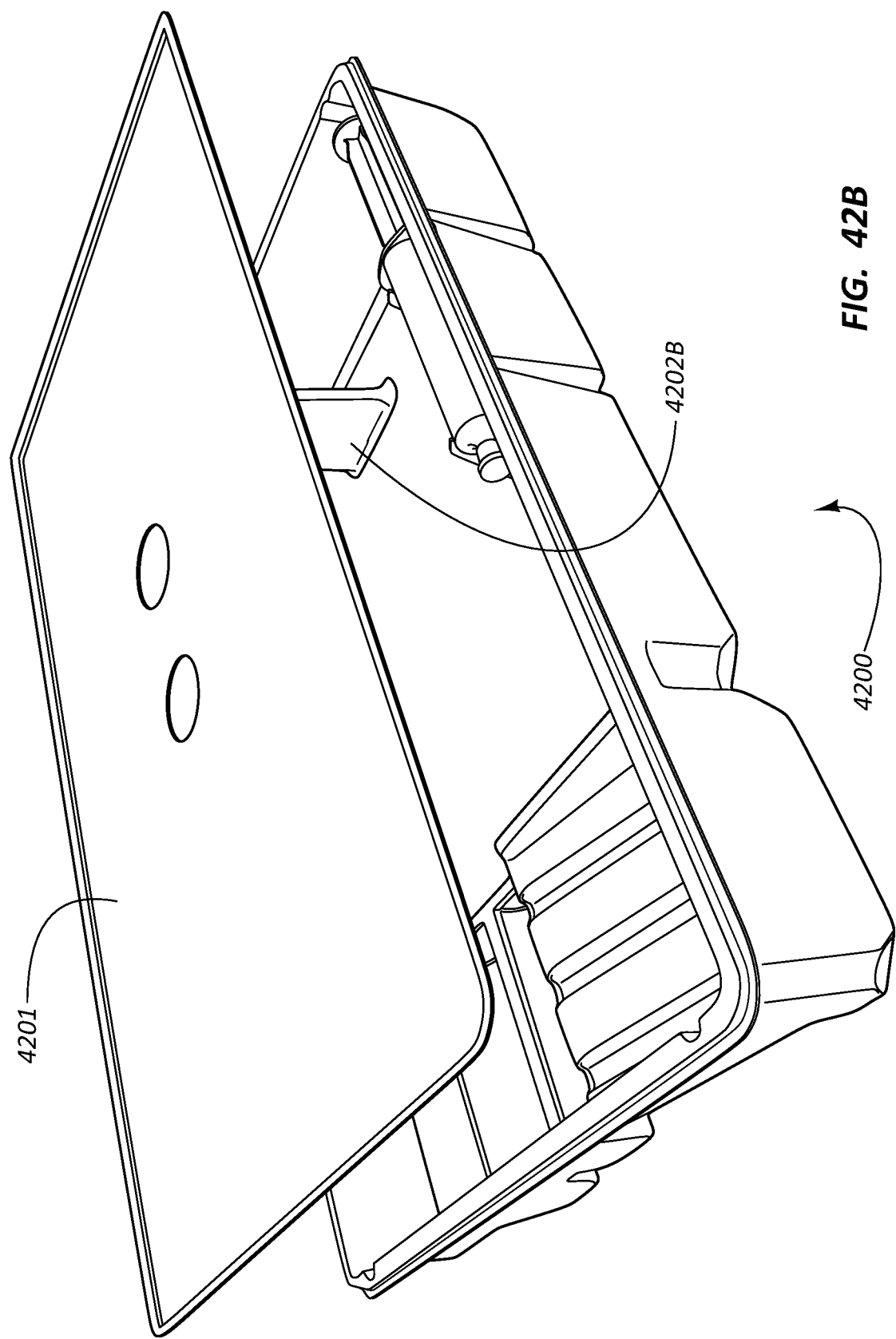
FIGS. 42B and 42C show other views of the medical-procedure tray of FIG. 42A.
Figure 42C:
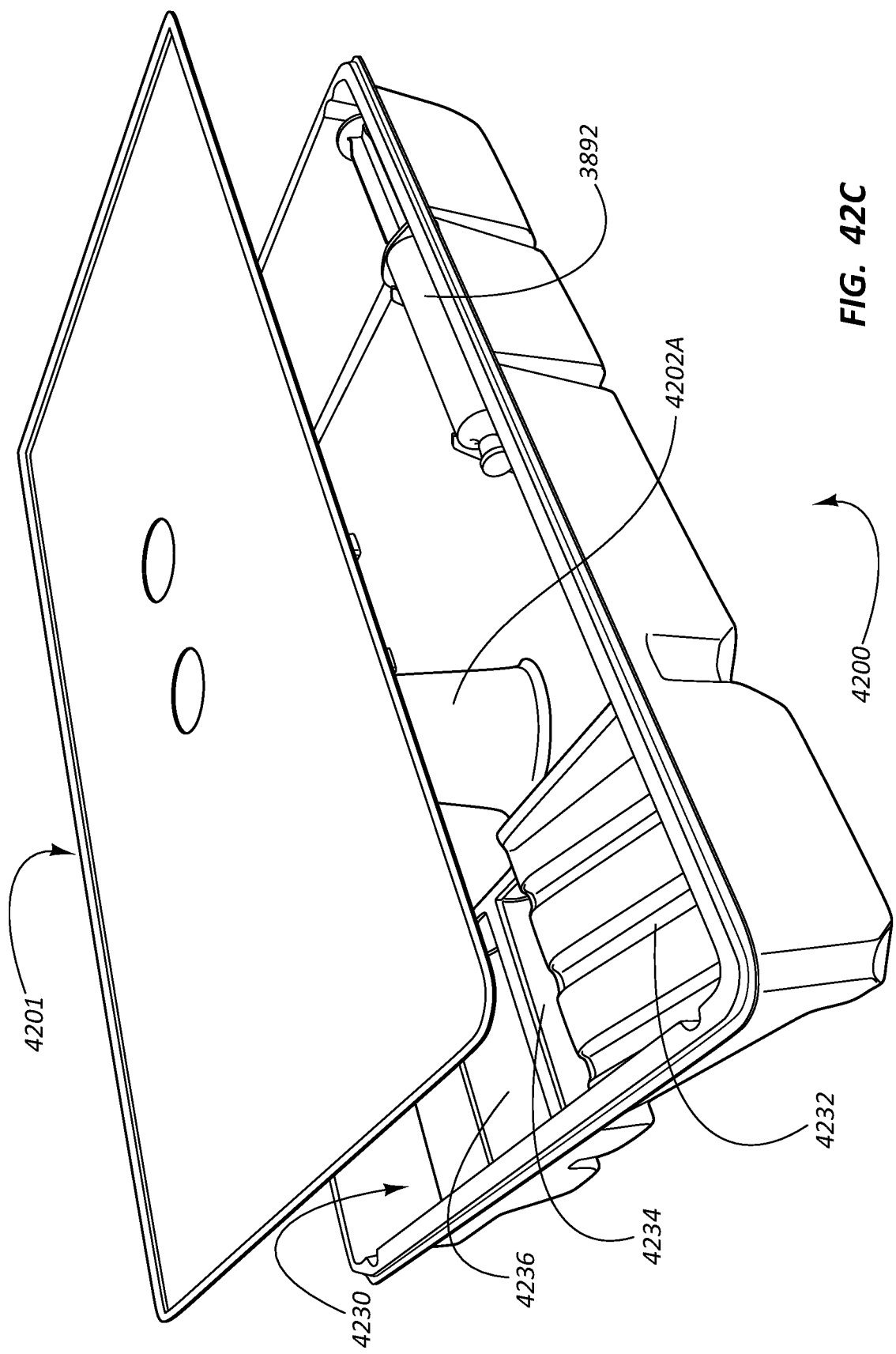

FIG. 42A shows a view of another medical-procedure tray 4200 in accordance with some embodiments. FIG. 42B shows another view of the medical-procedure tray 4200 of FIG. 42A.

The medical-procedure tray 4200 of FIGS. 42A and 42B can have a configuration similar to the medical-procedure tray 4100 described in reference to FIGS. 41A and 41B. As such, the tray 4200 can likewise include a first section 4210, a second section 4220, and a third section 4230, each of which can be configured to accommodate and hold contents for a medical procedure. The first section 4210, for example, can be configured to accommodate the previously described first set of contents for the catheterization procedure including the drainage system including the catheter (e.g., the Foley catheter), the drainage tubing, the drainage bag, and the syringe of sterile water 3892 for inflating the balloon of the Foley catheter. For a visual reference, the syringe of sterile water 3892 is shown mounted in or on a rack-type retainer of the first section 4210. In addition, the first section can be configured with an optional support 4202A to prevent caving of a cover placed thereon or thereover as described herein. The second section 4220, for example, can be configured to accommodate the previously described second set of contents for the catheterization procedure including the container containing lubricant (e.g., lubricant for the Foley catheter) such as a syringe of lubricant 4194. For a visual reference, the syringe of lubricant 4194 is shown mounted in or on a rack-type retainer 4214 in the second section 4220. The third section 4230, for example, can be configured with a swab compartment 4232, an overflow compartment 4234, and a corner storage compartment 4236 configured as described herein to accommodate the previously described third set of contents for the catheterization procedure including the specimen container, optionally, the label for the specimen container, and the skin-preparation kit including the packet of antiseptic (e.g., an iodophor such as povidone-iodine, tincture of iodine, aqueous iodine, etc.) and the one or more swabs.

With respect to the third section 4230, however, the third section 4230 of the tray 4200 can have a different configuration than, for example, the third section of any one tray of the trays 3800, 3900A-C, 4000, and 4100 in that at least the orientation of the third section 4230 of the tray 4200 is in a reversed orientation with respect to any one tray of the other foregoing trays. For example, the orientation of the third section 3830 of the tray 3800 is such that the well 3831 of the swab compartment 3832 or a well-end of the third section 3830 is adjacent the second section 3820 of the tray 3800. In such an orientation, the corner storage compartment 3836 shares with the tray 3800 an inner wall of the tray 3800. In contrast, the reversed orientation of the third section 4230 of the tray 4200 is such that the well (not shown) of the swab compartment 4232 or a well-end of the third section 4230 shares with the tray 4200 an inner wall of the tray 4200. In such an orientation, the corner storage compartment 4236 is adjacent the second section 4220 of the tray 4200. Any one or more of the trays provided herein including any one or more of the trays selected from the trays 3800, 3900A-C, 4000, and 4100 can be configured with a third section in the reverse orientation.

Adverting to FIG. 42B, the medical-procedure tray 4200 is shown together with a cover 4201 such as the packaging label 62 described in reference to FIGS. 11 and 12, the identification cover 120 described in reference to FIG. 30A, or a combination thereof. As shown, the cover 4201 can be configured to fit over the whole medical-procedure tray 4200; however, the cover 4201 can be alternatively configured to fit over a portion of the medical-procedure tray 4200, the portion including any one or more sections selected from the first section 4210, the second section 4220, and the third section 4230. The cover 4201 can be alternatively configured to fit within the medical-procedure tray 4200 in any of the foregoing configurations such as within the whole medical-procedure tray 4200 or a portion of the medical-procedure tray 4200. (See, for example, cover 3801 of FIGS. 38C and 38D.) As further shown, the tray 4200 can be configured with an optional support 4202B in the first section 4110 of the tray 4100, which support 4202B is shown in a different location of the first section 4110 than the optional support 4202A of FIG. 42A. The optional supports 4202A and 4202B can vary in location in accordance with packaging and stacking needs. Again, a support such as the support 4202B can prevent caving of the cover 4201 and damage to the contents of the tray 4200 thereunder when one or more medical-procedure packages are stacked on the medical-procedure package including the medical-procedure tray 4200 and the cover 4201. Each support of the supports 4202A and 4202B can be configured with a height substantially equal to a height of the tray 4200 and a width sufficient to withstand the weight of a stack of one or more medical-procedure packages stacked thereon.

Figure 43:
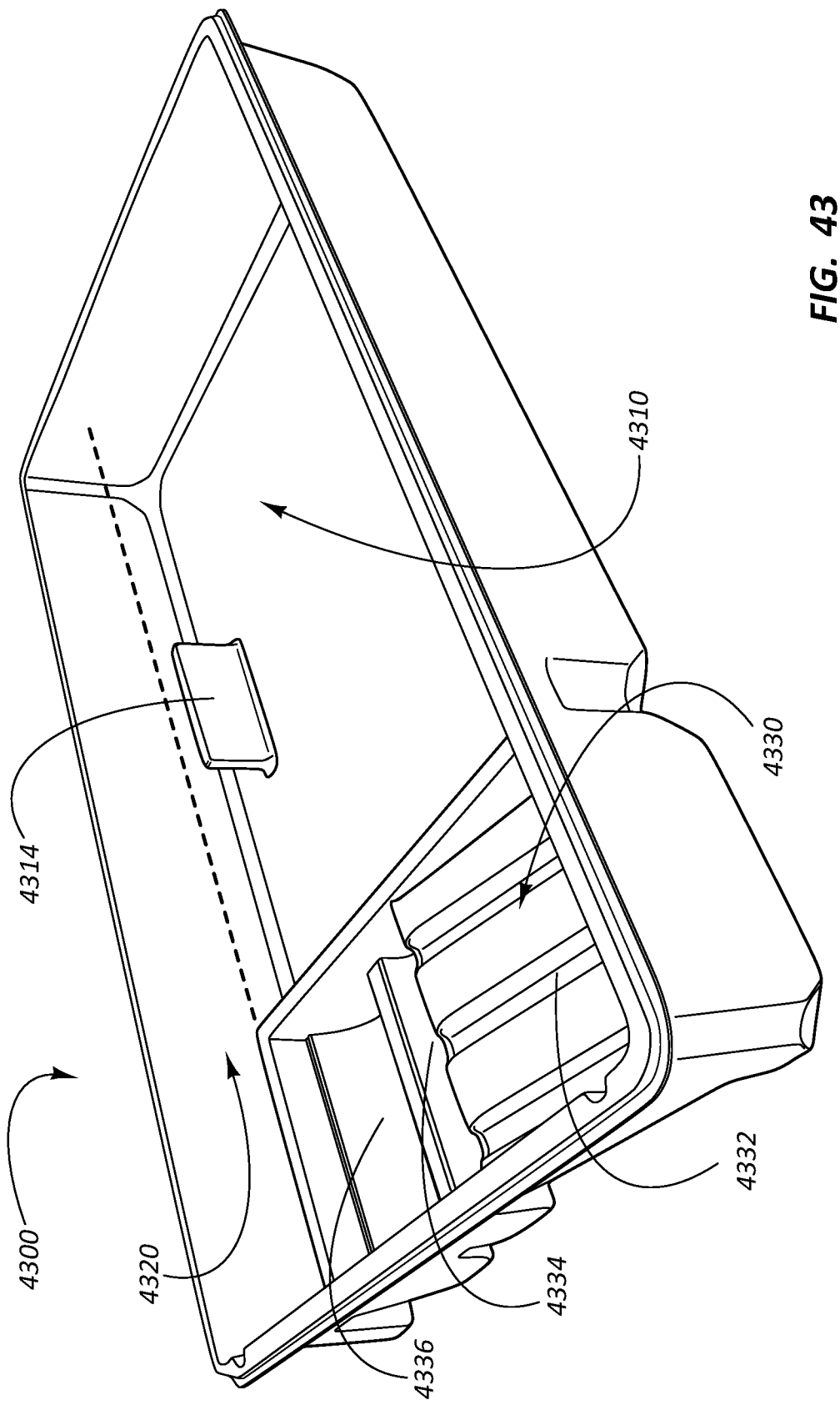
FIG. 43 shows a view of another medical-procedure tray in accordance with some embodiments.

FIG. 43 shows a view of another medical-procedure tray 4300 in accordance with some embodiments.

The medical-procedure tray 4300 of FIG. 43 can have a configuration similar to the medical-procedure tray 4200 described in reference to FIGS. 42A and 42B. As such, the tray 4300 can likewise include a first section 4310, a second section 4320, and a third section 4330 in the reverse orientation described in reference to tray 4200. Each of the first section 4310, the second section 4320, and the third section 4330 can be configured to accommodate and hold contents for a medical procedure. The first section 4310, for example, can be configured to accommodate the previously described first set of contents for the catheterization procedure including the drainage system including the catheter (e.g., the Foley catheter), the drainage tubing, the drainage bag, and the syringe of sterile water for inflating the balloon of the Foley catheter. While not shown, the first section 4310 can be configured with a tab-type retainer to retain or otherwise secure the syringe of sterile water. The second section 4320, for example, can be configured to accommodate the previously described second set of contents for the catheterization procedure including the container containing lubricant (e.g., lubricant for the Foley catheter), which container of lubricant can be retained or otherwise secured in the second section 4320 by a tab-type retainer 4314 in the second section 4320. The reverse-orientation third section 4330, for example, can be configured with a swab compartment 4332, an overflow compartment 4334, and a corner storage compartment 4336 configured as described herein to accommodate the previously described third set of contents for the catheterization procedure including the specimen container, optionally, the label for the specimen container, and the skin-preparation kit including the packet of antiseptic (e.g., an iodophor such as povidone-iodine, tincture of iodine, aqueous iodine, etc.) and the one or more swabs. Like the tray 4200 of FIGS. 42A and 42B, the corner storage compartment 4336 is adjacent the second section 4320 of the tray 4300; however, the second section 4320 of the tray 4300 extends from an inner wall of the first section 4310 of the tray 4300 all the way to an inner wall on an opposite side of the tray 4300 shared by the third section 4330, whereas the second section 4220 of the tray 4200 does not. That being said, the second section 4220 of the tray 4200 can be configured to likewise extend from an inner wall of the first section 4210 of the tray 4200 all the way to an inner wall on an opposite side of the tray 4200 shared by the third section 4230.

Figure 44A:
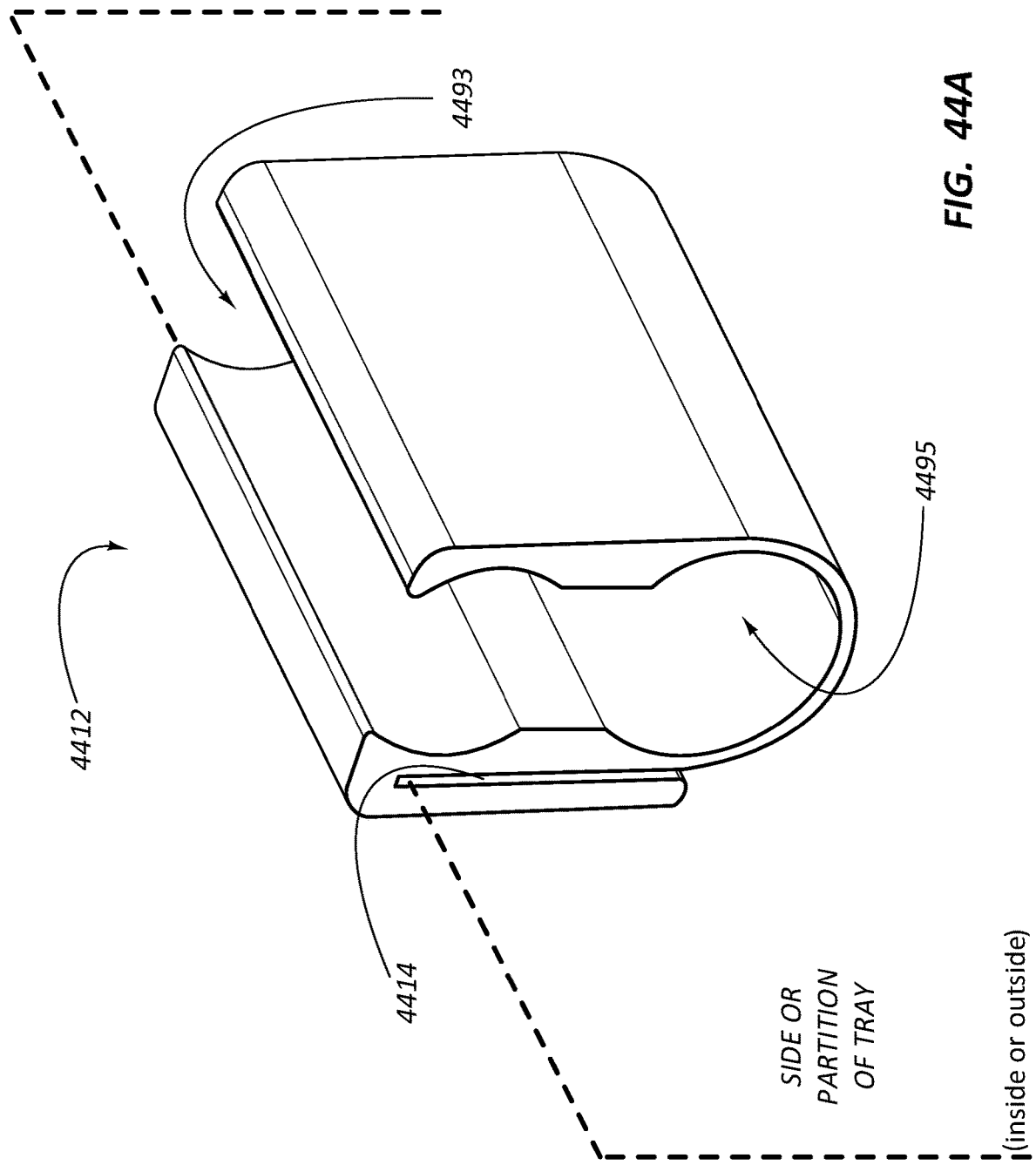
FIG. 44A shows a view of a removable retainer on a partition or a side of a medical-procedure tray in accordance with some embodiments.
Figure 44B:
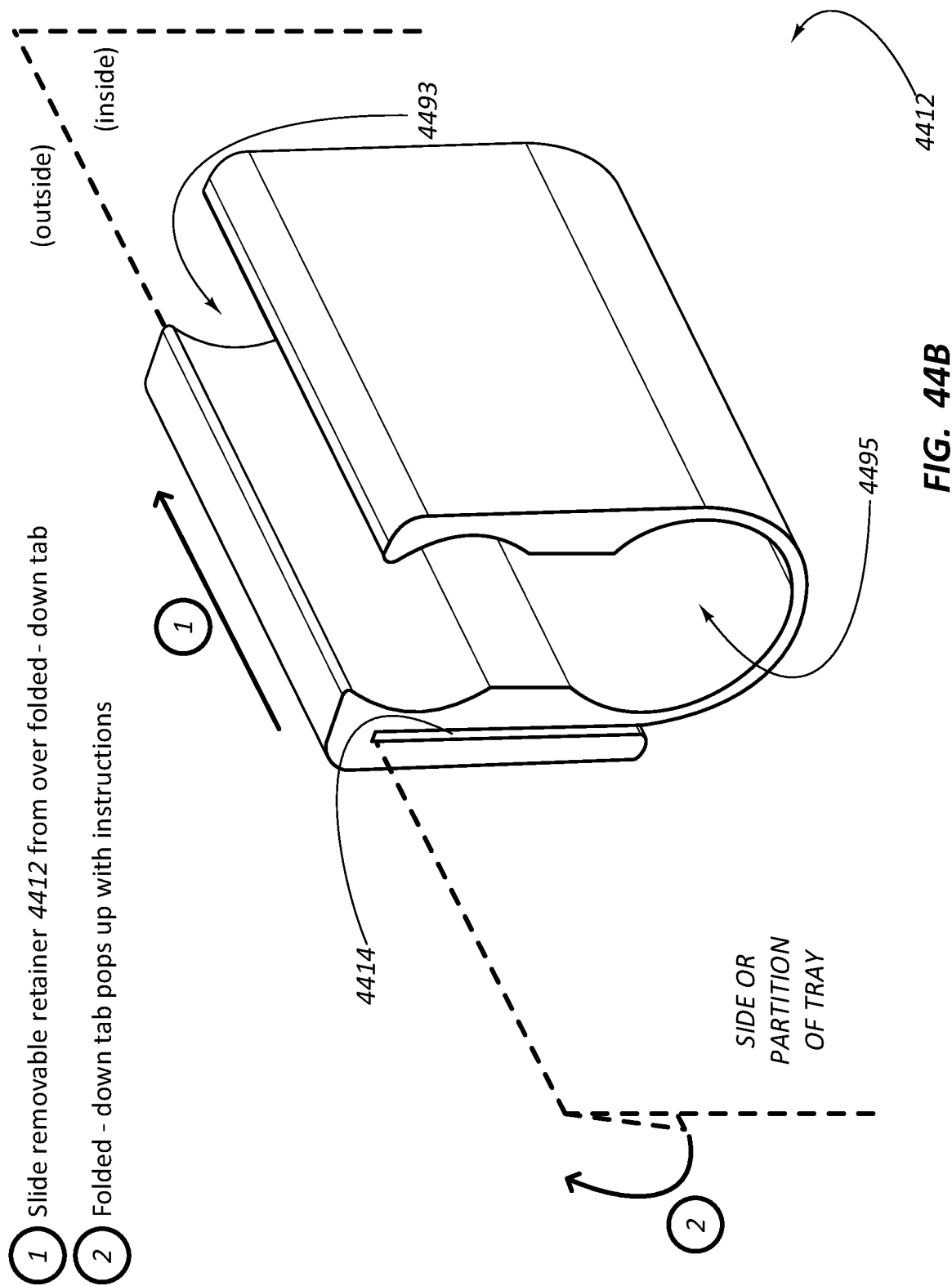
FIG. 44B shows another view of a removable retainer on a partition or a side of a medical-procedure tray with a concealed tab of instructions in accordance with some embodiments.
Figure 44C:
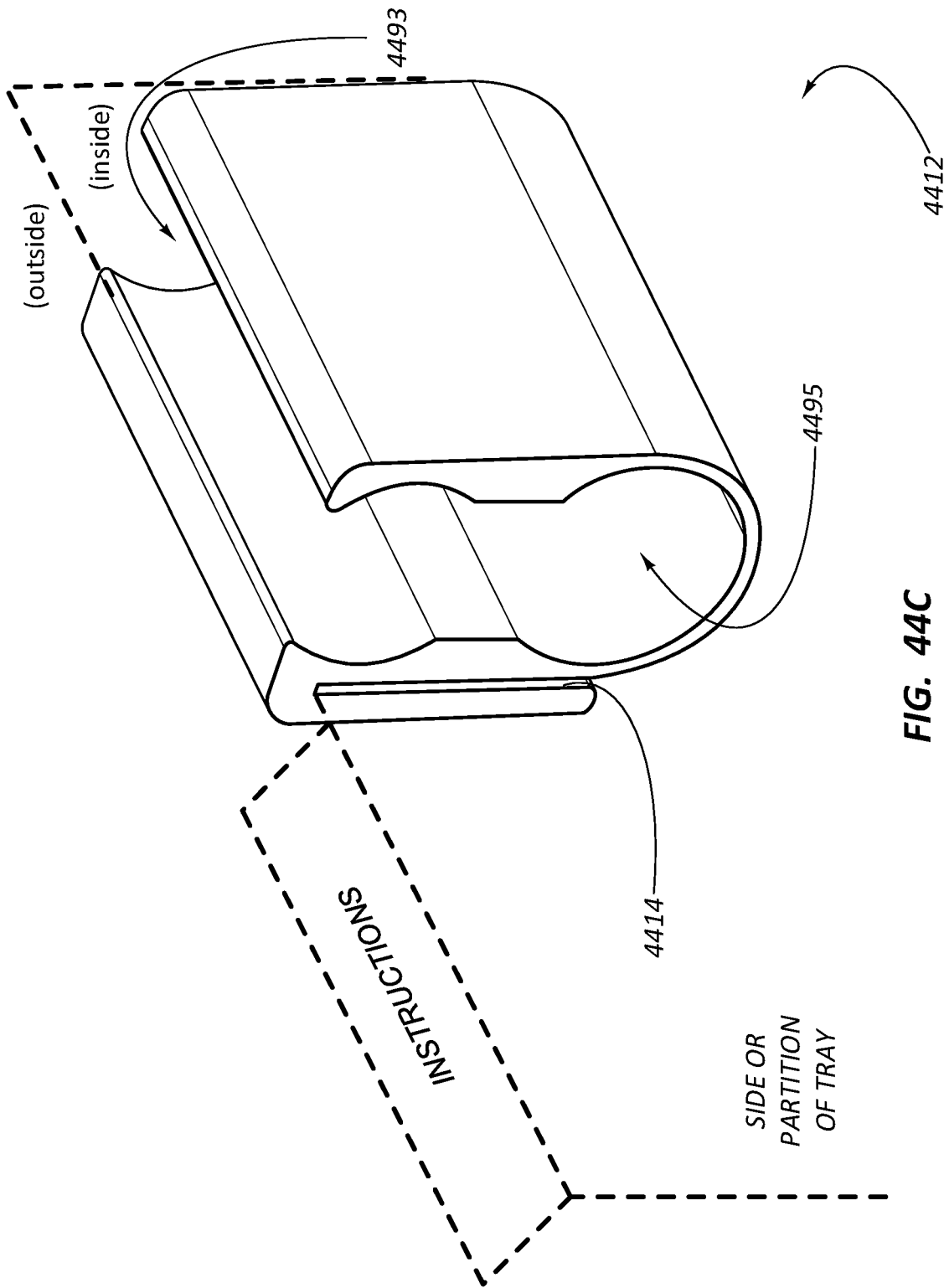
FIG. 44C shows another view of a removable retainer on a partition or a side of a medical-procedure tray with a revealed tab of instructions in accordance with some embodiments.

FIG. 44A shows a view of a removable retainer 4412 on a partition or a side of a medical-procedure tray in accordance with some embodiments. FIG. 44B shows another view of the removable retainer 4412 on the partition or the side of the medical-procedure tray with a concealed tab of instructions in accordance with some embodiments. FIG. 44C shows another view of the removable retainer on the partition or the side of the medical-procedure tray with a revealed tab of instructions in accordance with some embodiments.

Figure 45:
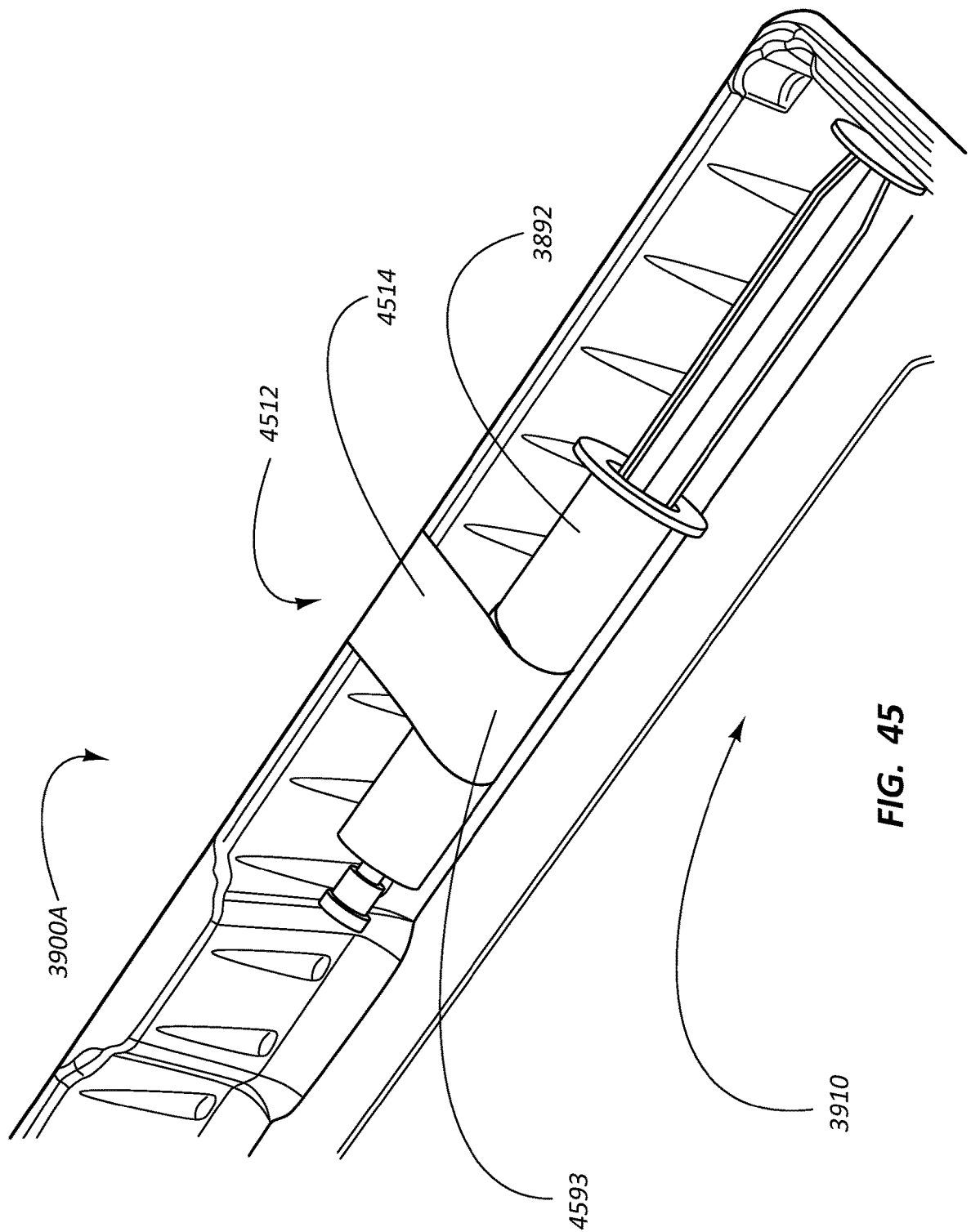
FIG. 45 shows a view of an appendage-type retainer on a side of a medical-procedure tray in accordance with some embodiments.

Any medical-procedure tray provided herein can optionally include any number of retainers of any type selected from at least column or tapered column-type retainers, rack-type retainers, and tab-type retainers for retaining certain contents of the medical-procedure package in the appropriate sections. For example, the tray 3900A can include three tapered column-type retainers providing the tray 3900B in which the three tapered column-type retainers retain or otherwise keep the syringe of sterile water 3892 in the first section 3910 apart from other contents of the medical-procedure package including the other contents in the first section 3810. (See FIG. 39C and the retainer 3912 in the first section 3910 retaining the syringe 3892.) Furthermore, any medical-procedure tray provided herein can optionally include one or more appendage-type retainers for retaining certain contents of the medical-procedure package in the appropriate sections. For example, as shown in FIG. 45 an appendage-type retainer 4512 can include a clip section 4593 for clipping the syringe of sterile water 3892 (or the container of lubricant 3894) to the appendage-type retainer 4512, and the appendage-type retainer 4512 can include an appending belt or strap section 4514 for appending the clip section 4593 to either the tray (e.g., a side of the tray as shown) or a cover (e.g., an underside of the cover) therefor. Instructions for one or more steps of a medical procedure can be printed on or imprinted in a visible surface of the belt or strap section 4514.

Whether or not a medical-procedure tray includes any of the foregoing retainers (e.g., the column or tapered column-type retainers, the rack-type retainers, the tab-type retainers, and the appendage-type retainers), the medical-procedure tray can include one or more removable retainers. An example of a removable retainer is the removable retainer 4412 of FIGS. 44A, 44B, and 44C, which is configured to keep the syringe of sterile water 3892 and the container of lubricant 3894 apart from other contents of the medical-procedure package. However, it should be understood that removable retainers are not limited to the removable retainer 4412. For example, a removable retainer can be configured to retain only the syringe of sterile water 3892 or only the container of lubricant 3894. Furthermore, a removable retainer can be configured to retain other contents of the medical-procedure package in the appropriate sections therefor.

As shown in FIGS. 44A, 44B, and 44C, a removable retainer such as the removable retainer 4412 can include a clip such as clip 4414 for removably attaching the removable retainer to a partition or a side of a medical-procedure tray. The clip can be configured to clip the removable retainer onto a partition or a side of a medical-procedure tray such that the removable retainer is either inside the medical-procedure tray (e.g., as packaged) or outside the medical-procedure tray (e.g., when in use during a medical procedure). The clip can be configured to clip the removable retainer onto a partition or a side of a medical-procedure tray with a clip force sufficient to restrict slideable movement of the removable retainer along the side or the partition of a medical-procedure tray. Alternatively, the clip can be configured to allow such slideable movement. When the clip is configured to allow slideable movement of the removable retainer along a partition or a side of a medical-procedure tray, less clip force or another captivating means other than clip force can be used to captivate or otherwise hold the removable retainer on the partition or the side of a medical-procedure tray until the removable retainer is deliberately removed.

The slideable movement of the removable retainer can be used to reveal or conceal instructions for one or more steps of a medical procedure. As shown in FIG. 44B, a removable retainer such as the removable retainer 4412 can be packaged on an inside of a medical-procedure tray concealing a folded-down tab of the instructions for the one or more steps of the medical procedure. While the folded-down tab of the instructions is shown in FIGS. 44B and 44C on an outside of the medical-procedure tray, the tray can be alternatively configured with the folded-down tab of the instructions on the inside of the tray. Regardless of the outside or the inside configuration of the folded-down tab of the instructions, the removable retainer can be slid aside as shown in FIG. 44B to reveal the instructions shown in FIG. 44C, which instructions can be printed or imprinted on the tab. The instructions can again be concealed by pushing the tab of the instructions in toward the inside or the outside of the tray and sliding the removable retainer thereover. Concealing the instructions in the folded-down tab can reduce an amount of information a health care provider needs to know to only the information immediately needed to perform one or more immediate steps of the medical procedure. This can, in turn, reduce errors in the medical procedure. Furthermore, the folded-down tab of the instructions can further conceal sharp edges of the tab that might otherwise compromise sterile packaging if left in an unfolded or extended position.

Again, the removable retainer 4412 of FIGS. 44A, 44B, and 44C is an example of a removable retainer configured to keep the syringe of sterile water 3892 and the container of lubricant 3894 apart from other contents of the medical-procedure package. As shown in FIGS. 44A, 44B, and 44C, the removable retainer 4412 can include another, wider clip (e.g., wider than clip 4414) configured with a first clip section 4493 for clipping the syringe of sterile water 3892 and a second clip section 4495 for the container of lubricant 3894. Depending upon dimensions of the syringe of sterile water 3892 and the container of lubricant 3894, the first clip section 4493 and the second clip section 4495 can have the same dimensions as each other or different dimensions from each other. Regardless, the syringe of sterile water 3892 and the container of lubricant 3894 can be arranged in the removable retainer 4412 in step with one or more steps of a medical procedure. For example, instructions for the one or more steps of the medical procedure might recommend connecting the syringe of sterile water 3892 to a Foley catheter in a first step, and the instructions might recommend lubricating the Foley catheter in a second step.

While the invention has been described in terms of particular variations and illustrative figures, those of ordinary skill in the art will recognize that the invention is not limited to the variations or figures described. In addition, where methods and steps described above indicate certain events occurring in certain order, those of ordinary skill in the art will recognize that the ordering of certain steps may be modified and that such modifications are in accordance with the variations of the invention. Additionally, certain of the steps may be performed concurrently in a parallel process when possible, as well as performed sequentially as described above. Therefore, to the extent there are variations of the invention, which are within the spirit of the disclosure or equivalent to the inventions found in the claims, it is the intent that this patent will cover those variations as well.

What is claimed is:

1. A catheterization package, comprising:
   a catheterization tray including instructions imprinted on one or more surfaces thereof, the catheterization tray comprising:
      a first section defined by an outer perimeter wall and an inner partition;
      a second section separated from the first section by a first portion of the inner partition, wherein the first portion has a first height equivalent to a height of the outer perimeter wall defining the first section; and
      a third section separated from the first section by a second portion of the inner partition, wherein the inner partition along the second portion includes the first height and a second height less than the first height, the third section including an inclined surface and a well positioned at a lower end of the inclined surface;
   a drainage system disposed in the first section;
   a syringe containing water disposed within the first section;
   a container of lubricant disposed in the second section;
   a plurality of swabs disposed in the third section on the inclined surface, each of the plurality of swabs comprising an absorbent head and an elongate member, wherein:
      the absorbent head of each of the plurality of swabs is positioned in the well, and
      the elongate member of each of the swabs extends past the inclined surface opposite of the well; and
   a sterile wrap folded around the catheterization tray.

2. The catheterization package of claim 1, further comprising:
   a peri-care kit packaged with the catheterization tray outside the sterile wrap;
   a belly band outside the sterile wrap to hold the sterile wrap in a folded configuration around the catheterization tray; and
   a packaging label outside the sterile wrap for identifying the catheterization package.

3. The catheterization package of claim 1, wherein the inclined surface includes a channel configured to: i) hold a swab of the plurality of swabs; and ii) convey a fluid to the well when the swab is absent from the channel and the fluid is poured therein, the third section further comprising:
   an overflow compartment fluidly connected to the well through the channel, and
   a corner storage compartment holding a specimen container.

4. The catheterization package of claim 3, wherein the channel includes at least two snap-in tabs to hold the swab in the channel under the at least two snap-in tabs, and wherein each longitudinal side of the channel includes at least one of the at least two snap-in tabs.

5. The catheterization package of claim 1, wherein a bottom of the second section is elevated above a bottom of the first section.

6. The catheterization package of claim 1, wherein a bottom of the second section and a bottom of the first section are substantially co-planar.

7. The catheterization package of claim 1, wherein the second section and the third section extend along the outer perimeter wall an equivalent distance in a length direction of the catheterization tray.

8. The catheterization package of claim 1, wherein a syringe of sterile water is positioned along the outer perimeter wall in the first section.

9. The catheterization package of claim 8, wherein the syringe of sterile water is secured along the outer perimeter wall by a retainer.

10. The catheterization package of claim 9, wherein the retainer comprises a strap coupled to the outer perimeter wall.

11. The catheterization package of claim 9, wherein the retainer comprises a plurality of columns extending from a base of the first section, the plurality of columns equidistantly spaced from the outer perimeter wall.

12. The catheterization package of claim 9, wherein the retainer comprises a plurality of columns extending from a base of the first section, one of the plurality of columns offset from a line extending through at least two of the plurality of columns, the line parallel to the outer perimeter wall along a first length.

13. The catheterization package of claim 9, wherein the retainer comprises a plurality of racks extending from a base of the first section, the plurality of racks having a height less than the height of the outer perimeter wall, the syringe of sterile water mounted on the plurality of racks.

14. The catheterization package of claim 9, wherein the retainer comprises a removable clip having a first clip section designed for retaining the syringe of sterile water.

15. The catheterization package of claim 8, wherein the syringe of sterile water is held between the outer perimeter wall and the inner partition.

16. The catheterization package of claim 8, further comprising a cover disposed over the drainage system in the first section.

17. The catheterization package of claim 16, wherein the cover includes a retainer designed to accommodate the syringe of sterile water.

18. A catheterization tray bounded by an outer perimeter wall, the catheterization tray comprising:
    a main section configured to hold a Foley catheter drainage system, the main section including a syringe retainer;
    a first side section configured to hold a container of lubricant; and
    a second side section separated from the first side section by a side section partition, the second side section including an inclined surface; and
    a continuous main section partition separating the main section from the first side section and the second side section.

19. The catheterization tray of claim 18, further comprising instructions printed on a bottom surface of the main section, the first side section, and the second side section.

20. The catheterization tray of claim 18, wherein the second side section further comprises a well at a lower end of the inclined surface, and an overflow compartment adjacent an upper end of the inclined surface.

21. The catheterization tray of claim 20, wherein the second side section further comprises a specimen container compartment adjacent the overflow compartment.

22. The catheterization tray of claim 18, wherein the inclined surface includes a plurality of channels, each of the plurality of channels including one or more snap-in tabs configured to releasably retain an elongate member of a swab.

23. The catheterization tray of claim 18, wherein the syringe retainer comprises a strap coupled to the outer perimeter wall.

24. The catheterization tray of claim 18, wherein the syringe retainer comprises a plurality of columns extending from a bottom surface of the main section, the plurality of columns equidistantly spaced from the outer perimeter wall.

25. The catheterization tray of claim 18, wherein the syringe retainer comprises a plurality of columns extending from a bottom surface of the main section, one of the plurality of columns offset from a line extending through at least two of the plurality of columns, the line parallel to the outer perimeter wall.

26. The catheterization tray of claim 18, wherein the syringe retainer comprises a plurality of racks extending from a bottom surface of the main section, the plurality of racks having a height less than a height of the outer perimeter wall.

27. The catheterization tray of claim 18, wherein the syringe retainer comprises a removable clip having a first clip section designed for retaining the syringe.

\* \* \* \* \*